United States Patent
Ubasawa et al.

[11] Patent Number: 5,840,716
[45] Date of Patent: Nov. 24, 1998

[54] PHOSPHONATE NUCLEOTIDE COMPOUNDS

[75] Inventors: Masaru Ubasawa; Kouichi Sekiya; Hideaki Takashima; Naoko Ueda; Satoshi Yuasa; Naohiro Kamiya, all of Kanagawa, Japan

[73] Assignee: Mitsubishi Chemical Corporation, Tokyo, Japan

[21] Appl. No.: 785,606

[22] Filed: Jan. 17, 1997

[30] Foreign Application Priority Data

Jan. 18, 1996 [JP] Japan ................................ 8-006480

[51] Int. Cl.[6] ................................ A01N 57/00; C07F 9/02
[52] U.S. Cl. ........................ 514/75; 514/79; 514/80; 514/81; 544/243; 544/244
[58] Field of Search ................ 514/75, 79, 80, 514/81; 544/243, 244

[56] References Cited

FOREIGN PATENT DOCUMENTS

| 0 478 292 | 4/1992 | European Pat. Off. . |
| 0 618 214 | 10/1994 | European Pat. Off. . |
| 0 632 048 | 1/1995 | European Pat. Off. . |

*Primary Examiner*—Ardin H. Marschel
*Assistant Examiner*—Jezia Riley
*Attorney, Agent, or Firm*—Wenderoth, Lind & Ponack, L.L.P.

[57] ABSTRACT

A phosphonate nucleotide compound having antiviral activity and is useful for an orally available and highly safe antiviral agent, which is represented by the following formula (I):

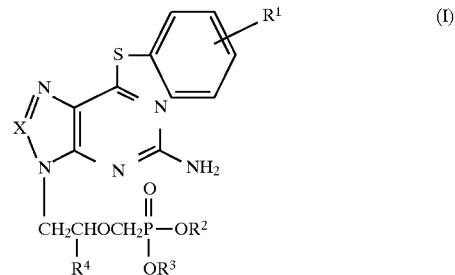

wherein $R^1$ represents hydrogen, a $C_1$–$C_6$ alkoxy, a halogen-substituted $C_1$–$C_4$ alkoxy, halogen, amino, or nitro; $R^2$ and $R^3$ independently represent hydrogen, a $C_1$–$C_{22}$ alkyl, an acyloxymethy, an acylthioethyl, or a halogen-substituted ethyl; $R^4$ represents hydrogen, a $C_1$–$C_4$ alkyl, a $C_1$–$C_4$ hydroxyalkyl, or a halogen-substituted $C_1$–$C_4$ alkyl; and X represents carbon or nitrogen.

18 Claims, No Drawings

PHOSPHONATE NUCLEOTIDE COMPOUNDS

FIELD OF THE INVENTION

The present invention relates to novel phosphonate nucleotide compounds. More specifically, the present invention relates to phosphonate nucleotide compounds and their salts, and hydrates and solvates thereof, which have antiviral activity and are useful as medicaments.

BACKGROUND OF THE INVENTION

Viral Infectious diseases are recognized as serious clinical problems. In order to therapeutically treat such diseases, attempts have been made to develop medicaments having antiviral activity, while exhibiting no growth inhibitory activity against normal cells systems. For example, extensive recent researches has been focused on phosphonate nucleotides as selective antiviral agents. More specifically, 9-(2-phosphonylmethoxy) ethyladenine (PMEA), 9-(2-phosphonylmethoxy)ethyl-2,6-diaminopurine (PMDAP) and the like are reported as being effective against herpes simplex type 1 and 2 viruses (HSV-1 and HSV-2), human immunodeficiency virus (HIV), and human hepatitis B virus (HBV) (Yokota et al., Antimicrob. Agents Chemother., 35, 394, 1991; Votruba et al., Mol. Pharmacol., 32, 524, 1987).

However, these known phosphonate nucleotides have problems of insufficient safety because they have toxicities against living bodies, whose typical example includes bone marrow cell growth inhibition, and have potential mutagenicities (Antiviral Research, 16, 77, 1991). In addition, there is another problem that they are not orally absorbable (De Clercq et al., Antimicrob. Agents Chemother., 33, 185, 1989), and their administration routes are limited to parenteral routes such as intravenous or intramuscular injection to achieve blood concentrations essential for exhibiting pharmacological effects. Therapeutic treatment by parenteral administration can hardly be carried out for patients other than inpatients, and is not preferably applied to treatments of AIDS, hepatitis B virus infection and the like which require long-term care.

The inventors of the present invention found that particular ester derivatives of phosphonate nucleotides have high oral absorbability (EP 632,048 A1). However, they have not yet been clinically developed.

SUMMARY OF THE INVENTION

An object of the present invention is to provide an antiviral agent having no toxicity such as growth inhibition against bone marrow cells or mutagenicity. Another object of the present invention is to provide an antiviral agent having excellent oral absorbability.

The inventors of the present invention conducted various studies to achieve the foregoing objects, and as a result, they found that particular 2-amino-6-arylthiopurinephosphonates, which are not specifically disclosed in the aforementioned EP 632,048 A1, have high antiviral activities, and that these compounds are safer to living bodies than conventionally proposed compounds and have excellent oral absorbability. The present invention was achieved on the basis of these findings.

The present invention thus provides phosphonate nucleotide compounds represented by the following formula (I) and their salts, and hydrates and solvates thereof:

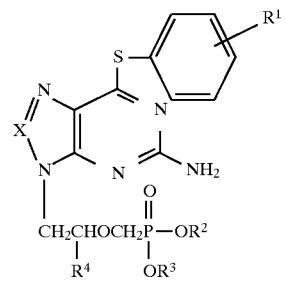

wherein $R^1$ represents hydrogen atom, a $C_1$–$C_6$ alkoxy group, a $C_1$–$C_4$ alkoxy group substituted with one or more halogen atoms, a halogen atom, amino group, or nitro group; $R^2$ and $R^1$ independently represent hydrogen atom, a $C_1$–$C_{22}$ alkyl group, an acyloxymethyl group, an acylthioethyl group, or an ethyl group substituted with one or more halogen atoms; $R^4$ represents hydrogen atom, a $C_1$–$C_4$ alkyl group, a $C_1$–$C_4$ hydroxyalkyl group, or a $C_1$–$C_4$ alkyl group substituted with one or more halogen atoms; and X represents a carbon atom or a nitrogen atom.

According to another aspect of the present invention, there are provided a pharmaceutical composition comprising a substance selected from the group consisting of the aforementioned compound and its salt, and a hydrate and a solvate thereof together with a pharmaceutically acceptable additive; and an antiviral agent comprising as an active ingredient a substance selected from the group consisting of the aforementioned compound and its salt, and a hydrate and a solvate thereof.

According to further aspect of the present invention, there are provided a use of a substance selected from the group consisting of the aforementioned compound and its salt, and a hydrate and a solvate thereof for the manufacture of the aforementioned pharmaceutical composition; and a method for therapeutic treatment of a viral infectious disease which comprises a step of administering to a mammal including a human an effective amount of a substance selected from the group consisting of the aforementioned compound and its salt, and a hydrate and a solvate thereof.

DETAILED EXPLANATION OF PREFERRED EMBODIMENTS OF THE INVENTION

In the phosphonate nucleotide compounds of the above general formula (I), examples of the $C_1$–$C_6$ alkoxy group represented by $R^1$ include methoxy group, ethoxy group, n-propoxy group, isopropoxy group, n-butoxy group, isobutoxy group, sec-butoxy group, tert-butoxy group, n-pentyloxy group, and n-hexyloxy group. Examples of the $C_1$–$C_4$ alkoxy group substituted with one or more halogen atoms represented by $R^1$ include monofluoromethoxy group, difluoromethoxy group, trifluoromethoxy group, monofluoroethoxy group, difluoroethoxy group, trifluoroethoxy group, tetrafluoroethoxy group, pentafluoroethoxy group, monofluoropropoxy group, difluoropropoxy group, trifluoropropoxy group, tetrafluoropropoxy group, pentafluoropropoxy group, hexafluoropropoxy group, heptafluoropropoxy group, monofluoroisopropoxy group, difluoroisopropoxy group, trifluoroisopropoxy group, tetrafluoroisopropoxy group, pentafluoroisopropoxy group, hexafluoroisopropoxy group, and heptafluoroisopropoxy group.

Examples of the $C_1$–$C_{22}$ alkyl group represented by $R^2$ and $R^3$ include methyl group, ethyl group, n-propyl group, isopropyl group, n-butyl group, isobutyl group, sec-butyl group, tert-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, heneicosyl group, and docosyl group. Examples of the acyloxymethyl group represented by $R^2$ and $R^3$ include acetyloxymethyl group, propionyloxymethyl group, butyryloxymethyl group, isobutyryloxymethyl group, valeryloxymethyl group, isovaleryloxymethyl group, and pivaloyloxymethyl group.

Examples of the acylthioethyl group represented by $R^2$ and $R^3$ include acetylthioethyl group, propionylthioethyl group, butyrylthioethyl group, isobutyrylthioethyl group, valerylthioethyl group, isovalerylthioethyl group, and pivaloylthioethyl. In the ethyl groups substituted with one or more halogen atoms represented by $R^2$ and $R^3$, the sort of halogen atoms may be any of fluorine atoms, chlorine atoms, bromine atoms, or iodine atoms. Examples of the ethyl group substituted with one or more halogen atoms include 1-fluoroethyl group, 2-fluoroethyl group, 1-chloroethyl group, 2-chloroethyl group, 2-bromoethyl group, 2,2-difluoroethyl group, 2,2-dichloroethyl group, 2,2-dibromoethyl group, 2,2,2-trifluoroethyl group, 2,2,2-trichloroethyl group, and 2,2,2-tribromoethyl group. In particular, the substitutions at 2-position of the ethyl groups are preferred, and fluorine atom is preferred among the halogen atoms. It is preferred that at least one of $R^2$ and $R^3$ is an ethyl group substituted with one or more halogen atoms, particularly 2,2,2-trifluoroethyl group.

Examples of the $C_1$–$C_4$ alkyl group represented by $R^4$ include methyl group, ethyl group, n-propyl group, isopropyl group, n-butyl group, isobutyl group, sec-butyl group, and tert-butyl group. Examples of the $C_1$–$C_4$ hydroxyalkyl group represented by $R^4$ include hydroxymethyl group, 1-hydroxyethyl group, 2-hydroxyethyl group, 1-hydroxypropyl group, 2-hydroxypropyl group, 3-hydroxypropyl group, 1-hydroxybutyl group, 2-hydroxybutyl group, 3-hydroxybutyl group, and 4-hydroxybutyl group. Examples of the $C_1$–$C_4$ alkyl group substituted with one or more halogen atoms represented by $R^4$ include methyl group, ethyl group, n-propyl group, isopropyl group, n-butyl group, isobutyl group, sec-butyl group, and tert-butyl group which are substituted with one or more halogen atoms such as fluorine atoms and chlorine atoms. More specifically, examples include fluoromethyl group, difluoromethyl group, trifluoromethyl group, fluoroethyl group, chloroethyl group, fluoropropyl group, chloropropyl group, fluorobutyl group, and chlorobutyl group.

According to the present invention, the first condition for preferred compounds includes that $R^1$ is hydrogen atom or a $C_1$–$C_6$ alkoxy group. The second condition for preferred compounds includes that $R^1$ is hydrogen atom or a $C_1$–$C_6$ alkoxy group; and $R^2$ and $R^3$ are independently selected from hydrogen atom, a $C_1$–$C_{22}$ alkyl group, or ethyl group substituted with one or more halogen atoms. In addition, the third condition for preferred compounds includes that $R^1$ is hydrogen atom or a $C_1$–$C_4$ alkoxy group; $R^2$ and $R^3$ are independently selected from hydrogen atom, a $C_1$–$C_{22}$ alkyl group, or 2,2,2-trifluoroethyl group; and $R^4$ is hydrogen atom or methyl group. The fourth condition for preferred compounds includes that $R^1$ is hydrogen atom or a $C_1$–$C_4$ alkoxy group; $R^2$ and $R^3$ are independently selected from hydrogen atom or 2,2,2-trifluoroethyl group; and $R^4$ is hydrogen atom or methyl group.

Examples of the preferred compounds satisfying the aforementioned conditions include the following compounds:
2-amino-9-[2-[bis(2,2,2-trifluoroethyl)phosphonylmethoxy]ethyl]-6-phenylthiopurine;
2-amino-9-[2-[bis(2,2,2-trifluoroethyl)phosphonylmethoxy]ethyl]-6-p-methoxyphenylthiopurine;
2-amino-9-[2-[bis(2,2,2-trifluoroethyl)phosphonylmethoxy]ethyl]-6-m-methoxyphenylthiopurine;
2-amino-9-[2-[bis(2,2,2-trifluoroethyl)phosphonylmethoxy]ethyl]-6-o-methoxyphenylthiopurine;
2-amino-9-[2-[bis(2,2,2-trifluoroethyl)phosphonylmethoxy]ethyl]-6-p-ethoxyphenylthiopurine;
2-amino-9-[2-[bis(2,2,2-trifluoroethyl)phosphonylmethoxy]propyl]-6-phenylthiopurine;
2-amino-9-[2-[bis(2,2,2-trifluoroethyl)phosphonylmethoxy]propyl]-6-p-methoxyphenylthiopurine;
2-amino-9-[2-[(2,2,2-trifluoroethyl)phosphonylmethoxy]ethyl]-6-phenylthiopurine;
2-amino-9-[2-[(2,2,2-trifluoroethyl)phosphonylmethoxy]ethyl]-6-p-methoxyphenylthiopurine;
2-amino-9-[2-[phosphonylmethoxy]ethyl]-6-phenylthiopurine;
2-amino-9-[2-[phosphonylmethoxy]ethyl]-6-p-methoxyphenylthiopurine;
2-amino-9-[2-[bis(2,2,2-trifluoroethyl)phosphonylmethoxy]ethyl]-6-p-butoxyphenylthiopurine;
2-amino-9-[2-[bis(2,2,2-trifluoroethyl)phosphonylmethoxy]ethyl]-6-p-propoxyphenylthiopurine;
2-amino-9-[2-[bis(2,2,2-trifluoroethyl)phosphonylmethoxy]ethyl]-6-p-isopropoxyphenylthiopurine; and
2-amino-9-[2-[bis(2,2,2-trifluoroethyl)phosphonylmethoxy]ethyl]-6-p-isobutoxyphenylthiopurine.

Other exemplary compounds satisfying the fourth condition include:
2-amino-9-[2-[bis(2,2,2-trifluoroethyl)phosphonylmethoxy]ethyl]-6-m-ethoxyphenylthiopurine;
2-amino-9-[2-[bis(2,2,2-trifluoroethyl)phosphonylmethoxy]ethyl]-6-o-ethoxyphenylthiopurine;
2-amino-9-[2-[bis(2,2,2-trifluoroethyl)phosphonylmethoxy]ethyl]-6-m-butoxyphenylthiopurine;
2-amino-9-[2-[bis(2,2,2-trifluoroethyl)phosphonylmethoxy]ethyl]-6-m-propoxyphenylthiopurine;
2-amino-9-[2-[bis(2,2,2-trifluoroethyl)phosphonylmethoxy]ethyl]-6-m-isopropoxyphenylthiopurine;
2-amino-9-[2-[bis(2,2,2-trifluoroethyl)phosphonylmethoxy]ethyl]-6-m-isobutoxyphenylthiopurine;
2-amino-9-[2-[bis(2,2,2-trifluoroethyl)phosphonylmethoxy]ethyl]-6-o-butoxyphenylthiopurine
2-amino-9-[2-[bis(2,2,2-trifluoroethyl)phosphonylmethoxy]ethyl]-6-o-propoxyphenylthiopurine;
2-amino-9-[2-[bis(2,2,2-trifluoroethyl)phosphonylmethoxy]ethyl]-6-o-isopropoxyphenylthiopurine;
2-amino-9-[2-[bis(2,2,2-trifluoroethyl)phosphonylmethoxy]ethyl]-6-o-isobutoxyphenylthiopurine;
2-amino-9-[2-[bis(2,2,2-trifluoroethyl)phosphonylmethoxy]propyl]-6-m-methoxyphenylthiopurine;
2-amino-9-[2-[bis(2,2,2-trifluoroethyl)phosphonylmethoxy]propyl]-6-o-methoxyphenylthiopurine;
2-amino-9-[2-[bis(2,2,2-trifluoroethyl)phosphonylmethoxy]propyl]-6-p-ethoxyphenylthiopurine;
2-amino-9-[2-[bis(2,2,2-trifluoroethyl)phosphonylmethoxy]propyl]-6-m-ethoxyphenylthiopurine;
2-amino-9-[2-[bis(2,2,2-trifluoroethyl)phosphonylmethoxy]propyl]-6-o-ethoxyphenylthiopurine;
2-amino-9-[2-[bis(2,2,2-trifluoroethyl)phosphonylmethoxy]propyl]-6-p-butoxyphenylthiopurine;
2-amino-9-[2-[bis(2,2,2-trifluoroethyl)phosphonylmethoxy]propyl]-6-p-propoxyphenylthiopurine;
2-amino-9-[2-[bis(2,2,2-trifluoroethyl)phosphonylmethoxy]propyl]-6-p-isopropoxyphenylthiopurine;
2-amino-9-[2-[bis(2,2,2-trifluoroethyl)phosphonylmethoxy]propyl]-6-p-isobutoxyphenylthiopurine;

2-amino-9-[2-[bis(2,2,2-trifluoroethyl)phosphonylmethoxy]propyl]-6-m-butoxyphenylthiopurine;
2-amino-9-[2-[bis(2,2,2-trifluoroethyl)phosphonylmethoxy]propyl]-6-m-propoxyphenylthiopurine;
2-amino-9-[2-[bis(2,2,2-trifluoroethyl)phosphonylmethoxy]propyl]-6-m-isopropoxyphenylthiopurine;
2-amino-9-[2-[bis(2,2,2-trifluoroethyl)phosphonylmethoxy]propyl]-6-m-isobutoxyphenylthiopurine;
2-amino-9-[2-[bis(2,2,2-trifluoroethyl)phosphonylmethoxy]propyl]-6-o-butoxyphenylthiopurine;
2-amino-9-[2-[bis(2,2,2-trifluoroethyl)phosphonylmethoxy]propyl]-6-o-propoxyphenylthiopurine;
2-amino-9-[2-[bis(2,2,2-trifluoroethyl)phosphonylmethoxy]propyl]-6-o-isopropoxyphenylthiopurine;
2-amino-9-[2-[bis(2,2,2-trifluoroethyl)phosphonylmethoxy]propyl]-6-o-isobutoxyphenylthiopurine;
2-amino-9-[2-[(2,2,2-trifluoroethyl)phosphonylmethoxy]ethyl]-6-m-methoxyphenylthiopurine;
2-amino-9-[2-[(2,2,2-trifluoroethyl)phosphonylmethoxy]ethyl]-6-o-methoxyphenylthiopurine;
2-amino-9-[2-[(2,2,2-trifluoroethyl)phosphonylmethoxy]ethyl]-6-p-ethoxyphenylthiopurine;
2-amino-9-[2-[(2,2,2-trifluoroethyl)phosphonylmethoxy]ethyl]-6-m-ethoxyphenylthiopurine;
2-amino-9-[2-[(2,2,2-trifluoroethyl)phosphonylmethoxy]ethyl]-6-o-ethoxyphenylthiopurine;
2-amino-9-[2-[(2,2,2-trifluoroethyl)phosphonylmethoxy]ethyl]-6-p-butoxyphenylthiopurine;
2-amino-9-[2-[(2,2,2-trifluoroethyl)phosphonylmethoxy]ethyl]-6-p-propoxyphenylthiopurine;
2-amino-9-[2-[(2,2,2-trifluoroethyl)phosphonylmethoxy]ethyl]-6-p-isopropoxyphenylthiopurine;
2-amino-9-[2-[(2,2,2-trifluoroethyl)phosphonylmethoxy]ethyl]-6-p-isobutoxyphenylthiopurine;
2-amino-9-[2-[(2,2,2-trifluoroethyl)phosphonylmethoxy]ethyl]-6-m-butoxyphenylthiopurine;
2-amino-9-[2-[(2,2,2-trifluoroethyl)phosphonylmethoxy]ethyl]-6-m-propoxyphenylthiopurine;
2-amino-9-[2-[(2,2,2-trifluoroethyl)phosphonylmethoxy]ethyl]-6-m-isopropoxyphenylthiopurine;
2-amino-9-[2-[(2,2,2-trifluoroethyl)phosphonylmethoxy]ethyl]-6-m-isobutoxyphenylthiopurine;
2-amino-9-[2-[(2,2,2-trifluoroethyl)phosphonylmethoxy]ethyl]-6-o-butoxyphenylthiopurine;
2-amino-9-[2-[(2,2,2-trifluoroethyl)phosphonylmethoxy]ethyl]-6-o-propoxyphenylthiopurine;
2-amino-9-[2-[(2,2,2-trifluoroethyl)phosphonylmethoxy]ethyl]-6-o-isopropoxyphenylthiopurine;
2-amino-9-[2-[(2,2,2-trifluoroethyl)phosphonylmethoxy]ethyl]-6-o-isobutoxyphenylthiopurine;
2-amino-9-[2-[(2,2,2-trifluoroethyl)phosphonylmethoxy]propyl]-6-phenylthiopurine;
2-amino-9-[2-[(2,2,2-trifluoroethyl)phosphonylmethoxy]propyl]-6-p-methoxyphenylthiopurine;
2-amino-9-[2-[(2,2,2-trifluoroethyl)phosphonylmethoxy]propyl]-6-m-methoxyphenylthiopurine;
2-amino-9-[2-[(2,2,2-trifluoroethyl)phosphonylmethoxy]propyl]-6-o-methoxyphenylthiopurine;
2-amino-9-[2-[(2,2,2-trifluoroethyl)phosphonylmethoxy]propyl]-6-p-ethoxyphenylthiopurine;
2-amino-9-[2-[(2,2,2-trifluoroethyl)phosphonylmethoxy]propyl]-6-m-ethoxyphenylthiopurine;
2-amino-9-[2-[(2,2,2-trifluoroethyl)phosphonylmethoxy]propyl]-6-o-ethoxyphenylthiopurine;
2-amino-9-[2-[(2,2,2-trifluoroethyl)phosphonylmethoxy]propyl]-6-p-butoxyphenylthiopurine;
2-amino-9-[2-[(2,2,2-trifluoroethyl)phosphonylmethoxy]propyl]-6-p-propoxyphenylthiopurine;
2-amino-9-[2-[(2,2,2-trifluoroethyl)phosphonylmethoxy]propyl]-6-p-isopropoxyphenylthiopurine;
2-amino-9-[2-[(2,2,2-trifluoroethyl)phosphonylmethoxy]propyl]-6-p-isobutoxyphenylthiopurine;
2-amino-9-[2-[(2,2,2-trifluoroethyl)phosphonylmethoxy]propyl]-6-m-butoxyphenylthiopurine;
2-amino-9-[2-[(2,2,2-trifluoroethyl)phosphonylmethoxy]propyl]-6-m-propoxyphenylthiopurine;
2-amino-9-[2-[(2,2,2-trifluoroethyl)phosphonylmethoxy]propyl]-6-m-isopropoxyphenylthiopurine;
2-amino-9-[2-[(2,2,2-trifluoroethyl)phosphonylmethoxy]propyl]-6-m-isobutoxyphenylthiopurine;
2-amino-9-[2-[(2,2,2-trifluoroethyl)phosphonylmethoxy]propyl]-6-o-butoxyphenylthiopurine;
2-amino-9-[2-[(2,2,2-trifluoroethyl)phosphonylmethoxy]propyl]-6-o-propoxyphenylthiopurine;
2-amino-9-[2-[(2,2,2-trifluoroethyl)phosphonylmethoxy]propyl]-6-o-isopropoxyphenylthiopurine;
2-amino-9-[2-[(2,2,2-trifluoroethyl)phosphonylmethoxy]propyl]-6-o-isobutoxyphenylthiopurine;
2-amino-9-[2-phosphonylmethoxyethyl]-6-m-methoxyphenylthiopurine;
2-amino-9-[2-phosphonylmethoxyethyl]-6-o-methoxyphenylthiopurine;
2-amino-9-[2-phosphonylmethoxyethyl]-6-p-ethoxyphenylthiopurine;
2-amino-9-[2-phosphonylmethoxyethyl]-6-m-ethoxyphenylthiopurine;
2-amino-9-[2-phosphonylmethoxyethyl]-6-o-ethoxyphenylthiopurine;
2-amino-9-[2-phosphonylmethoxyethyl]-6-p-butoxyphenylthiopurine;
2-amino-9-[2-phosphonylmethoxyethyl]-6-p-propoxyphenylthiopurine;
2-amino-9-[2-phosphonylmethoxyethyl]-6-p-isopropoxyphenylthiopurine;
2-amino-9-[2-phosphonylmethoxyethyl]-6-p-isobutoxyphenylthiopurine;
2-amino-9-[2-phosphonylmethoxyethyl]-6-m-butoxyphenylthiopurine;
2-amino-9-[2-phosphonylmethoxyethyl]-6-m-propoxyphenylthiopurine;
2-amino-9-[2-phosphonylmethoxyethyl]-6-m-isopropoxyphenylthiopurine;
2-amino-9-[2-phosphonylmethoxyethyl]-6-m-isobutoxyphenylthiopurine;
2-amino-9-[2-phosphonylmethoxyethyl]-6-o-butoxyphenylthiopurine;
2-amino-9-[2-phosphonylmethoxyethyl]-6-o-propoxyphenylthiopurine;
2-amino-9-[2-phosphonylmethoxyethyl]-6-o-isopropoxyphenylthiopurine;
2-amino-9-[2-phosphonylmethoxyethyl]-6-o-isobutoxyphenylthiopurine;
2-amino-9-[2-phosphonylmethoxypropyl]-6-phenylthiopurine;
2-amino-9-[2-phosphonylmethoxypropyl]-6-p-methoxyphenylthiopurine;
2-amino-9-[2-phosphonylmethoxypropyl]-6-m-methoxyphenylthiopurine; 2-amino-9-[2-phosphonylmethoxypropyl]-6-o-methoxyphenylthiopurine;
2-amino-9-[2-phosphonylmethoxypropyl]-6-p-ethoxyphenylthiopurine;
2-amino-9-[2-phosphonylmethoxypropyl]-6-m-ethoxyphenylthiopurine;
2-amino-9-[2-phosphonylmethoxypropyl]-6-o-ethoxyphenylthiopurine;

2-amino-9-[2-phosphonylmethoxypropyl]-6-p-butoxyphenylthiopurine;
2-amino-9-[2-phosphonylmethoxypropyl]-6-p-propoxyphenylthiopurine;
2-amino-9-[2-phosphonylmethoxypropyl]-6-p-isopropoxyphenylthiopurine;
2-amino-9-[2-phosphonylmethoxypropyl]-6-p-isobutoxyphenylthiopurine;
2-amino-9-[2-phosphonylmethoxypropyl]-6-m-butoxyphenylthiopurine;
2-amino-9-[2-phosphonylmethoxypropyl]-6-m-propoxyphenylthiopurine;
2-amino-9-[2-phosphonylmethoxypropyl]-6-m-isopropoxyphenylthiopurine;
2-amino-9-[2-phosphonylmethoxypropyl]-6-m-isobutoxyphenylthiopurine;
2-amino-9-[2-phosphonylmethoxypropyl]-6-o-butoxyphenylthiopurine;
2-amino-9-[2-phosphonylmethoxypropyl]-6-o-propoxyphenylthiopurine;
2-amino-9-[2-phosphonylmethoxypropyl]-6-o-isopropoxyphenylthiopurine; and
2-amino-9-[2-phosphonylmethoxypropyl]-6-o-isobutoxyphenylthiopurine.

The fifth condition for preferred compounds includes that $R^1$ is hydrogen atom or a $C_1$–$C_4$ alkoxy group; $R^2$ and $R^3$ are 2,2,2-trifluoroethyl groups; and $R^4$ is hydrogen atom or methyl group. Examples of the preferred compounds satisfying this condition include:
2-amino-9-[2-[bis(2,2,2-trifluoroethyl)phosphonylmethoxy]ethyl]-6-phenylthiopurine;
2-amino-9-[2-[bis(2,2,2-trifluoroethyl)phosphonylmethoxy]ethyl]-6-p-methoxyphenylthiopurine;
2-amino-9-[2-[bis(2,2,2-trifluoroethyl)phosphonylmethoxy]ethyl]-6-m-methoxyphenylthiopurine;
2-amino-9-[2-[bis(2,2,2-trifluoroethyl)phosphonylmethoxy]ethyl]-6-o-methoxyphenylthiopurine;
2-amino-9-[2-[bis(2,2,2-trifluoroethyl)phosphonylmethoxy]ethyl]6-p-ethoxyphenylthiopurine;
2-amino-9-[2-[bis(2,2,2-trifluoroethyl)phosphonylmethoxy]propyl]-6 -phenylthiopurine;
2-amino-9-[2-[bis(2,2,2-trifluoroethyl)phosphonylmethoxy]propyl]-6-p-methoxyphenylthiopurine;
2-amino-9-[2-[bis(2,2,2-trifluoroethyl)phosphonylmethoxy]ethyl]-6-p-butoxyphenylthiopurine;
2-amino-9-[2-[bis(2,2,2-trifluoroethyl)phosphonylmethoxy]ethyl]-6-p-propoxyphenylthiopurine;
2-amino-9-[2-[bis(2,2,2-trifluoroethyl)phosphonylmethoxy]ethyl]-6-p-isopropoxyphenylthiopurine; and
2-amino-9-[2-[bis(2,2,2-trifluoroethyl)phosphonylmethoxy]ethyl]-6-p-isobutoxyphenylthiopurine.

Other exemplary compounds satisfying the fifth condition include;
2-amino-9-[2-[bis(2,2,2-trifluoroethyl)phosphonylmethoxy]ethyl]-6-m-ethoxyphenylthiopurine;
2-amino-9-[2-[bis(2,2,2-trifluoroethyl)phosphonylmethoxy]ethyl]-6-o-ethoxyphenylthiopurine;
2-amino-9-[2-[bis(2,2,2-trifluoroethyl)phosphonylmethoxy]ethyl]-6-m-butoxyphenylthiopurine;
2-amino-9-[2-[bis(2,2,2-trifluoroethyl)phosphonylmethoxy]ethyl]-6-m-propoxyphenylthiopurine;
2-amino-9-[2-[bis(2,2,2-trifluoroethyl)phosphonylmethoxy]ethyl]-6-m-isopropoxyphenylthiopurine;
2-amino-9-[2-[bis(2,2,2-trifluoroethyl)phosphonylmethoxy]ethyl]-6-m-isobutoxyphenylthiopurine;
2-amino-9-[2-[bis(2,2,2-trifluoroethyl)phosphonylmethoxy]ethyl]-6-o-butoxyphenylthiopurine;
2-amino-9-[2-[bis(2,2,2-trifluoroethyl)phosphonylmethoxy]ethyl]-6-o-propoxyphenylthiopurine;
2-amino-9-[2-[bis(2,2,2-trifluoroethyl)phosphonylmethoxy]ethyl]-6-o-isopropoxyphenylthiopurine;
2-amino-9-[2-[bis(2,2,2-trifluoroethyl)phosphonylmethoxy]ethyl]-6-o-isobutoxyphenylthiopurine;
2-amino-9-[2-[bis(2,2,2-trifluoroethyl)phosphonylmethoxy]propyl]-6-m-methoxyphenylthiopurine;
2-amino-9-[2-[bis(2,2,2-trifluoroethyl)phosphonylmethoxy]propyl]-6-o-methoxyphenylthiopurine;
2-amino-9-[2-[bis(2,2,2-trifluoroethyl)phosphonylmethoxy]propyl]-6-p-ethoxyphenylthiopurine;
2-amino-9-[2-[bis(2,2,2-trifluoroethyl)phosphonylmethoxy]propyl]-6-m-ethoxyphenylthiopurine;
2-amino-9-[2-[bis(2,2,2-trifluoroethyl)phosphonylmethoxy]propyl]-6-o-ethoxyphenylthiopurine;
2-amino-9-[2-[bis(2,2,2-trifluoroethyl)phosphonylmethoxy]propyl]-6-p-butoxyphenylthiopurine;
2-amino-9-[2-[bis(2,2,2-trifluoroethyl)phosphonylmethoxy]propyl]-6-p-propoxyphenylthiopurine;
2-amino-9-[2-[bis(2,2,2-trifluoroethyl)phosphonylmethoxy]propyl]-6-p-isopropoxyphenylthiopurine;
2-amino-9-[2-[bis(2,2,2-trifluoroethyl)phosphonylmethoxy]propyl]-6-p-isobutoxyphenylthiopurine;
2-amino-9-[2-[bis(2,2,2-trifluoroethyl)phosphonylmethoxy]propyl]-6 -m-butoxyphenylthiopurine;
2-amino-9-[2-[bis(2,2,2-trifluoroethyl)phosphonylmethoxy]propyl]-6-m-propoxyphenylthiopurine;
2-amino-9-[2-[bis(2,2,2-trifluoroethyl)phosphonylmethoxy]propyl]-6-m-isopropoxyphenylthiopurine;
2-amino-9-[2-[bis(2,2,2-trifluoroethyl)phosphonylmethoxy]propyl]-6-m-isobutoxyphenylthiopurine;
2-amino-9-[2-[bis(2,2,2-trifluoroethyl)phosphonylmethoxy]propyl]-6-o-butoxyphenylthiopurine;
2-amino-9-[2-[bis(2,2,2-trifluoroethyl)phosphonylmethoxy]propyl]-6-o-propoxyphenylthiopurine;
2-amino-9-[2-[bis(2,2,2-trifluoroethyl)phosphonylmethoxy]propyl]-6-o-isopropoxyphenylthiopurine; and
2-amino-9-[2-[bis(2,2,2-trifluoroethyl)phosphonylmethoxy]propyl]-6-o-isobutoxyphenylthiopurine.

The sixth condition for preferred compounds includes that $R^1$ is hydrogen atom or a $C^1$–$C_4$ alkoxy group; $R^2$ and $R^3$ are 2,2,2-trifluoroethyl groups; and $R^4$ is hydrogen atom. Examples of the preferred compounds satisfying this condition include:
2-amino-9-[2-[bis(2,2,2-trifluoroethyl)phosphonylmethoxy]ethyl]-6-phenylthiopurine;
2-amino-9-[2-[bis(2,2,2-trifluoroethyl)phosphonylmethoxy]ethyl]-6-p-methoxyphenylthiopurine;
2-amino-9-[2-[bis(2,2,2-trifluoroethyl)phosphonylmethoxy]ethyl]-6-m-methoxyphenylthiopurine;
2-amino-9-[2-[bis(2,2,2-trifluoroethyl)phosphonylmethoxy]ethyl]-6-o-methoxyphenylthiopurine;
2-amino-9-[2-[bis(2,2,2-trifluoroethyl)phosphonylmethoxy]ethyl]-6-p-ethoxyphenylthiopurine;
2-amino-9-[2-[bis(2,2,2-trifluoroethyl)phosphonylmethoxy]ethyl]-6-p-butoxyphenylthiopurine;
2-amino-9-[2-[bis(2,2,2-trifluoroethyl)phosphonylmethoxy]ethyl]-6-p-propoxyphenylthiopurine;
2-amino-9-[2-[bis(2,2,2-trifluoroethyl)phosphonylmethoxy]ethyl]-6-p-isopropoxyphenylthiopurine; and
2-amino-9-[2-[bis(2,2,2-trifluoroethyl)phosphonylmethoxy]ethyl]-6-p-isobutoxyphenylthiopurine.

Other exemplary compounds satisfying the sixth condition include:
2-amino-9-[2-[bis(2,2,2-trifluoroethyl)phosphonylmethoxy]ethyl]-6-m-ethoxyphenylthiopurine;

2-amino-9-[2-[bis(2,2,2-trifluoroethyl)phosphonylmethoxy] ethyl]-6-o-ethoxyphenylthiopurine;
2-amino-9-[2-[bis(2,2,2-trifluoroethyl)phosphonylmethoxy] ethyl]-6-m-butoxyphenylthiopurine;
2-amino-9-[2-[bis(2,2,2-trifluoroethyl)phosphonylmethoxy] ethyl]-6-m-propoxyphenylthiopurine;
2-amino-9-[2-[bis(2,2,2-trifluoroethyl)phosphonylmethoxy] ethyl]-6-m-isopropoxyphenylthiopurine;
2-amino-9-[2-[bis(2,2,2-trifluoroethyl)phosphonylmethoxy] ethyl]-6-m-isobutoxyphenylthiopurine;
2-amino-9-[2-[bis(2,2,2-trifluoroethyl)phosphonylmethoxy] ethyl]-6 -o-butoxyphenylthiopurine;
2-amino-9-[2-[bis(2,2,2-trifluoroethyl)phosphonylmethoxy] ethyl]-6-o-propoxyphenylthiopurine;
2-amino-9-[2-[bis(2,2,2-trifluoroethyl)phosphonylmethoxy] ethyl]-6-o-isopropoxyphenylthiopurine; and
2-amino-9-[2-[bis(2,2,2-trifluoroethyl)phosphonylmethoxy] ethyl]-6-o-isobutoxyphenylthiopurine.

The seventh condition for preferred compounds includes that $R^1$ is hydrogen atom or a $C_1$–$C_2$ alkoxy group; $R^2$ and $R^3$ are 2,2,2-trifluoroethyl groups, and $R^4$ is hydrogen atom. Examples of the preferred compounds satisfying this condition include:
2-amino-9-[2-[bis(2,2,2-trifluoroethyl)phosphonylmethoxy] ethyl]-6-phenylthiopurine;
2-amino-9-[2-[bis(2,2,2-trifluoroethyl)phosphonylmethoxy] ethyl]-6-p-methoxyphenylthiopurine;
2-amino-9-[2-[bis(2,2,2-trifluoroethyl)phosphonylmethoxy] ethyl]-6-m-methoxyphenylthiopurine;
2-amino-9-[2-[bis(2,2,2-trifluoroethyl)phosphonylmethoxy] ethyl]-6-o-methoxyphenylthiopurine; and
2-amino-9-[2-[bis(2,2,2-trifluoroethyl)phosphonylmethoxy] ethyl]-6-p-ethoxyphenylthiopurine.

Other exemplary compounds satisfying the seventh condition include:
2-amino-9-[2-[bis(2,2,2-trifluoroethyl)phosphonylmethoxy] ethyl]-6-m-ethoxyphenylthiopurine; and
2-amino-9-[2-[bis(2,2,2-trifluoroethyl)phosphonylmethoxy] ethyl]-6 -o-ethoxyphenylthiopurine.

The phosphonate nucleotide compounds of the present invention represented by the above formula (I) may exist in the forms of salts, and any salts formed by the aforementioned compounds fall within the scope of the present invention. Examples of such salts include pharmaceutically acceptable salts. For example, where acidic groups exist, the acidic groups may form metal salts such as lithium salt, sodium salt, potassium salt, magnesium salt, or calcium salt, or ammonium salts such as ammonium salt, methylammonium salt, dimethylammonium salt, trimethylammonium salt, or dicyclohexylammonium salt. Where amino groups exist, they may form mineral acid salts such as hydrochloride, hydrobromide, sulfate, nitrate, phosphate, or metaphosphate, or organic acid salts such as methanesulfonate, benzenesulfonate, p-toluenesulfonate, acetate, propionate, tartarate, fumarate, maleate, malate, oxalate, succinate, citrate, benzoate, mandelate, cinnamate, lactate, besilate, valerate, stearate, oleate, lactobionate, ethylsuccinate, semisuccinate, butyrate, parmitate, carbamate, gluconate, laurate, salicylate, laoclate, tannate, or butylsulfonate.

The phosphonate nucleotide compounds of the present invention represented by the above general formula (I) and their salts may exist in the forms of hydrates or solvates. Any hydrates and solvates fall within the scope of the present invention which are formed by the phosphonate nucleotide compounds of the present invention represented by the above general formula (I) including the preferred compound specifically mentioned above. Examples of solvents which can form the solvate include methanol, ethanol, isopropanol, acetone, ethyl acetate, methylene chloride, or diisopropyl ether.

Specific examples of the compounds of the present invention will be listed in Table 1 set out below. In the table, symbols represent: Me-: methyl group; Et-: ethyl group; n-Pr-: normal-propyl group; i-Pr-: isopropyl group; n-Bu: normal-butyl group; i-Bu: isobutyl group; and t-Bu: tertiary-butyl group.

TABLE 1

| No. | $R^1$ | $R^2$ | $R^3$ | $R^4$ | X |
|---|---|---|---|---|---|
| 1 | H | $CF_3CH_2$— | $CF_3CH_2$— | H | C |
| 2 | o-$OCH_3$ | $CF_3CH_2$— | $CF_3CH_2$— | H | C |
| 3 | m-$OCH_3$ | $CF_3CH_2$— | $CF_3CH_2$— | H | C |
| 4 | p-$OCH_3$ | $CF_3CH_2$— | $CF_3CH_2$— | H | C |
| 5 | o-Cl | $CF_3CH_2$— | $CF_3CH_2$— | H | C |
| 6 | m-Cl | $CF_3CH_2$— | $CF_3CH_2$— | H | C |
| 7 | p-Cl | $CF_3CH_2$— | $CF_3CH_2$— | H | C |
| 8 | o-Br | $CF_3CH_2$— | $CF_3CH_2$— | H | C |
| 9 | m-Br | $CF_3CH_2$— | $CF_3CH_2$— | H | C |
| 10 | p-Br | $CF_3CH_2$— | $CF_3CH_2$— | H | C |
| 11 | o-$NH_2$ | $CF_3CH_2$— | $CF_3CH_2$— | H | C |
| 12 | m-$NH_2$ | $CF_3CH_2$— | $CF_3CH_2$— | H | C |
| 13 | p-$NH_2$ | $CF_3CH_2$— | $CF_3CH_2$— | H | C |
| 14 | o-$NO_2$ | $CF_3CH_2$— | $CF_3CH_2$— | H | C |
| 15 | m-$NO_2$ | $CF_3CH_2$— | $CF_3CH_2$— | H | C |
| 16 | p-$NO_2$ | $CF_3CH_2$— | $CF_3CH_2$— | H | C |
| 17 | o-$OC_2H_5$ | $CF_3CH_2$— | $CF_3CH_2$— | H | C |
| 18 | m-$OC_2H_5$ | $CF_3CH_2$— | $CF_3CH_2$— | H | C |
| 19 | p-$OC_2H_5$ | $CF_3CH_2$— | $CF_3CH_2$— | H | C |
| 20 | p-I | $CF_3CH_2$— | $CF_3CH_2$— | H | C |
| 21 | o-O-n-Pr | $CF_3CH_2$— | $CF_3CH_2$— | H | C |
| 22 | m-O-n-Pr | $CF_3CH_2$— | $CF_3CH_2$— | H | C |
| 23 | p-O-n-Pr | $CF_3CH_2$— | $CF_3CH_2$— | H | C |
| 24 | o-O-i-Pr | $CF_3CH_2$— | $CF_3CH_2$— | H | C |
| 25 | m-O-i-Pr | $CF_3CH_2$— | $CF_3CH_2$— | H | C |
| 26 | p-O-i-Pr | $CF_3CH_2$— | $CF_3CH_2$— | H | C |
| 27 | o-O-n-Bu | $CF_3CH_2$— | $CF_3CH_2$— | H | C |

TABLE 1-continued

| No. | R¹ | R² | R³ | R⁴ | X |
|---|---|---|---|---|---|
| 28 | m-O-n-Bu | CF₃CH₂— | CF₃CH₂— | H | C |
| 29 | p-O-n-Bu | CF₃CH₂— | CF₃CH₂— | H | C |
| 30 | o-O-i-Bu | CF₃CH₂— | CF₃CH₂— | H | C |
| 31 | m-O-i-Bu | CF₃CH₂— | CF₃CH₂— | H | C |
| 32 | p-O-i-Bu | CF₃CH₂— | CF₃CH₂— | H | C |
| 33 | o-OCF₃ | CF₃CH₂— | CF₃CH₂— | H | C |
| 34 | m-OCF₃ | CF₃CH₂— | CF₃CH₂— | H | C |
| 35 | p-OCF₃ | CF₃CH₂— | CF₃CH₂— | H | C |
| 36 | H | CF₃CH₂— | CF₃CH₂— | H | N |
| 37 | o-OCH₃ | CF₃CH₂— | CF₃CH₂— | H | N |
| 38 | m-OCH₃ | CF₃CH₂— | CF₃CH₂— | H | N |
| 39 | p-OCH₃ | CF₃CH₂— | CF₃CH₂— | H | N |
| 40 | o-Cl | CF₃CH₂— | CF₃CH₂— | H | N |
| 41 | m-Cl | CF₃CH₂— | CF₃CH₂— | H | N |
| 42 | p-Cl | CF₃CH₂— | CF₃CH₂— | H | N |
| 43 | o-Br | CF₃CH₂— | CF₃CH₂— | H | N |
| 44 | m-Br | CF₃CH₂— | CF₃CH₂— | H | N |
| 45 | p-Br | CF₃CH₂— | CF₃CH₂— | H | N |
| 46 | o-NH₂ | CF₃CH₂— | CF₃CH₂— | H | N |
| 47 | m-NH₂ | CF₃CH₂— | CF₃CH₂— | H | N |
| 48 | p-NH₂ | CF₃CH₂— | CF₃CH₂— | H | N |
| 49 | o-NO₂ | CF₃CH₂— | CF₃CH₂— | H | N |
| 50 | m-NO₂ | CF₃CH₂— | CF₃CH₂— | H | N |
| 51 | p-NO₂ | CF₃CH₂— | CF₃CH₂— | H | N |
| 52 | o-OC₂H₅ | CF₃CH₂— | CF₃CH₂— | H | N |
| 53 | m-OC₂H₅ | CF₃CH₂— | CF₃CH₂— | H | N |
| 54 | p-OC₂H₅ | CF₃CH₂— | CF₃CH₂— | H | N |
| 55 | p-I | CF₃CH₃- | CF₃CH₂— | H | N |
| 56 | o-O-n-Pr | CF₃CH₂— | CF₃CH₂— | H | N |
| 57 | m-O-n-Pr | CF₃CH₂— | CF₃CH₂— | H | N |
| 58 | p-O-n-Pr | CF₃CH₂— | CF₃CH₂— | H | N |
| 59 | o-O-i-Pr | CF₃CH₂— | CF₃CH₂— | H | N |
| 60 | m-O-i-Pr | CF₃CH₂— | CF₃CH₂— | H | |
| 61 | p-O-i-Pr | CF₃CH₂— | CF₃CH₂— | H | N |
| 62 | o-O-n-Bu | CF₃CH₂— | CF₃CH₂— | H | N |
| 63 | m-O-n-Bu | CF₃CH₂— | CF₃CH₂— | H | N |
| 64 | p-O-n-Bu | CF₃CH₂— | CF₃CH₂— | H | N |
| 65 | o-O-i-Bu | CF₃CH₂— | CF₃CH₂— | H | N |
| 66 | m-O-i-Bu | CF₃CH₂— | CF₃CH₂— | H | N |
| 67 | p-O-i-Bu | CF₃CH₂— | CF₃CH₂— | H | N |
| 68 | o-OCF₃ | CF₃CH₂— | CF₃CH₂— | H | N |
| 69 | m-OCF₃ | CF₃CH₂— | CF₃CH₂— | H | N |
| 70 | p-OCF₃ | CF₃CH₂— | CF₃CH₂— | H | N |
| 71 | H | CF₃CH₂— | Me— | H | C |
| 72 | o-OCH₃ | CF₃CH₂— | Me— | H | C |
| 73 | m-OCH₃ | CF₃CH₂— | Me— | H | C |
| 74 | p-OCH₃ | CF₃CH₂— | Me— | H | C |
| 75 | o-Cl | CF₃CH₂— | Me— | H | C |
| 76 | m-Cl | CF₃CH₂— | Me— | H | C |
| 77 | p-Cl | CF₃CH₂— | Me— | H | C |
| 78 | o-Br | CF₃CH₂— | Me— | H | C |
| 79 | m-Br | CF₃CH₂— | Me— | H | C |
| 80 | p-Br | CF₃CH₂— | Me— | H | C |
| 81 | o-NH₂ | CF₃CH₂— | Me— | H | C |
| 82 | m-NH₂ | CF₃CH₂— | Me— | H | C |
| 83 | p-NH₂ | CF₃CH₂— | Me— | H | C |
| 84 | o-NO₂ | CF₃CH₂— | Me— | H | C |
| 85 | m-NO₂ | CF₃CH₂— | Me— | H | C |
| 86 | p-NO₂ | CF₃CH₂— | Me— | H | C |
| 87 | o-OC₂H₅ | CF₃CH₂— | Me— | H | C |
| 88 | m-OC₂H₅ | CF₃CH₂— | Me— | H | C |
| 89 | p-OC₂H₅ | CF₃CH₂— | Me— | H | C |
| 90 | p-I | CF₃CH₂— | Me— | H | C |
| 91 | o-O-n-Pr | CF₃CH₂— | Me— | H | C |
| 92 | m-O-n-Pr | CF₃CH₂— | Me— | H | C |
| 93 | p-O-n-Pr | CF₃CH₂— | Me— | H | C |
| 94 | o-O-i-Pr | CF₃CH₂— | Me— | H | C |
| 95 | m-O-i-Pr | CF₃CH₂— | Me— | H | C |
| 96 | p-O-i-Pr | CF₃CH₂— | Me— | H | C |
| 97 | o-O-n-Bu | CF₃CH₂— | Me— | H | C |
| 98 | m-O-n-Bu | CF₃CH₂— | Me— | H | C |
| 99 | p-O-n-Bu | CF₃CH₂— | Me— | H | C |
| 100 | o-O-i-Bu | CF₃CH₂— | Me— | H | C |
| 101 | m-O-i-Bu | CF₃CH₂— | Me— | H | C |
| 102 | p-O-i-Bu | CF₃CH₂— | Me— | H | C |
| 103 | o-OCF₃ | CF₃CH₂— | Me— | H | C |
| 104 | m-OCF₃ | CF₃CH₂— | Me— | H | C |

TABLE 1-continued

| No. | R¹ | R² | R³ | R⁴ | X |
|---|---|---|---|---|---|
| 105 | p-OCF₃ | CF₃CH₂— | Me— | H | C |
| 106 | H | CF₃CH₂— | Me— | H | N |
| 107 | o-OCH₃ | CF₃CH₂— | Me— | H | N |
| 108 | m-OCH₃ | CF₃CH₂— | Me— | H | N |
| 109 | p-OCH₃ | CF₃CH₂— | Me— | H | N |
| 110 | o-Cl | CF₃CH₂— | Me— | H | N |
| 111 | m-Cl | CF₃CH₂— | Me— | H | N |
| 112 | p-Cl | CF₃CH₂— | Me— | H | N |
| 113 | o-Br | CF₃CH₂— | Me— | H | N |
| 114 | m-Br | CF₃CH₂— | Me— | H | N |
| 115 | p-Br | CF₃CH₂— | Me— | H | N |
| 116 | o-NH₂ | CF₃CH₂— | Me— | H | N |
| 117 | m-NH₂ | CF₃CH₂— | Me— | H | N |
| 118 | p-NH₂ | CF₃CH₂— | Me— | H | N |
| 119 | o-NO₂ | CF₃CH₂— | Me— | H | N |
| 120 | m-NO₂ | CF₃CH₂— | Me— | H | N |
| 121 | p-NO₂ | CF₃CH₂— | Me— | H | N |
| 122 | o-OC₂H₅ | CF₃CH₂— | Me— | H | N |
| 123 | m-OC₂H₅ | CF₃CH₂— | Me— | H | N |
| 124 | p-OC₂H₅ | CF₃CH₂— | Me— | H | N |
| 125 | p-I | CF₃CH₂— | Me— | H | N |
| 126 | o-O-n-Pr | CF₃CH₂— | Me— | H | N |
| 127 | m-O-n-Pr | CF₃CH₂— | Me— | H | N |
| 128 | p-O-n-Pr | CF₃CH₂— | Me— | H | N |
| 129 | o-O-i-Pr | CF₃CH₂— | Me— | H | N |
| 130 | m-O-i-Pr | CF₃CH₂— | Me— | H | N |
| 131 | p-O-i-Pr | CF₃CH₂— | Me— | H | N |
| 132 | o-O-n-Bu | CF₃CH₂— | Me— | H | N |
| 133 | m-O-n-Bu | CF₃CH₂— | Me— | H | N |
| 134 | p-O-n-Bu | CF₃CH₂— | Me— | H | N |
| 135 | o-O-i-Bu | CF₃CH₂— | Me— | H | N |
| 136 | m-O-i-Bu | CF₃CH₂— | Me— | H | N |
| 137 | p-O-i-Bu | CF₃CH₂— | Me— | H | N |
| 138 | o-OCF₃ | CF₃CH₂— | Me— | H | N |
| 139 | m-OCF₃ | CF₃CH₂— | Me— | H | N |
| 140 | p-OCF₃ | CF₃CH₂— | Me— | H | N |
| 141 | H | CF₃CH₂— | Et— | H | C |
| 142 | o-OCH₃ | CF₃CH₂— | Et— | H | C |
| 143 | m-OCH₃ | CF₃CH₂— | Et— | H | C |
| 144 | p-OCH₃ | CF₃CH₂— | Et— | H | C |
| 145 | o-Cl | CF₃CH₂— | Et— | H | C |
| 146 | m-Cl | CF₃CH₂— | Et— | H | C |
| 147 | p-Cl | CF₃CH₂— | Et— | H | C |
| 148 | o-Br | CF₃CH₂— | Et— | H | C |
| 149 | m-Br | CF₃CH₂— | Et— | H | C |
| 150 | p-Br | CF₃CH₂— | Et— | H | C |
| 151 | o-NH₂ | CF₃CH₂— | Et— | H | C |
| 152 | m-NH₂ | CF₃CH₂— | Et— | H | C |
| 153 | p-NH₂ | CF₃CH₂— | Et— | H | C |
| 154 | o-NO₂ | CF₃CH₂— | Et— | H | C |
| 155 | m-NO₂ | CF₃CH₂— | Et— | H | C |
| 156 | p-NO₂ | CF₃CH₂— | Et— | H | C |
| 157 | o-OC₂H₅ | CF₃CH₂— | Et— | H | C |
| 158 | m-OC₂H₅ | CF₃CH₂— | Et— | H | C |
| 159 | p-OC₂H₅ | CF₃CH₂— | Et— | H | C |
| 160 | p-I | CF₃CH₂— | Et— | H | C |
| 161 | o-O-n-Pr | CF₃CH₂— | Et— | H | C |
| 162 | m-O-n-Pr | CF₃CH₂— | Et— | H | C |
| 163 | p-O-n-Pr | CF₃CH₂— | Et— | H | C |
| 164 | o-O-i-Pr | CF₃CH₂— | Et— | H | C |
| 165 | m-O-i-Pr | CF₃CH₂— | Et— | H | C |
| 166 | p-O-i-Pr | CF₃CH₂— | Et— | H | C |
| 167 | o-O-n-Bu | CF₃CH₂— | Et— | H | C |
| 168 | m-O-n-Bu | CF₃CH₂— | Et— | H | C |
| 169 | p-O-n-Bu | CF₃CH₂— | Et— | H | C |
| 170 | o-O-i-Bu | CF₃CH₂— | Et— | H | C |
| 171 | m-O-i-BU | CF₃CH₂— | Et— | H | C |
| 172 | p-O-i-Bu | CF₃CH₂— | Et— | H | C |
| 173 | o-OCF₃ | CF₃CH₂— | Et— | H | C |
| 174 | m-OCF₃ | CF₃CH₂— | Et— | H | C |
| 175 | p-OCF₃ | CF₃CH₂— | Et— | H | C |
| 176 | H | CF₃CH₂— | Et— | H | N |
| 177 | o-OCH₃ | CF₃CH₂— | Et— | H | N |
| 178 | m-OCH₃ | CF₃CH₂— | Et— | H | N |
| 179 | p-OCH₃ | CF₃CH₂— | Et— | H | N |
| 180 | o-Cl | CF₃CH₂— | Et— | H | N |
| 181 | m-Cl | CF₃CH₂— | Et— | H | N |

TABLE 1-continued

| No. | R¹ | R² | R³ | R⁴ | X |
|---|---|---|---|---|---|
| 182 | p-Cl | CF₃CH₂— | Et— | H | N |
| 183 | o-Br | CF₃CH₂— | Et— | H | N |
| 184 | m-Br | CF₃CH₂— | Et— | H | N |
| 185 | p-Br | CF₃CH₂— | Et— | H | N |
| 186 | o-NH₂ | CF₃CH₂— | Et— | H | N |
| 187 | m-NH₂ | CF₃CH₂— | Et— | H | N |
| 188 | p-NH₂ | CF₃CH₂— | Et— | H | N |
| 189 | o-NO₂ | CF₃CH₂— | Et— | H | N |
| 190 | m-NO₂ | CF₃CH₂— | Et— | H | N |
| 191 | p-NO₂ | CF₃CH₂— | Et— | H | N |
| 192 | o-OC₂H₅ | CF₃CH₂— | Et— | H | N |
| 193 | m-OC₂H₅ | CF₃CH₂— | Et— | H | N |
| 194 | p-OC₂H₅ | CF₃CH₂— | Et— | H | N |
| 195 | p-I | CF₃CH₂— | Et— | H | N |
| 196 | o-O-n-Pr | CF₃CH₂— | Et— | H | N |
| 197 | m-O-n-Pr | CF₃CH₂— | Et— | H | N |
| 198 | p-O-n-Pr | CF₃CH₂— | Et— | H | N |
| 199 | o-O-i-Pr | CF₃CH₂— | Et— | H | N |
| 200 | m-O-i-Pr | CF₃CH₂— | Et— | H | N |
| 201 | p-O-i-Pr | CF₃CH₂— | Et— | H | N |
| 202 | o-O-n-Bu | CF₃CH₂— | Et— | H | N |
| 203 | m-O-n-Bu | CF₃CH₂— | Et— | H | N |
| 204 | p-O-n-Bu | CF₃CH₂— | Et— | H | N |
| 205 | o-O-i-Bu | CF₃CH₂— | Et— | H | N |
| 206 | m-O-i-Bu | CF₃CH₂— | Et— | H | N |
| 207 | p-O-i-Bu | CF₃CH₂— | Et— | H | N |
| 208 | o-OCF₃ | CF₃CH₂— | Et— | H | N |
| 209 | m-OCF₃ | CF₃CH₂— | Et— | H | N |
| 210 | p-OCF₃ | CF₃CH₂— | Et— | H | N |
| 211 | H | CF₃CH₂— | H | H | C |
| 212 | o-OCH₃ | CF₃CH₂— | H | H | C |
| 213 | m-OCH₃ | CF₃CH₂— | H | H | C |
| 214 | p-OCH₃ | CF₃CH₂— | H | H | C |
| 215 | o-Cl | CF₃CH₂— | H | H | C |
| 216 | m-Cl | CF₃CH₂— | H | H | C |
| 217 | p-Cl | CF₃CH₂— | H | H | C |
| 218 | o-Br | CF₃CH₂— | H | H | C |
| 219 | m-Br | CF₃CH₂— | H | H | C |
| 220 | p-Br | CF₃CH₂— | H | H | C |
| 221 | o-NH₂ | CF₃CH₂— | H | H | C |
| 222 | m-NH₂ | CF₃CH₂— | H | H | C |
| 223 | p-NH₂ | CF₃CH₂— | H | H | C |
| 224 | o-NO₂ | CF₃CH₂— | H | H | C |
| 225 | m-NO₂ | CF₃CH₂— | H | H | C |
| 226 | p-NO₂ | CF₃CH₂— | H | H | C |
| 227 | o-OC₂H₅ | CF₃CH₂— | H | H | C |
| 228 | m-OC₂H₅ | CF₃CH₂— | H | H | C |
| 229 | p-OC₂H₅ | CF₃CH₂— | H | H | C |
| 230 | p-I | CF₃CH₂— | H | H | C |
| 231 | o-O-n-Pr | CF₃CH₂— | H | H | C |
| 232 | m-O-n-Pr | CF₃CH₂— | H | H | C |
| 233 | p-O-n-Pr | CF₃CH₂— | H | H | C |
| 234 | o-O-i-Pr | CF₃CH₂— | H | H | C |
| 235 | m-O-i-Pr | CF₃CH₂— | H | H | C |
| 236 | p-O-i-Pr | CF₃CH₂— | H | H | C |
| 237 | o-O-n-Bu | CF₃CH₂— | H | H | C |
| 238 | m-O-n-BU | CF₃CH₂— | H | H | C |
| 239 | p-O-n-Bu | CF₃CH₂— | H | H | C |
| 240 | o-O-i-Bu | CF₃CH₂— | H | H | C |
| 241 | m-O-i-Bu | CF₃CH₂— | H | H | C |
| 242 | p-O-i-Bu | CF₃CH₂— | H | H | C |
| 243 | o-OCF₃ | CF₃CH₂— | H | H | C |
| 244 | m-OCF₃ | CF₃CH₂— | H | H | C |
| 245 | p-OCF₃ | CF₃CH₂— | H | H | C |
| 246 | H | CF₃CH₂— | H | H | N |
| 247 | o-OCH₃ | CF₃CH₂— | H | H | N |
| 248 | m-OCH₃ | CF₃CH₂— | H | H | N |
| 249 | p-OCH₃ | CF₃CH₂— | H | H | N |
| 250 | o-Cl | CF₃CH₂— | H | H | N |
| 251 | m-Cl | CF₃CH₂— | H | H | N |
| 252 | p-Cl | CF₃CH₂— | H | H | N |
| 253 | o-Br | CF₃CH₂— | H | H | N |
| 254 | m-Br | CF₃CH₂— | H | H | N |
| 255 | p-Br | CF₃CH₂— | H | H | N |
| 256 | o-NH₂ | CF₃CH₂— | H | H | N |
| 257 | m-NH₂ | CF₃CH₂— | H | H | N |
| 258 | p-NH₂ | CF₃CH₂— | H | H | N |

TABLE 1-continued

| No. | R¹ | R² | R³ | R⁴ | X |
|---|---|---|---|---|---|
| 259 | o-NO₂ | CF₃CH₂— | H | H | N |
| 260 | m-NO₂ | CF₃CH₂— | H | H | N |
| 261 | p-NO₂ | CF₃CH₂— | H | H | N |
| 262 | o-OC₂H₅ | CF₃CH₂— | H | H | N |
| 263 | m-OC₂H₅ | CF₃CH₂— | H | H | N |
| 264 | p-OC₂H₅ | CF₃CH₂— | H | H | N |
| 265 | p-I | CF₃CH₂— | H | H | N |
| 266 | o-O-n-Pr | CF₃CH₂— | H | H | N |
| 267 | m-O-n-Pr | CF₃CH₂— | H | H | N |
| 268 | p-O-n-Pr | CF₃CH₂— | H | H | N |
| 269 | o-O-i-Pr | CF₃CH₂— | H | H | N |
| 270 | m-O-i-Pr | CF₃CH₂— | H | H | N |
| 271 | p-O-i-Pr | CF₃CH₂— | H | H | N |
| 272 | o-O-n-Bu | CF₃CH₂— | H | H | N |
| 273 | m-O-n-Bu | CF₃CH₂— | H | H | N |
| 274 | p-O-n-Bu | CF₃CH₂— | H | H | N |
| 275 | o-O-i-Bu | CF₃CH₂— | H | H | N |
| 276 | m-O-i-Bu | CF₃CH₂— | H | H | N |
| 277 | p-O-i-Bu | CF₃CH₂— | H | H | N |
| 278 | o-OCF₃ | CF₃CH₂— | H | H | N |
| 279 | m-OCF₃ | CF₃CH₂— | H | H | N |
| 280 | p-OCF₃ | CF₃CH₂— | H | H | N |
| 281 | H | H | H | H | C |
| 282 | o-OCH₃ | H | H | H | C |
| 283 | m-OCH₃ | H | H | H | C |
| 284 | p-OCH₃ | H | H | H | C |
| 285 | o-Cl | H | H | H | C |
| 286 | m-Cl | H | H | H | C |
| 287 | p-Cl | H | H | H | C |
| 288 | o-Br | H | H | H | C |
| 289 | m-Br | H | H | H | C |
| 290 | p-Br | H | H | H | C |
| 291 | o-NH₂ | H | H | H | C |
| 292 | m-NH₂ | H | H | H | C |
| 293 | p-NH₂ | H | H | H | C |
| 294 | o-NO₂ | H | H | H | C |
| 295 | m-NO₂ | H | H | H | C |
| 296 | p-NO₂ | H | H | H | C |
| 297 | o-OC₂H₅ | H | H | H | C |
| 298 | m-OC₂H₅ | H | H | H | C |
| 299 | p-OC₂H₅ | H | H | H | C |
| 300 | p-I | H | H | H | C |
| 301 | o-O-n-Pr | H | H | H | C |
| 302 | m-O-n-Pr | H | H | H | C |
| 303 | p-O-n-Pr | H | H | H | C |
| 304 | o-O-i-Pr | H | H | H | C |
| 305 | m-O-i-Pr | H | H | H | C |
| 306 | p-O-i-Pr | H | H | H | C |
| 307 | o-O-n-Bu | H | H | H | C |
| 308 | m-O-n-Bu | H | H | H | C |
| 309 | p-O-n-Bu | H | H | H | C |
| 310 | o-O-i-Bu | H | H | H | C |
| 311 | m-O-i-Bu | H | H | H | C |
| 312 | p-o-i-Bu | H | H | H | C |
| 313 | o-OCF₃ | H | H | H | C |
| 314 | m-OCF₃ | H | H | H | C |
| 315 | p-OCF₃ | H | H | H | C |
| 316 | H | H | H | H | N |
| 317 | o-OCH₃ | H | H | H | N |
| 318 | m-OCH₃ | H | H | H | N |
| 319 | p-OCH₃ | H | H | H | N |
| 320 | o-Cl | H | H | H | N |
| 321 | m-Cl | H | H | H | N |
| 322 | p-Cl | H | H | H | N |
| 323 | o-Br | H | H | H | N |
| 324 | m-Br | H | H | H | N |
| 325 | p-Br | H | H | H | N |
| 326 | o-NH₂ | H | H | H | N |
| 327 | m-NH₂ | H | H | H | N |
| 328 | p-NH₂ | H | H | H | N |
| 329 | o-NO₂ | H | H | H | N |
| 330 | m-NO₂ | H | H | H | N |
| 331 | p-NO₂ | H | H | H | N |
| 332 | o-OC₂H₅ | H | H | H | N |
| 333 | m-OC₂H₅ | H | H | H | N |
| 334 | p-OC₂H₅ | H | H | H | N |
| 335 | p-I | H | H | H | N |

TABLE 1-continued

| No. | R¹ | R² | R³ | R⁴ | X |
|---|---|---|---|---|---|
| 336 | o-O-n-Pr | H | H | H | N |
| 337 | m-O-n-Pr | H | H | H | N |
| 338 | p-O-n-Pr | H | H | H | N |
| 339 | o-O-i-Pr | H | H | H | N |
| 340 | m-O-i-Pr | H | H | H | N |
| 341 | p-O-i-Pr | H | H | H | N |
| 342 | o-O-n-Bu | H | H | H | N |
| 343 | m-O-n-Bu | H | H | H | N |
| 344 | p-O-n-Bu | H | H | H | N |
| 345 | o-O-i-Bu | H | H | H | N |
| 346 | m-O-i-Bu | H | H | H | N |
| 347 | p-O-i-Bu | H | H | H | N |
| 348 | o-OCF$_3$ | H | H | H | N |
| 349 | m-OCF$_3$ | H | H | H | N |
| 350 | p-OCF$_3$ | H | H | H | N |
| 351 | H | CF$_3$CH$_2$— | CF$_3$CH$_2$— | Me— | C |
| 352 | o-OCH$_3$ | CF$_3$CH$_2$— | CF$_3$CH$_2$— | Me— | C |
| 353 | m-OCH$_3$ | CF$_3$CH$_2$— | CF$_3$CH$_2$— | Me— | C |
| 354 | p-OCH$_3$ | CF$_3$CH$_2$— | CF$_3$CH$_2$— | Me— | C |
| 355 | o-Cl | CF$_3$CH$_2$— | CF$_3$CH$_2$— | Me— | C |
| 356 | m-Cl | CF$_3$CH$_2$— | CF$_3$CH$_2$— | Me— | C |
| 357 | p-Cl | CF$_3$CH$_2$— | CF$_3$CH$_2$— | Me— | C |
| 358 | o-Br | CF$_3$CH$_2$— | CF$_3$CH$_2$— | Me— | C |
| 359 | m-Br | CF$_3$CH$_2$— | CF$_3$CH$_2$— | Me— | C |
| 360 | p-Br | CF$_3$CH$_2$— | CF$_3$CH$_2$— | Me— | C |
| 361 | o-NH$_2$ | CF$_3$CH$_2$— | CF$_3$CH$_2$— | Me— | C |
| 362 | m-NH$_2$ | CF$_3$CH$_2$— | CF$_3$CH$_2$— | Me— | C |
| 363 | p-NH$_2$ | CF$_3$CH$_2$— | CF$_3$CH$_2$— | Me— | C |
| 364 | o-NO$_2$ | CF$_3$CH$_2$— | CF$_3$CH$_2$— | Me— | C |
| 365 | m-NO$_2$ | CF$_3$CH$_2$— | CF$_3$CH$_2$— | Me— | C |
| 366 | p-NO$_2$ | CF$_3$CH$_2$— | CF$_3$CH$_2$— | Me— | C |
| 367 | O-OC$_2$H$_5$ | CF$_3$CH$_2$— | CF$_3$CH$_2$— | Me— | C |
| 368 | m-OC$_2$H$_5$ | CF$_3$CH$_2$— | CF$_3$CH$_2$— | Me— | C |
| 369 | p-OC$_2$H$_5$ | CF$_3$CH$_2$— | CF$_3$CH$_2$— | Me— | C |
| 370 | p-I | CF$_3$CH$_2$— | CF$_3$CH$_2$— | Me— | C |
| 371 | o-O-n-Pr | CF$_3$CH$_2$— | CF$_3$CH$_2$— | Me— | C |
| 372 | m-O-n-Pr | CF$_3$CH$_2$— | CF$_3$CH$_2$— | Me— | C |
| 373 | p-O-n-Pr | CF$_3$CH$_2$— | CF$_3$CH$_2$— | Me— | C |
| 374 | o-O-i-Pr | CF$_3$CH$_2$— | CF$_3$CH$_2$— | Me— | C |
| 375 | m-O-i-Pr | CF$_3$CH$_2$— | CF$_3$CH$_2$— | Me— | C |
| 376 | p-O-i-Pr | CF$_3$CH$_2$— | CF$_3$CH$_2$— | Me— | C |
| 377 | o-O-n-Bu | CF$_3$CH$_2$— | CF$_3$CH$_2$— | Me— | C |
| 378 | m-O-n-Bu | CF$_3$CH$_2$— | CF$_3$CH$_2$— | Me— | C |
| 379 | p-O-n-Bu | CF$_3$CH$_2$— | CF$_3$CH$_2$— | Me— | C |
| 380 | o-O-i-Bu | CF$_3$CH$_2$— | CF$_3$CH$_2$— | Me— | C |
| 381 | m-O-i-Bu | CF$_3$CH$_2$— | CF$_3$CH$_2$— | Me— | C |
| 382 | p-O-i-Bu | CF$_3$CH$_2$— | CF$_3$CH$_2$— | Me— | C |
| 383 | o-OCF$_3$ | CF$_3$CH$_2$— | CF$_3$CH$_2$— | Me— | C |
| 384 | m-OCF$_3$ | CF$_3$CH$_2$— | CF$_3$CH$_2$— | Me— | C |
| 385 | p-OCF$_3$ | CF$_3$CH$_2$— | CF$_3$CH$_2$— | Me— | C |
| 386 | H | CF$_3$CH$_2$— | CF$_3$CH$_2$— | Me— | N |
| 387 | o-OCH$_3$ | CF$_3$CH$_2$— | CF$_3$CH$_2$— | Me— | N |
| 388 | m-OCH$_3$ | CF$_3$CH$_2$— | CF$_3$CH$_2$— | Me— | N |
| 389 | p-OCH$_3$ | CF$_3$CH$_2$— | CF$_3$CH$_2$— | Me— | N |
| 390 | o-Cl | CF$_3$CH$_2$— | CF$_3$CH$_2$— | Me— | N |
| 391 | m-Cl | CF$_3$CH$_2$— | CF$_3$CH$_2$— | Me— | N |
| 392 | p-Cl | CF$_3$CH$_2$— | CF$_3$CH$_2$— | Me— | N |
| 393 | o-Br | CF$_3$CH$_2$— | CF$_3$CH$_2$— | Me— | N |
| 394 | m-Br | CF$_3$CH$_2$— | CF$_3$CH$_2$— | Me— | N |
| 395 | p-Br | CF$_3$CH$_2$— | CF$_3$CH$_2$— | Me— | N |
| 396 | o-NH$_2$ | CF$_3$CH$_2$— | CF$_3$CH$_2$— | Me— | N |
| 397 | m-NH$_2$ | CF$_3$CH$_2$— | CF$_3$CH$_2$— | Me— | N |
| 398 | p-NH$_2$ | CF$_3$CH$_2$— | CF$_3$CH$_2$— | Me— | N |
| 399 | o-NO$_2$ | CF$_3$CH$_2$— | CF$_3$CH$_2$— | Me— | N |
| 400 | m-NO$_2$ | CF$_3$CH$_2$— | CF$_3$CH$_2$— | Me— | N |
| 401 | p-NO$_2$ | CF$_3$CH$_2$— | CF$_3$CH$_2$— | Me— | N |
| 402 | o-OC$_2$H$_5$ | CF$_3$CH$_2$— | CF$_3$CH$_2$— | Me— | N |
| 403 | m-OC$_2$H$_5$ | CF$_3$CH$_2$— | CF$_3$CH$_2$— | Me— | N |
| 404 | p-OC$_2$H$_5$ | CF$_3$CH$_2$— | CF$_3$CH$_2$— | Me— | N |
| 405 | p-I | CF$_3$CH$_2$— | CF$_3$CH$_2$— | Me— | N |
| 406 | o-O-n-Pr | CF$_3$CH$_2$— | CF$_3$CH$_2$— | Me— | N |
| 407 | m-O-n-Pr | CF$_3$CH$_2$— | CF$_3$CH$_2$— | Me— | N |
| 408 | p-O-n-Pr | CF$_3$CH$_2$— | CF$_3$CH$_2$— | Me— | N |
| 409 | o-O-i-Pr | CF$_3$CH$_2$— | CF$_3$CH$_2$— | Me— | N |
| 410 | m-O-i-Pr | CF$_3$CH$_2$— | CF$_3$CH$_2$— | Me— | N |
| 411 | p-O-i-Pr | CF$_3$CH$_2$— | CF$_3$CH$_2$— | Me— | N |
| 412 | o-O-n-Bu | CF$_3$CH$_2$— | CF$_3$CH$_2$— | Me— | N |

TABLE 1-continued

| No. | R¹ | R² | R³ | R⁴ | X |
|---|---|---|---|---|---|
| 413 | m-O-n-Bu | CF₃CH₂— | CF₃CH₂— | Me— | N |
| 414 | p-O-n-Bu | CF₃CH₂— | CF₃CH₂— | Me— | N |
| 415 | o-O-i-Eu | CF₃CH₂— | CF₃CH₂— | Me— | N |
| 416 | m-O-i-Bu | CF₃CH₂— | CF₃CH₂— | Me— | N |
| 417 | p-O-i-Bu | CF₃CH₂— | CF₃CH₂— | Me— | N |
| 418 | o-OCF₃ | CF₃CH₂— | CF₃CH₂— | Me— | N |
| 419 | m-OCF₃ | CF₃CH₂— | CF₃CH₂— | Me— | N |
| 420 | p-OCF₃ | CF₃CH₂— | CF₃CH₂— | Me— | N |
| 421 | H | CF₃CH₂— | Me— | Me— | C |
| 422 | o-OCH₃ | CF₃CH₂— | Me— | Me— | C |
| 423 | m-OCH₃ | CF₃CH₂— | Me— | Me— | C |
| 424 | p-OCH₃ | CF₃CH₂— | Me— | Me— | C |
| 425 | o-Cl | CF₃CH₂— | Me— | Me— | C |
| 426 | m-Cl | CF₃CH₂— | Me— | Me— | C |
| 427 | p-Cl | CF₃CH₂— | Me— | Me— | C |
| 428 | o-Br | CF₃CH₂— | Me— | Me— | C |
| 429 | m-Br | CF₃CH₂— | Me— | Me— | C |
| 430 | p-Br | CF₃CH₂— | Me— | Me— | C |
| 431 | o-NH₂ | CF₃CH₂— | Me— | Me— | C |
| 432 | m-NH₂ | CF₃CH₂— | Me— | Me— | C |
| 433 | p-NH₂ | CF₃CH₂— | Me— | Me— | C |
| 434 | o-NO₂ | CF₃CH₂— | Me— | Me— | C |
| 435 | m-NO₂ | CF₃CH₂— | Me— | Me— | C |
| 436 | p-NO₂ | CF₃CH₂— | Me— | Me— | C |
| 437 | o-OC₂H₅ | CF₃CH₂— | Me— | Me— | C |
| 438 | m-OC₂H₅ | CF₃CH₂— | Me— | Me— | C |
| 439 | p-OC₂H₅ | CF₃CH₂— | Me— | Me— | C |
| 440 | p-I | CF₃CH₂— | Me— | Me— | C |
| 441 | o-O-n-Pr | CF₃CH₂— | Me— | Me— | C |
| 442 | m-O-n-Pr | CF₃CH₂— | Me— | Me— | C |
| 443 | p-O-n-Pr | CF₃CH₂— | Me— | Me— | C |
| 444 | o-O-i-Pr | CF₃CH₂— | Me— | Me— | C |
| 445 | m-O-i-Pr | CF₃CH₂— | Me— | Me— | C |
| 446 | p-O-i-Pr | CF₃CH₂— | Me— | Me— | C |
| 447 | o-O-n-Bu | CF₃CH₂— | Me— | Me— | C |
| 448 | m-O-n-Bu | CF₃CH₂— | Me— | Me— | C |
| 449 | p-O-n-Bu | CF₃CH₂— | Me— | Me— | C |
| 450 | o-O-i-Bu | CF₃CH₂— | Me— | Me— | C |
| 451 | m-O-i-Bu | CF₃CH₂— | Me— | Me— | C |
| 452 | p-O-i-Bu | CF₃CH₂— | Me— | Me— | C |
| 453 | o-OCF₃ | CF₃CH₂— | Me— | Me— | C |
| 454 | m-OCF₃ | CF₃CH₂— | Me— | Me— | C |
| 455 | p-OCF₃ | CF₃CH₂— | Me— | Me— | C |
| 456 | H | CF₃CH₂— | Me— | Me— | N |
| 457 | o-OCH₃ | CF₃CH₂— | Me— | Me— | N |
| 458 | m-OCH₃ | CF₃CH₂— | Me— | Me— | N |
| 459 | p-OCH₃ | CF₃CH₂— | Me— | Me— | N |
| 460 | o-Cl | CF₃CH₂— | Me— | Me— | N |
| 461 | m-Cl | CF₃CH₂— | Me— | Me— | N |
| 462 | p-Cl | CF₃CH₂— | Me— | Me— | N |
| 463 | o-Br | CF₃CH₂— | Me— | Me— | N |
| 464 | m-Br | CF₃CH₂— | Me— | Me— | N |
| 465 | p-Br | CF₃CH₂— | Me— | Me— | N |
| 466 | o-NH₂ | CF₃CH₂— | Me— | Me— | N |
| 467 | m-NH₂ | CF₃CH₂— | Me— | Me— | N |
| 468 | p-NH₂ | CF₃CH₂— | Me— | Me— | N |
| 469 | o-NO₂ | CF₃CH₂— | Me— | Me— | N |
| 470 | m-NO₂ | CF₃CH₂— | Me— | Me— | N |
| 471 | p-NO3 | CF₃CH₂— | Me— | Me— | N |
| 472 | o-OC3H5 | CF₃CH₂— | Me— | Me— | N |
| 473 | m-OC₂H₅ | CF₃CH₂— | Me— | Me— | N |
| 474 | p-OC₂H₅ | CF₃CH₂— | Me— | Me— | N |
| 475 | p-I | CF₃CH₂— | Me— | Me— | N |
| 476 | o-O-n-Pr | CF₃CH₂— | Me— | Me— | N |
| 477 | m-O-n-Pr | CF₃CH₃- | Me— | Me— | N |
| 478 | p-O-n-Pr | CF₃CH₂— | Me— | Me— | N |
| 479 | o-O-i-Pr | CF₃CH₂— | Me— | Me— | N |
| 480 | m-O-i-Pr | CF₃CH₂— | Me— | Me— | N |
| 481 | p-O-i-Pr | CF₃CH₂— | Me— | Me— | N |
| 482 | o-O-n-Bu | CF₃CH₂— | Me— | Me— | N |
| 483 | m-O-n-Bu | CF₃CH₂— | Me— | Me— | N |
| 484 | p-O-n-Bu | CF₃CH₂— | Me— | Me— | N |
| 485 | o-O-i-Bu | CF₃CH₂— | Me— | Me— | N |
| 486 | m-O-i-Bu | CF₃CH₂— | Me— | Me— | N |
| 487 | p-O-i-Bu | CF₃CH₂— | Me— | Me— | N |
| 488 | o-OCF₃ | CF₃CH₂— | Me— | Me— | N |
| 489 | m-OCF₃ | CF₃CH₂— | Me— | Me— | N |

TABLE 1-continued

| No. | R¹ | R² | R³ | R⁴ | X |
|---|---|---|---|---|---|
| 490 | p-OCF₃ | CF₃CH₂— | Me— | Me— | N |
| 491 | H | CF₃CH₂— | Et— | Me— | C |
| 492 | o-OCH₃ | CF₃CH₂— | Et— | Me— | C |
| 493 | m-OCH₃ | CF₃CH₂— | Et— | Me— | C |
| 494 | p-OCH₃ | CF₃CH₂— | Et— | Me— | C |
| 495 | o-Cl | CF₃CH₂— | Et— | Me— | C |
| 496 | m-Cl | CF₃CH₂— | Et— | Me— | C |
| 497 | p-Cl | CF₃CH₂— | Et— | Me— | C |
| 498 | o-Br | CF₃CH₂— | Et— | Me— | C |
| 499 | m-Br | CF₃CH₂— | Et— | Me— | C |
| 500 | p-Br | CF₃CH₂— | Et— | Me— | C |
| 501 | o-NH₂ | CF₃CH₂— | Et— | Me— | C |
| 502 | m-NH₂ | CF₃CH₂— | Et— | Me— | C |
| 503 | p-NH₂ | CF₃CH₂— | Et— | Me— | C |
| 504 | o-NO₂ | CF₃CH₂— | Et— | Me— | C |
| 505 | m-NO₂ | CF₃CH₂— | Et— | Me— | C |
| 506 | p-NO₂ | CF₃CH₂— | Et— | Me— | C |
| 507 | o-OC₂H₅ | CF₃CH₂— | Et— | Me— | C |
| 508 | m-OC₂H₅ | CF₃CH₂— | Et— | Me— | C |
| 509 | p-OC₂H₅ | CF₃CH₂— | Et— | Me— | C |
| 510 | p-I | CF₃CH₂— | Et— | Me— | |
| 511 | o-O-n-Pr | CF₃CH₂— | Et— | Me— | C |
| 512 | m-O-n-Pr | CF₃CH₂— | Et— | Me— | C |
| 513 | p-O-n-Pr | CF₃CH₂— | Et— | Me— | C |
| 514 | o-O-i-Pr | CF₃CH₂— | Et— | Me— | C |
| 515 | m-O-i-Pr | CF₃CH₂— | Et— | Me— | C |
| 516 | p-O-i-Pr | CF₃CH₂— | Et— | Me— | C |
| 517 | o-O-n-Bu | CF₃CH₂— | Et— | Me— | C |
| 518 | m-O-n-Bu | CF₃CH₂— | Et— | Me— | C |
| 519 | p-O-n-Bu | CF₃CH₂— | Et— | Me— | C |
| 520 | o-O-i-Bu | CF₃CH₂— | Et— | Me— | C |
| 521 | m-O-i-Bu | CF₃CH₂— | Et— | Me— | C |
| 522 | p-O-i-Bu | CF₃CH₂— | Et— | Me— | C |
| 523 | o-OCF₃ | CF₃CH₂— | Et— | Me— | C |
| 524 | m-OCF₃ | CF₃CH₂— | Et— | Me— | C |
| 525 | p-OCF₃ | CF₃CH₂— | Et— | Me— | C |
| 526 | H | CF₃CH₂— | Et— | Me— | N |
| 527 | o-OCH₃ | CF₃CH₂— | Et— | Me— | N |
| 528 | m-OCH₃ | CF₃CH₂— | Et— | Me— | N |
| 529 | p-OCH₃ | CF₃CH₂— | Et— | Me— | N |
| 530 | o-Cl | CF₃CH₂— | Et— | Me— | N |
| 531 | m-Cl | CF₃CH₂— | Et— | Me— | N |
| 532 | p-Cl | CF₃CH₂— | Et— | Me— | N |
| 533 | O-Br | CF₃CH₂— | Et— | Me— | N |
| 534 | m-Br | CF₃CH₂— | Et— | Me— | N |
| 535 | p-Br | CF₃CH₂— | Et— | Me— | N |
| 536 | o-NH₂ | CF₃CH₂— | Et— | Me— | N |
| 537 | m-NH₂ | CF₃CH₂— | Et— | Me— | N |
| 538 | p-NH₂ | CF₃CH₂— | Et— | Me— | N |
| 539 | o-NO₂ | CF₃CH₂— | Et— | Me— | N |
| 540 | m-NO₂ | CF₃CH₂— | Et— | Me— | N |
| 541 | p-NO₂ | CF₃CH₂— | Et— | Me— | N |
| 542 | o-OC₂H₅ | CF₃CH₂— | Et— | Me— | N |
| 543 | m-OC₂H₅ | CF₃CH₂— | Et— | Me— | N |
| 544 | p-OC₂H₅ | CF₃CH₂— | Et— | Me— | N |
| 545 | p-I | CF₃CH₂— | Et— | Me— | N |
| 546 | o-O-n-Pr | CF₃CH₂— | Et— | Me— | N |
| 547 | m-O-n-Pr | CF₃CH₂— | Et— | Me— | N |
| 548 | p-O-n-Pr | CF₃CH₂— | Et— | Me— | N |
| 549 | o-O-i-Pr | CF₃CH₂— | Et— | Me— | N |
| 550 | m-O-i-Pr | CF₃CH₂— | Et— | Me— | N |
| 551 | p-O-i-Pr | CF₃CH₂— | Et— | Me— | N |
| 552 | o-O-n-Bu | CF₃CH₂— | Et— | Me— | N |
| 553 | m-O-n-Bu | CF₃CH₂— | Et— | Me— | N |
| 554 | p-O-n-Bu | CF₃CH₂— | Et— | Me— | N |
| 555 | o-O-i-Bu | CF₃CH₂— | Et— | Me— | N |
| 556 | m-O-i-Bu | CF₃CH₂— | Et— | Me— | N |
| 557 | p-O-i-Bu | CF₃CH₂— | Et— | Me— | N |
| 558 | o-OCF₃ | CF₃CH₂— | Et— | Me— | N |
| 559 | m-OCF₃ | CF₃CH₂— | Et— | Me— | N |
| 560 | p-OCF₃ | CF₃CH₂— | Et— | Me— | N |
| 561 | H | CF₃CH₂— | H | Me— | C |
| 562 | o-OCH₃ | CF₃CH₂— | H | Me— | C |
| 563 | m-OCH₃ | CF₃CH₂— | H | Me— | C |
| 564 | p-OCH₃ | CF₃CH₂— | H | Me— | C |
| 565 | o-Cl | CF₃CH₂— | H | Me— | C |
| 566 | m-Cl | CF₃CH₂— | H | Me— | C |

TABLE 1-continued

| No. | R¹ | R² | R³ | R⁴ | X |
|---|---|---|---|---|---|
| 567 | p-Cl | CF₃CH₂— | H | Me— | C |
| 568 | o-Br | CF₃CH₂— | H | Me— | C |
| 569 | m-Br | CF₃CH₂— | H | Me— | C |
| 570 | p-Br | CF₃CH₂— | H | Me— | C |
| 571 | o-NH₂ | CF₃CH₂— | H | Me— | C |
| 572 | m-NH₂ | CF₃CH₂— | H | Me— | C |
| 573 | p-NH₂ | CF₃CH₂— | H | Me— | |
| 574 | o-NO₂ | CF₃CH₂— | H | Me— | C |
| 575 | m-NO₂ | CF₃CH₂— | H | Me— | C |
| 576 | p-NO₂ | CF₃CH₂— | H | Me— | C |
| 577 | o-OC₂H₅ | CF₃CH₂— | H | Me— | C |
| 578 | m-OC₂H₅ | CF₃CH₂— | H | Me— | C |
| 579 | p-OC₂H₅ | CF₃CH₂— | H | Me— | C |
| 580 | p-I | CF₃CH₂— | H | Me— | C |
| 581 | o-O-n-Pr | CF₃CH₂— | H | Me— | C |
| 582 | m-O-n-Pr | CF₃CH₂— | H | Me— | C |
| 583 | p-O-n-Pr | CF₃CH₂— | H | Me— | C |
| 584 | o-O-i-Pr | CF₃CH₂— | H | Me— | C |
| 585 | m-O-i-Pr | CF₃CH₂— | H | Me— | C |
| 586 | p-O-i-Pr | CF₃CH₂— | H | Me— | C |
| 587 | o-O-n-Bu | CF₃CH₂— | H | Me— | C |
| 588 | m-O-n-Bu | CF₃CH₂— | H | Me— | C |
| 589 | p-O-n-Bu | CF₃CH₂— | H | Me— | C |
| 590 | o-O-i-Bu | CF₃CH₂— | H | Me— | C |
| 591 | m-O-i-Bu | CF₃CH₂— | H | Me— | C |
| 592 | p-O-i-Bu | CF₃CH₂— | H | Me— | C |
| 593 | o-OCF₃ | CF₃CH₂— | H | Me— | C |
| 594 | m-OCF₃ | CF₃CH₂— | H | Me— | C |
| 595 | p-OCF₃ | CF₃CH₂— | H | Me— | C |
| 596 | H | CF₃CH₂— | H | Me— | N |
| 597 | o-OCH₃ | CF₃CH₂— | H | Me— | N |
| 598 | m-OCH₃ | CF₃CH₂— | H | Me— | N |
| 599 | p-OCH₃ | CF₃CH₂— | H | Me— | N |
| 600 | o-Cl | CF₃CH₂— | H | Me— | N |
| 601 | m-Cl | CF₃CH₂— | H | Me— | N |
| 602 | p-Cl | CF₃CH₂— | H | Me— | N |
| 603 | o-Br | CF₃CH₂— | H | Me— | N |
| 604 | m-Br | CF₃CH₂— | H | Me— | N |
| 605 | p-Br | CF₃CH₂— | H | Me— | N |
| 606 | o-NH₂ | CF₃CH₂— | H | Me— | N |
| 607 | m-NH₂ | CF₃CH₂— | H | Me— | N |
| 608 | p-NH₂ | CF₃CH₂— | H | Me— | N |
| 609 | o-NO₂ | CF₃CH₂— | H | Me— | N |
| 610 | m-NO₂ | CF₃CH₂— | H | Me— | N |
| 611 | p-NO₂ | CF₃CH₂— | H | Me— | N |
| 612 | o-OC₂H₅ | CF₃CH₂— | H | Me— | N |
| 613 | m-OC₂H₅ | CF₃CH₂— | H | Me— | N |
| 614 | p-OC₂H₅ | CF₃CH₂— | H | Me— | N |
| 615 | p-I | CF₃CH₂— | H | Me— | N |
| 616 | o-O-n-Pr | CF₃CH₂— | H | Me— | N |
| 617 | m-O-n-Pr | CF₃CH₂— | H | Me— | N |
| 618 | p-O-n-Pr | CF₃CH₂— | H | Me— | N |
| 619 | o-O-i-Pr | CF₃CH₂— | H | Me— | N |
| 620 | m-O-i-Pr | CF₃CH₂— | H | Me— | N |
| 621 | p-O-i-Pr | CF₃CH₂— | H | Me— | N |
| 622 | o-O-n-Bu | CF₃CH₂— | H | Me— | N |
| 623 | m-O-n-Bu | CF₃CH₂— | H | Me— | N |
| 624 | p-O-n-Bu | CF₃CH₂— | H | Me— | N |
| 625 | o-O-i-Bu | CF₃CH₂— | H | Me— | N |
| 626 | m-O-i-Bu | CF₃CH₂— | H | Me— | N |
| 627 | p-O-i-Bu | CF₃CH₂— | H | Me— | N |
| 628 | o-OCF₃ | CF₃CH₂— | H | Me— | N |
| 629 | m-OCF₃ | CF₃CH₂— | H | Me— | N |
| 630 | p-OCF₃ | CF₃CH₂— | H | Me— | N |
| 631 | H | H | H | Me— | C |
| 632 | o-OCH₃ | H | H | Me— | C |
| 633 | m-OCH₃ | H | H | Me— | C |
| 634 | p-OCH₃ | H | H | Me— | C |
| 635 | o-Cl | H | H | Me— | C |
| 636 | m-Cl | H | H | Me— | C |
| 637 | p-Cl | H | H | Me— | C |
| 638 | o-Br | H | H | Me— | C |
| 639 | m-Br | H | H | Me— | C |
| 640 | p-Br | H | H | Me— | C |
| 641 | o-NH₂ | H | H | Me— | C |
| 642 | m-NH₂ | H | H | Me— | C |
| 643 | p-NH₂ | H | H | Me— | C |

TABLE 1-continued

| No. | R¹ | R² | R³ | R⁴ | X |
|---|---|---|---|---|---|
| 644 | o-NO₂ | H | H | Me— | C |
| 645 | m-NO₂ | H | H | Me— | C |
| 646 | p-NO₂ | H | H | Me— | C |
| 647 | o-OC₂H₅ | H | H | Me— | C |
| 648 | m-OC₂H₅ | H | H | Me— | C |
| 649 | p-OC₂H₅ | H | H | Me— | C |
| 650 | p-I | H | H | Me— | C |
| 651 | o-O-n-Pr | H | H | Me— | C |
| 652 | m-O-n-Pr | H | H | Me— | C |
| 653 | p-O-n-Pr | H | H | Me— | C |
| 654 | o-O-i-Pr | H | H | Me— | C |
| 655 | m-O-i-Pr | H | H | Me— | C |
| 656 | p-O-i-Pr | H | H | Me— | C |
| 657 | o-O-n-Bu | H | H | Me— | C |
| 658 | m-O-n-Bu | H | H | Me— | C |
| 659 | p-O-n-Bu | H | H | Me— | C |
| 660 | o-O-i-Bu | H | H | Me— | C |
| 661 | m-O-i-Bu | H | H | Me— | C |
| 662 | p-O-i-Bu | H | H | Me— | C |
| 663 | o-OCF₃ | H | H | Me— | C |
| 664 | m-OCF₃ | H | H | Me— | C |
| 665 | p-OCF₃ | H | H | Me— | C |
| 666 | H | H | H | Me— | N |
| 667 | o-OCH₃ | H | H | Me— | N |
| 668 | m-OCH₃ | H | H | Me— | N |
| 669 | p-OCH₃ | H | H | Me— | N |
| 670 | o-Cl | H | H | Me— | N |
| 671 | m-Cl | H | H | Me— | N |
| 672 | p-Cl | H | H | Me— | N |
| 673 | o-Br | H | H | Me— | N |
| 674 | m-Br | H | H | Me— | N |
| 675 | p-Br | H | H | Me— | N |
| 676 | o-NH₂ | H | H | Me— | N |
| 677 | m-NH₂ | H | H | Me— | N |
| 678 | p-NH₂ | H | H | Me— | N |
| 679 | o-NO₂ | H | H | Me— | N |
| 680 | m-NO₂ | H | H | Me— | N |
| 681 | p-NO₂ | H | H | Me— | N |
| 682 | o-OC₂H₅ | H | H | Me— | N |
| 683 | m-OC₂H₅ | H | H | Me— | N |
| 684 | p-OC₂H₅ | H | H | Me— | N |
| 685 | p-I | H | H | Me— | N |
| 686 | o-O-n-Pr | H | H | Me— | N |
| 687 | m-O-n-Pr | H | H | Me— | N |
| 688 | p-O-n-Pr | H | H | Me— | N |
| 689 | o-O-i-Pr | H | H | Me— | N |
| 690 | m-O-i-Pr | H | H | Me— | N |
| 691 | p-O-i-Pr | H | H | Me— | N |
| 692 | o-O-n-Bu | H | H | Me— | N |
| 693 | m-O-n-Bu | H | H | Me— | N |
| 694 | p-O-n-Bu | H | H | Me— | N |
| 695 | o-O-i-Bu | H | H | Me— | N |
| 696 | m-O-i-Bu | H | H | Me— | N |
| 697 | p-O-i-Bu | H | H | Me— | N |
| 698 | o-OCF₃ | H | H | Me— | N |
| 699 | m-OCF₃ | H | H | Me— | N |
| 700 | p-OCF₃ | H | H | Me— | N |
| 701 | H | CF₃CH₂— | CF₃CH₂— | —CH₂F | C |
| 702 | o-OCH₃ | CF₃CH₂— | CF₃CH₂— | —CH₂F | C |
| 703 | m-OCH₃ | CF₃CH₂— | CF₃CH₂— | —CH₂F | C |
| 704 | p-OCH₃ | CF₃CH₂— | CF₃CH₂— | —CH₂F | C |
| 705 | o-Cl | CF₃CH₂— | CF₃CH₂— | —CH₂F | C |
| 706 | m-Cl | CF₃CH₂— | CF₃CH₂— | —CH₂F | C |
| 707 | p-Cl | CF₃CH₂— | CF₃CH₂— | —CH₂F | C |
| 708 | o-Br | CF₃CH₂— | CF₃CH₂— | —CH₂F | C |
| 709 | m-Br | CF₃CH₂— | CF₃CH₂— | —CH₂F | C |
| 710 | p-Br | CF₃CH₂— | CF₃CH₂— | —CH₂F | C |
| 711 | o-NH₂ | CF₃CH₂— | CF₃CH₂— | —CH₂F | C |
| 712 | m-NH₂ | CF₃CH₂— | CF₃CH₂— | —CH₂F | C |
| 713 | p-NH₂ | CF₃CH₂— | CF₃CH₂— | —CH₂F | C |
| 714 | o-NO₂ | CF₃CH₂— | CF₃CH₂— | —CH₂F | C |
| 715 | m-NO₂ | CF₃CH₂— | CF₃CH₂— | —CH₂F | C |
| 716 | p-NO₂ | CF₃CH₂— | CF₃CH₂— | —CH₂F | C |
| 717 | o-OC₂H₅ | CF₃CH₂— | CF₃CH₂— | —CH₂F | C |
| 718 | m-OC₂H₅ | CF₃CH₂— | CF₃CH₂— | —CH₂F | C |
| 719 | p-OC₂H₅ | CF₃CH₂— | CF₃CH₂— | —CH₂F | C |
| 720 | p-I | CF₃CH₂— | CF₃CH₂— | —CH₂F | C |

TABLE 1-continued

| No. | R¹ | R² | R³ | R⁴ | X |
|---|---|---|---|---|---|
| 721 | o-O-n-Pr | CF₃CH₂— | CF₃CH₂— | —CH₂F | C |
| 722 | m-O-n-Fr | CF₃CH₂— | CF₃CH₂— | —CH₂F | C |
| 723 | p-O-n-Pr | CF₃CH₂— | CF₃CH₂— | —CH₂F | C |
| 724 | o-O-i-Pr | CF₃CH₂— | CF₃CH₂— | —CH₂F | C |
| 725 | m-O-i-Pr | CF₃CH₂— | CF₃CH₂— | —CH₂F | C |
| 726 | p-O-i-Pr | CF₃CH₂— | CF₃CH₂— | —CH₂F | C |
| 727 | o-O-n-Bu | CF₃CH₂— | CF₃CH₂— | —CH₂F | C |
| 728 | m-O-n-Bu | CF₃CH₂— | CF₃CH₂— | —CH₂F | C |
| 729 | p-O-n-Bu | CF₃CH₂— | CF₃CH₂— | —CH₂F | C |
| 730 | o-O-i-Bu | CF₃CH₂— | CF₃CH₂— | —CH₂F | C |
| 731 | m-O-i-Bu | CF₃CH₂— | CF₃CH₂— | —CH₂F | C |
| 732 | p-O-i-Bu | CF₃CH₂— | CF₃CH₂— | —CH₂F | C |
| 733 | o-OCF₃ | CF₃CH₂— | CF₃CH₂— | —CH₂F | C |
| 734 | m-OCF₃ | CF₃CH₂— | CF₃CH₂— | —CH₂F | C |
| 735 | p-OCF₃ | CF₃CH₂— | CF₃CH₂— | —CH₂F | C |
| 736 | H | CF₃CH₂— | CF₃CH₂— | —CH₂F | N |
| 737 | o-OCH₃ | CF₃CH₂— | CF₃CH₂— | —CH₂F | N |
| 738 | m-OCH₃ | CF₃CH₂— | CF₃CH₂— | —CH₂F | N |
| 739 | p-OCH₃ | CF₃CH₂— | CF₃CH₂— | —CH₂F | N |
| 740 | o-Cl | CF₃CH₂— | CF₃CH₂— | —CH₂F | N |
| 741 | m-Cl | CF₃CH₂— | CF₃CH₂— | —CH₂F | N |
| 742 | p-Cl | CF₃CH₂— | CF₃CH₂— | —CH₂F | N |
| 743 | o-Br | CF₃CH₂— | CF₃CH₂— | —CH₂F | N |
| 744 | m-Br | CF₃CH₂— | CF₃CH₂— | —CH₂F | N |
| 745 | p-Br | CF₃CH₂— | CF₃CH₂— | —CH₂F | N |
| 746 | o-NH₂ | CF₃CH₂— | CF₃CH₂— | —CH₂F | N |
| 747 | m-NH₂ | CF₃CH₂— | CF₃CH₂— | —CH₂F | N |
| 748 | p-NH₂ | CF₃CH₂— | CF₃CH₂— | —CH₂F | N |
| 749 | o-NO₂ | CF₃CH₂— | CF₃CH₂— | —CH₂F | N |
| 750 | m-NO₂ | CF₃CH₂— | CF₃CH₂— | —CH₂F | N |
| 751 | p-NO₂ | CF₃CH₂— | CF₃CH₂— | —CH₂F | N |
| 752 | o-OC₂H₅ | CF₃CH₂— | CF₃CH₂— | —CH₂F | N |
| 753 | m-OC₂H₅ | CF₃CH₂— | CF₃CH₂— | —CH₂F | N |
| 754 | p-OC₂H₅ | CF₃CH₂— | CF₃CH₂— | —CH₂F | N |
| 755 | p-I | CF₃CH₂— | CF₃CH₂— | —CH₂F | N |
| 756 | o-O-n-Pr | CF₃CH₂— | CF₃CH₂— | —CH₂F | N |
| 757 | m-O-n-Pr | CF₃CH₂— | CF₃CH₂— | —CH₂F | N |
| 758 | p-O-n-Pr | CF₃CH₂— | CF₃CH₂— | —CH₂F | N |
| 759 | o-O-i-Pr | CF₃CH₂— | CF₃CH₂— | —CH₂F | N |
| 760 | m-O-i-Pr | CF₃CH₂— | CF₃CH₂— | —CH₂F | N |
| 761 | p-O-i-Pr | CF₃CH₂— | CF₃CH₂— | —CH₂F | N |
| 762 | o-O-n-Bu | CF₃CH₂— | CF₃CH₂— | —CH₂F | N |
| 763 | m-O-n-Bu | CF₃CH₂— | CF₃CH₂— | —CH₂F | N |
| 764 | p-O-n-Bu | CF₃CH₂— | CF₃CH₂— | —CH₂F | N |
| 765 | o-O-i-Bu | CF₃CH₂— | CF₃CH₂— | —CH₂F | N |
| 766 | m-O-i-Bu | CF₃CH₂— | CF₃CH₂— | —CH₂F | N |
| 767 | p-O-i-Bu | CF₃CH₂— | CF₃CH₂— | —CH₂F | N |
| 768 | o-OCF₃ | CF₃CH₂— | CF₃CH₂— | —CH₂F | N |
| 769 | m-OCF₃ | CF₃CH₂— | CF₃CH₂— | —CH₂F | N |
| 770 | p-OCF₃ | CF₃CH₂— | CF₃CH₂— | —CH₂F | N |
| 771 | H | CF₃CH₂— | Me— | —CH₂F | C |
| 772 | o-OCH₃ | CF₃CH₂— | Me— | —CH₂F | C |
| 773 | m-OCH₃ | CF₃CH₂— | Me— | —CH₂F | C |
| 774 | p-OCH₃ | CF₃CH₂— | Me— | —CH₂F | C |
| 775 | o-Cl | CF₃CH₂— | Me— | —CH₂F | C |
| 776 | m-Cl | CF₃CH₂— | Me— | —CH₂F | C |
| 777 | p-Cl | CF₃CH₂— | Me— | —CH₂F | C |
| 778 | o-Br | CF₃CH₂— | Me— | —CH₂F | C |
| 779 | m-Br | CF₃CH₂— | Me— | —CH₂F | C |
| 780 | p-Br | CF₃CH₂— | Me— | —CH₂F | C |
| 781 | o-NH₂ | CF₃CH₂— | Me— | —CH₂F | C |
| 782 | m-NH₂ | CF₃CH₂— | Me— | —CH₂F | C |
| 783 | p-NH₂ | CF₃CH₂— | Me— | —CH₂F | C |
| 784 | o-NO₂ | CF₃CH₂— | Me— | —CH₂F | C |
| 785 | m-NO₂ | CF₃CH₂— | Me— | —CH₂F | C |
| 786 | p-NO₂ | CF₃CH₂— | Me— | —CH₂F | C |
| 787 | o-OC₂H₅ | CF₃CH₂— | Me— | —CH₂F | C |
| 788 | m-OC₂H₅ | CF₃CH₂— | Me— | —CH₂F | C |
| 789 | p-OC₂H₅ | CF₃CH₂— | Me— | —CH₂F | C |
| 790 | p-I | CF₃CH₂— | Me— | —CH₂F | C |
| 791 | o-O-n-Pr | CF₃CH₂— | Me— | —CH₂F | C |
| 792 | m-O-n-Pr | CF₃CH₂— | Me— | —CH₂F | C |
| 793 | p-O-n-Pr | CF₃CH₂— | Me— | —CH₂F | C |
| 794 | o-O-i-Pr | CF₃CH₂— | Me— | —CH₂F | C |
| 795 | m-O-i-Pr | CF₃CH₂— | Me— | —CH₂F | C |
| 796 | p-O-i-Pr | CF₃CH₂— | Me— | —CH₂F | C |
| 797 | o-O-n-Bu | CF₃CH₂— | Me— | —CH₂F | C |

TABLE 1-continued

| No. | R¹ | R² | R³ | R⁴ | X |
|---|---|---|---|---|---|
| 798 | m-O-n-Bu | CF$_3$CH$_2$— | Me— | —CH$_2$F | C |
| 799 | p-O-n-Bu | CF$_3$CH$_2$— | Me— | —CH$_2$F | C |
| 800 | o-O-i-Bu | CF$_3$CH$_2$— | Me— | —CH$_2$F | C |
| 801 | m-O-i-Bu | CF$_3$CH$_2$— | Me— | —CH$_2$F | C |
| 802 | p-O-i-Bu | CF$_3$CH$_2$— | Me— | —CH$_2$F | C |
| 803 | o-OCF$_3$ | CF$_3$CH$_2$— | Me— | —CH$_2$F | C |
| 804 | m-OCF$_3$ | CF$_3$CH$_2$— | Me— | —CH$_2$F | C |
| 805 | p-OCF$_3$ | CF$_3$CH$_2$— | Me— | —CH$_2$F | C |
| 806 | H | CF$_3$CH$_2$— | Me— | —CH$_2$F | N |
| 807 | o-OCH$_3$ | CF$_3$CH$_2$— | Me— | —CH$_2$F | N |
| 808 | m-OCH$_3$ | CF$_3$CH$_2$— | Me— | —CH$_2$F | N |
| 809 | p-OCH$_3$ | CF$_3$CH$_2$— | Me— | —CH$_2$F | N |
| 810 | o-Cl | CF$_3$CH$_2$— | Me— | —CH$_2$F | N |
| 811 | m-Cl | CF$_3$CH$_2$— | Me— | —CH$_2$F | N |
| 812 | p-Cl | CF$_3$CH$_2$— | Me— | —CH$_2$F | N |
| 813 | o-Br | CF$_3$CH$_2$— | Me— | —CH$_2$F | N |
| 814 | m-Br | CF$_3$CH$_2$— | Me— | —CH$_2$F | N |
| 815 | p-Br | CF$_3$CH$_2$— | Me— | —CH$_2$F | N |
| 816 | o-NH$_2$ | CF$_3$CH$_2$— | Me— | —CH$_2$F | N |
| 817 | m-NH$_2$ | CF$_3$CH$_2$— | Me— | —CH$_2$F | N |
| 818 | p-NH$_2$ | CF$_3$CH$_2$— | Me— | —CH$_2$F | N |
| 819 | o-NO$_2$ | CF$_3$CH$_2$— | Me— | —CH$_2$F | N |
| 820 | m-NO$_2$ | CF$_3$CH$_2$— | Me— | —CH$_2$F | N |
| 821 | p-NO$_2$ | CF$_3$CH$_2$— | Me— | —CH$_2$F | N |
| 822 | o-OC$_2$H$_5$ | CF$_3$CH$_2$— | Me— | —CH$_2$F | N |
| 823 | m-OC$_2$H$_5$ | CF$_3$CH$_2$— | Me— | —CH$_2$F | N |
| 824 | p-OC$_2$H$_5$ | CF$_3$CH$_2$— | Me— | —CH$_2$F | N |
| 825 | p-I | CF$_3$CH$_2$— | Me— | —CH$_2$F | N |
| 826 | o-O-n-Pr | CF$_3$CH$_2$— | Me— | —CH$_2$F | N |
| 827 | m-O-n-Pr | CF$_3$CH$_2$— | Me— | —CH$_2$F | N |
| 828 | p-O-n-Pr | CF$_3$CH$_2$— | Me— | —CH$_2$F | N |
| 829 | o-O-i-Pr | CF$_3$CH$_2$— | Me— | —CH$_2$F | N |
| 830 | m-O-i-Pr | CF$_3$CH$_2$— | Me— | —CH$_2$F | N |
| 831 | p-O-i-Pr | CF$_3$CH$_2$— | Me— | —CH$_2$F | N |
| 832 | o-O-n-Du | CF$_3$CH$_2$— | Me— | —CH$_2$F | N |
| 833 | m-O-n-Bu | CF$_3$CH$_2$— | Me— | —CH$_2$F | N |
| 834 | p-O-n-Bu | CF$_3$CH$_2$— | Me— | —CH$_2$F | N |
| 835 | o-O-i-Bu | CF$_3$CH$_2$— | Me— | —CH$_2$F | N |
| 836 | m-O-i-Bu | CF$_3$CH$_2$— | Me— | —CH$_2$F | N |
| 837 | p-O-i-Bu | CF$_3$CH$_2$— | Me— | —CH$_2$F | N |
| 838 | o-OCF$_3$ | CF$_3$CH$_2$— | Me— | —CH$_2$F | N |
| 839 | m-OCF$_3$ | CF$_3$CH$_2$— | Me— | —CH$_2$F | N |
| 840 | p-OCF$_3$ | CF$_3$CH$_2$— | Me— | —CH$_2$F | N |
| 841 | H | F3CH$_2$— | Et— | —CH$_2$F | C |
| 842 | o-OCH$_3$ | CF$_3$CH$_2$— | Et— | —CH$_2$F | C |
| 843 | m-OCH$_3$ | CF$_3$CH$_2$— | Et— | —CH$_2$F | C |
| 844 | p-OCH$_3$ | CF$_3$CH$_2$— | Et— | —CH$_2$F | C |
| 845 | o-Cl | CF$_3$CH$_2$— | Et— | —CH$_2$F | C |
| 846 | m-Cl | CF$_3$CH$_2$— | Et— | —CH$_2$F | C |
| 847 | p-Cl | CF$_3$CH$_2$— | Et— | —CH$_2$F | C |
| 848 | o-Br | CF$_3$CH$_2$— | Et— | —CH$_2$F | C |
| 849 | m-Br | CF$_3$CH$_2$— | Et— | —CH$_2$F | C |
| 850 | p-Br | CF$_3$CH$_2$— | Et— | —CH$_2$F | C |
| 851 | o-NH$_2$ | CF$_3$CH$_2$— | Et— | —CH$_2$F | C |
| 852 | m-NH$_2$ | CF$_3$CH$_2$— | Et— | —CH$_2$F | C |
| 853 | p-NH$_2$ | CF$_3$CH$_2$— | Et— | —CH$_2$F | C |
| 854 | o-NO$_2$ | CF$_3$CH$_2$— | Et— | —CH$_2$F | C |
| 855 | m-NO$_2$ | CF$_3$CH$_2$— | Et— | —CH$_2$F | C |
| 856 | p-NO$_2$ | CF$_3$CH$_2$— | Et— | —CH$_2$F | C |
| 857 | o-OC$_2$H$_5$ | CF$_3$CH$_2$— | Et— | —CH$_2$F | C |
| 858 | m-OC$_2$H$_5$ | CF$_3$CH$_2$— | Et— | —CH$_2$F | C |
| 859 | p-OC$_2$H$_5$ | CF$_3$CH$_2$— | Et— | —CH$_2$F | C |
| 860 | p-I | CF$_3$CH$_2$— | Et— | —CH$_2$F | C |
| 861 | o-O-n-Pr | CF$_3$CH$_2$— | Et— | —CH$_2$F | C |
| 862 | m-O-n-Pr | CF$_3$CH$_2$— | Et— | —CH$_2$F | C |
| 863 | p-O-n-Pr | CF$_3$CH$_2$— | Et— | —CH$_2$F | C |
| 864 | o-O-i-Pr | CF$_3$CH$_2$— | Et— | —CH$_2$F | C |
| 865 | m-O-i-Pr | CF$_3$CH$_2$— | Et— | —CH$_2$F | C |
| 866 | p-O-i-Pr | CF$_3$CH$_2$— | Et— | —CH$_2$F | C |
| 867 | o-O-n-Bu | CF$_3$CH$_2$— | Et— | —CH$_2$F | C |
| 868 | m-O-n-Bu | CF$_3$CH$_2$— | Et— | —CH$_2$F | C |
| 869 | p-O-n-Bu | CF$_3$CH$_2$— | Et— | —CH$_2$F | C |
| 870 | o-O-i-Bu | CF$_3$CH$_2$— | Et— | —CH$_2$F | C |
| 871 | m-O-i-Bu | CF$_3$CH$_2$— | Et— | —CH$_2$F | C |
| 872 | p-O-i-Bu | CF$_3$CH$_2$— | Et— | —CH$_2$F | C |
| 873 | o-OCF$_3$ | CF$_3$CH$_2$— | Et— | —CH$_2$F | C |
| 874 | m-OCF$_3$ | CF$_3$CH$_2$— | Et— | —CH$_2$F | C |

TABLE 1-continued

| No. | R¹ | R² | R³ | R⁴ | X |
|---|---|---|---|---|---|
| 875 | p-OCF₃ | CF₃CH₂— | Et— | —CH₂F | C |
| 876 | H | CF₃CH₂— | Et— | —CH₂F | N |
| 877 | o-OCH₃ | CF₃CH₂— | Et— | —CH₂F | N |
| 878 | m-OCH₃ | CF₃CH₂— | Et— | —CH₂F | N |
| 879 | p-OCH₃ | CF₃CH₂— | Et— | —CH₂F | N |
| 880 | o-Cl | CF₃CH₂— | Et— | —CH₂F | N |
| 881 | m-Cl | CF₃CH₂— | Et— | —CH₂F | N |
| 882 | p-CJ | CF₃CH₂— | Et— | —CH₂F | N |
| 883 | o-Br | CF₃CH₂— | Et— | —CH₂F | N |
| 884 | m-Br | CF₃CH₂— | Et— | —CH₂F | N |
| 885 | p-Br | CF₃CH₂— | Et— | —CH₂F | N |
| 886 | o-NH₂ | CF₃CH₂— | Et— | —CH₂F | N |
| 887 | m-NH₂ | CF₃CH₂— | Et— | —CH₂F | N |
| 888 | p-NH₂ | CF₃CH₂— | Et— | —CH₂F | N |
| 889 | o-NO₂ | CF₃CH₂— | Et— | —CH₂F | N |
| 890 | m-NO₂ | CF₃CH₂— | Et— | —CH₂F | N |
| 891 | p-NO₂ | CF₃CH₂— | Et— | —CH₂F | N |
| 892 | o-OC₂H₅ | CF₃CH₂— | Et— | —CH₂F | N |
| 893 | m-OC₂H₅ | CF₃CH₂— | Et— | —CH₂F | N |
| 894 | p-OC₂H₅ | CF₃CH₂— | Et— | —CH₂F | N |
| 895 | p-I | CF₃CH₂— | Et— | —CH₂F | N |
| 896 | o-O-n-Pr | CF₃CH₂— | Et— | —CH₂F | N |
| 897 | m-O-n-Pr | CF₃CH₂— | Et— | —CH₂F | N |
| 898 | p-O-n-Pr | CF₃CH₂— | Et— | —CH₂F | N |
| 899 | o-O-i-Pr | CF₃CH₂— | Et— | —CH₂F | N |
| 900 | m-O-i-Pr | CF₃CH₂— | Et— | —CH₂F | N |
| 901 | p-O-i-Pr | CF₃CH₂— | Et— | —CH₂F | N |
| 902 | o-O-n-Bu | CF₃CH₂— | Et— | —CH₂F | N |
| 903 | m-O-n-Bu | CF₃CH₂— | Et— | —CH₂F | N |
| 904 | p-O-n-Bu | CF₃CH₂— | Et— | —CH₂F | N |
| 905 | o-O-i-Bu | CF₃CH₂— | Et— | —CH₂F | N |
| 906 | m-O-i-Bu | CF₃CH₂— | Et— | —CH₂F | N |
| 907 | p-O-i-Bu | CF₃CH₂— | Et— | —CH₂F | N |
| 908 | o-OCF₃ | CF₃CH₂— | Et— | —CH₂F | N |
| 909 | m-OCF₃ | CF₃CH₂— | Et— | —CH₂F | N |
| 910 | p-OCF₃ | CF₃CH₂— | Et— | —CH₂F | N |
| 911 | H | CF₃CH₂— | H | —CH₂F | C |
| 912 | o-OCH₃ | CF₃CH₂— | H | —CH₂F | C |
| 913 | m-OCH₃ | CF₃CH₂— | H | —CH₂F | C |
| 914 | p-OCH₃ | CF₃CH₂— | H | —CH₂F | C |
| 915 | o-Cl | CF₃CH₂— | H | —CH₂F | C |
| 916 | m-Cl | CF₃CH₂— | H | —CH₂F | C |
| 917 | p-Cl | CF₃CH₂— | H | —CH₂F | C |
| 918 | o-Br | CF₃CH₂— | H | —CH₂F | C |
| 919 | m-Br | CF₃CH₂— | H | —CH₂F | C |
| 920 | p-Br | CF₃CH₂— | H | —CH₂F | C |
| 921 | o-NH₂ | CF₃CH₂— | H | —CH₂F | C |
| 922 | m-NH₂ | CF₃CH₂— | H | —CH₂F | C |
| 923 | p-NH₂ | CF₃CH₂— | H | —CH₂F | C |
| 924 | o-NO₂ | CF₃CH₂— | H | —CH₂F | C |
| 925 | m-NO₂ | CF₃CH₂— | H | —CH₂F | C |
| 926 | p-NO₂ | CF₃CH₂— | H | —CH₂F | C |
| 927 | o-OC₂H₅ | CF₃CH₂— | H | —CH₂F | C |
| 928 | m-OC₂H₅ | CF₃CH₂— | H | —CH₂F | C |
| 929 | p-OC₂H₅ | CF₃CH₂— | H | —CH₂F | C |
| 930 | p-I | CF₃CH₂— | H | —CH₂F | C |
| 931 | o-O-n-Pr | CF₃CH₂— | H | —CH₂F | C |
| 932 | m-O-n-Pr | CF₃CH₂— | H | —CH₂F | C |
| 933 | p-O-n-Pr | CF₃CH₂— | H | —CH₂F | C |
| 934 | o-O-i-Pr | CF₃CH₂— | H | —CH₂F | C |
| 935 | m-O-i-Pr | CF₃CH₂— | H | —CH₂F | C |
| 936 | p-O-i-Pr | CF₃CH₂— | H | —CH₂F | C |
| 937 | o-O-n-Bu | CF₃CH₂— | H | —CH₂F | C |
| 938 | m-O-n-Bu | CF₃CH₂— | H | —CH₂F | C |
| 939 | p-O-n-Bu | CF₃CH₂— | H | —CH₂F | C |
| 940 | o-O-i-Bu | CF₃CH₂— | H | —CH₂F | C |
| 941 | m-O-i-Bu | CF₃CH₂— | H | —CH₂F | C |
| 942 | p-O-i-Bu | CF₃CH₂— | H | —CH₂F | C |
| 943 | o-OCF₃ | CF₃CH₂— | H | —CH₂F | C |
| 944 | m-OCF₃ | CF₃CH₂— | H | —CH₂F | C |
| 945 | p-OCF₃ | CF₃CH₂— | H | —CH₂F | C |
| 946 | H | CF₃CH₂— | H | —CH₂F | N |
| 947 | o-OCH₃ | CF₃CH₂— | H | —CH₂F | N |
| 948 | m-OCH₃ | CF₃CH2 | H | —CH₂F | N |
| 949 | p-OCH₃ | CF₃CH₂— | H | —CH₂F | N |
| 950 | o-Cl | CF₃CH₂— | H | —CH₂F | N |
| 951 | m-Cl | CF₃CH₂— | H | —CH₂F | N |

TABLE 1-continued

| No. | R¹ | R² | R³ | R⁴ | X |
|---|---|---|---|---|---|
| 952 | p-Cl | CF₃CH₂— | H | —CH₂F | N |
| 953 | o-Br | CF₃CH₂— | H | —CH₂F | N |
| 954 | m-Br | CF₃CH₂— | H | —CH₂F | N |
| 955 | p-Br | CF₃CH₂— | H | —CH₂F | N |
| 956 | o-NH₂ | CF₃CH₂— | H | —CH₂F | N |
| 957 | m-NH₂ | CF₃CH₂— | H | —CH₂F | N |
| 958 | p-NH₂ | CF₃CH₂— | H | —CH₂F | N |
| 959 | o-NO₂ | CF₃CH₂— | H | —CH₂F | N |
| 960 | m-NO₂ | CF₃CH₂— | H | —CH₂F | N |
| 961 | p-NO₂ | CF₃CH₂— | H | —CH₂F | N |
| 962 | o-OC₂H₅ | CF₃CH₂— | H | —CH₂F | N |
| 963 | m-OC₂H₅ | CF₃CH₂— | H | —CH₂F | N |
| 964 | p-OC₂H₅ | CF₃CH₂— | H | —CH₂F | N |
| 965 | p-I | CF₃CH₂— | H | —CH₂F | N |
| 966 | o-O-n-Pr | CF₃CH₂— | H | —CH₂F | N |
| 967 | m-O-n-Pr | CF₃CH₂— | H | —CH₂F | N |
| 968 | p-O-n-Pr | CF₃CH₂— | H | —CH₂F | N |
| 969 | o-O-i-Pr | CF₃CH₂— | H | —CH₂F | N |
| 970 | m-O-i-Pr | CF₃CH₂— | H | —CH₂F | N |
| 971 | p-O-i-Pr | CF₃CH₂— | H | —CH₂F | N |
| 972 | o-O-n-Bu | CF₃CH₂— | H | —CH₂F | N |
| 973 | m-O-n-Bu | CF₃CH₂— | H | —CH₂F | N |
| 974 | p-O-n-Bu | CF₃CH₂— | H | —CH₂F | N |
| 975 | o-O-i-Bu | CF₃CH₂— | H | —CH₂F | N |
| 976 | m-O-i-Bu | CF₃CH₂— | H | —CH₂F | N |
| 977 | p-O-i-Bu | CF₃CH₂— | H | —CH₂F | N |
| 978 | o-OCF₃ | CF₃CH₂— | H | —CH₂F | N |
| 979 | m-OCF₃ | CF₃CH₂— | H | —CH₂F | N |
| 980 | p-OCF₃ | CF₃CH₂— | H | —CH₂F | N |
| 981 | H | H | H | —CH₂F | C |
| 982 | o-OCH₃ | H | H | —CH₂F | C |
| 983 | m-OCH₃ | H | H | —CH₂F | C |
| 984 | p-OCH₃ | H | H | —CH₂F | C |
| 985 | o-Cl | H | H | —CH₂F | C |
| 986 | m-Cl | H | H | —CH₂F | C |
| 987 | p-Cl | H | H | —CH₂F | C |
| 988 | o-Br | H | H | —CH₂F | C |
| 989 | m-Br | H | H | —CH₂F | C |
| 990 | p-Br | H | H | —CH₂F | C |
| 991 | o-NH₂ | H | H | —CH₂F | C |
| 992 | m-NH₂ | H | H | —CH₂F | C |
| 993 | p-NH₂ | H | H | —CH₂F | C |
| 994 | o-NO₂ | H | H | —CH₂F | C |
| 995 | m-NO₂ | H | H | —CH₂F | C |
| 996 | p-NO₂ | H | H | —CH₂F | C |
| 997 | o-OC₂H₅ | H | H | —CH₂F | C |
| 998 | m-OC₂H₅ | H | H | —CH₂F | C |
| 999 | p-OC₂H₅ | H | H | —CH₂F | C |
| 1000 | p-I | H | H | —CH₂F | C |
| 1001 | o-O-n-Pr | H | H | —CH₂F | C |
| 1002 | m-O-n-Pr | H | H | —CH₂F | C |
| 1003 | p-O-n-Pr | H | H | —CH₂F | C |
| 1004 | o-O-i-Pr | H | H | —CH₂F | C |
| 1005 | m-O-i-Pr | H | H | —CH₂F | C |
| 1006 | p-O-i-Pr | H | H | —CH₂F | C |
| 1007 | o-O-n-Bu | H | H | —CH₂F | C |
| 1008 | m-O-n-Bu | H | H | —CH₂F | C |
| 1009 | p-O-n-Bu | H | H | —CH₂F | C |
| 1010 | o-O-i-Bu | H | H | —CH₂F | C |
| 1011 | m-O-i-Bu | H | H | —CH₂F | C |
| 1012 | p-O-i-Bu | H | H | —CH₂F | C |
| 1013 | o-OCF₃ | H | H | —CH₂F | C |
| 1014 | m-OCF₃ | H | H | —CH₂F | C |
| 1015 | p-OCF₃ | H | H | —CH₂F | C |
| 1016 | H | H | H | —CH₂F | N |
| 1017 | o-OCH₃ | H | H | —CH₂F | N |
| 1018 | m-OCH₃ | H | H | —CH₂F | N |
| 1019 | p-OCH₃ | H | H | —CH₂F | N |
| 1020 | o-Cl | H | H | —CH₂F | N |
| 1021 | m-Cl | H | H | —CH₂F | N |
| 1022 | p-Cl | H | H | —CH₂F | N |
| 1023 | o-Br | H | H | —CH₂F | N |
| 1024 | m-Br | H | H | —CH₂F | N |
| 1025 | p-Br | H | H | —CH₂F | N |
| 1026 | o-NH₂ | H | H | —CH₂F | N |
| 1027 | m-NH₂ | H | H | —CH₂F | N |
| 1028 | p-NH₂ | H | H | —CH₂F | N |

TABLE 1-continued

| No. | R¹ | R² | R³ | R⁴ | X |
|---|---|---|---|---|---|
| 1029 | o-NO₂ | H | H | —CH₂F | N |
| 1030 | m-NO₂ | H | H | —CH₂F | N |
| 1031 | p-NO₂ | H | H | —CH₂F | N |
| 1032 | o-OC₂H₅ | H | H | —CH₂F | N |
| 1033 | m-OC₂H₅ | H | H | —CH₂F | N |
| 1034 | p-OC₂H₅ | H | H | —CH₂F | N |
| 1035 | p-I | H | H | —CH₂F | N |
| 1036 | o-O-n-Pr | H | H | —CH₂F | N |
| 1037 | m-O-n-Pr | H | H | —CH₂F | N |
| 1038 | p-O-n-Pr | H | H | —CH₂F | N |
| 1039 | o-O-i-Pr | H | H | —CH₂F | N |
| 1040 | m-O-i-Pr | H | H | —CH₂F | N |
| 1041 | p-O-i-Pr | H | H | —CH₂F | N |
| 1042 | o-O-n-Bu | H | H | —CH₂F | N |
| 1043 | m-O-n-Bu | H | H | —CH₂F | N |
| 1044 | p-O-n-Bu | H | H | —CH₂F | N |
| 1045 | o-O-i-Bu | H | H | —CH₂F | N |
| 1046 | m-O-i-Bu | H | H | —CH₂F | N |
| 1047 | p-O-i-Bu | H | H | —CH₂F | N |
| 1048 | o-OCF₃ | H | H | —CH₂F | N |
| 1049 | m-OCF₃ | H | H | —CH₂F | N |
| 1050 | p-OCF₃ | H | H | —CH₂F | N |
| 1051 | H | CF₃CH₂— | CF₃CH₂— | —CH₂OH | C |
| 1052 | o-OCH₃ | CF₃CH₂— | CF₃CH₂— | —CH₂OH | C |
| 1053 | m-OCH₃ | CF₃CH₂— | CF₃CH₂— | —CH₂OH | C |
| 1054 | p-OCH₃ | CF₃CH₂— | CF₃CH₂— | —CH₂OH | C |
| 1055 | o-Cl | CF₃CH₂— | CF₃CH₂— | —CH₂OH | C |
| 1056 | m-Cl | CF₃CH₂— | CF₃CH₂— | —CH₂OH | C |
| 1057 | p-Cl | CF₃CH₂— | CF₃CH₂— | —CH₂OH | C |
| 1058 | o-Br | CF₃CH₂— | CF₃CH₂— | —CH₂OH | C |
| 1059 | m-Br | CF₃CH₂— | CF₃CH₂— | —CH₂OH | C |
| 1060 | p-Br | CF₃CH₂— | CF₃CH₂— | —CH₂OH | C |
| 1061 | o-NH₂ | CF₃CH₂— | CF₃CH₂— | —CH₂OH | C |
| 1062 | m-NH₂ | CF₃CH₂— | CF₃CH₂— | —CH₂OH | C |
| 1063 | p-NH₂ | CF₃CH₂— | CF₃CH₂— | —CH₂OH | C |
| 1064 | o-NO₂ | CF₃CH₂— | CF₃CH₂— | —CH₂OH | C |
| 1065 | m-NO₂ | CF₃CH₂— | CF₃CH₂— | —CH₂OH | C |
| 1066 | p-NO₂ | CF₃CH₂— | CF₃CH₂— | —CH₂OH | C |
| 1067 | o-OC₂H₅ | CF₃CH₂— | CF₃CH₂— | —CH₂OH | C |
| 1068 | m-OC₂H₅ | CF₃CH₂— | CF₃CH₂— | —CH₂OH | C |
| 1069 | p-OC₂H₅ | CF₃CH₂— | CF₃CH₂— | —CH₂OH | C |
| 1070 | p-I | CF₃CH₂— | CF₃CH₂— | —CH₂OH | C |
| 1071 | o-O-n-Pr | CF₃CH₂— | CF₃CH₂— | —CH₂OH | C |
| 1072 | m-O-n-Pr | CF₃CH₂— | CF₃CH₂— | —CH₂OH | C |
| 1073 | p-O-n-Pr | CF₃CH₂— | CF₃CH₂— | —CH₂OH | C |
| 1074 | o-O-i-Pr | CF₃CH₂— | CF₃CH₂— | —CH₂OH | C |
| 1075 | m-O-i-Pr | CF₃CH₂— | CF₃CH₂— | —CH₂OH | C |
| 1076 | p-O-i-Pr | CF₃CH₂— | CF₃CH₂— | —CH₂OH | C |
| 1077 | o-O-n-Bu | CF₃CH₂— | CF₃CH₂— | —CH₂OH | C |
| 1078 | m-O-n-Bu | CF₃CH₂— | CF₃CH₂— | —CH₂OH | C |
| 1079 | p-O-n-Bu | CF₃CH₂— | CF₃CH₂— | —CH₂OH | C |
| 1080 | o-O-i-Bu | CF₃CH₂— | CF₃CH₂— | —CH₂OH | C |
| 1081 | m-O-i-Bu | CF₃CH₂— | CF₃CH₂— | —CH₂OH | C |
| 1082 | p-O-i-Bu | CF₃CH₂— | CF₃CH₂— | —CH₂OH | C |
| 1083 | o-OCF₃ | CF₃CH₂— | CF₃CH₂— | —CH₂OH | C |
| 1084 | m-OCF₃ | CF₃CH₂— | CF₃CH₂— | —CH₂OH | C |
| 1085 | p-OCF₃ | CF₃CH₂— | CF₃CH₂— | —CH₂OH | C |
| 1086 | H | CF₃CH₂— | CF₃CH₂— | —CH₂OH | N |
| 1087 | o-OCH₃ | CF₃CH₂— | CF₃CH₂— | —CH₂OH | N |
| 1088 | m-OCH₃ | CF₃CH₂— | CF₃CH₂— | —CH₂OH | N |
| 1089 | p-OCH₃ | CF₃CH₂— | CF₃CH₂— | —CH₂OH | N |
| 1090 | o-Cl | CF₃CH₂— | CF₃CH₂— | —CH₂OH | N |
| 1091 | m-Cl | CF₃CH₂— | CF₃CH₂— | —CH₂OH | N |
| 1092 | p-Cl | CF₃CH₂— | CF₃CH₂— | —CH₂OH | N |
| 1093 | o-Br | CF₃CH₂— | CF₃CH₂— | —CH₂OH | N |
| 1094 | m-Br | CF₃CH₂— | CF₃CH₂— | —CH₂OH | N |
| 1095 | p-Br | CF₃CH₂— | CF₃CH₂— | —CH₂OH | N |
| 1096 | o-NH₂ | CF₃CH₂— | CF₃CH₂— | —CH₂OH | N |
| 1097 | m-NH₂ | CF₃CH₂— | CF₃CH₂— | —CH₂OH | N |
| 1098 | p-NH₂ | CF₃CH₂— | CF₃CH₂— | —CH₂OH | N |
| 1099 | o-NO₂ | CF₃CH₂— | CF₃CH₂— | —CH₂OH | N |
| 1100 | m-NO₂ | CF₃CH₂— | CF₃CH₂— | —CH₂OH | N |
| 1101 | p-NO₂ | CF₃CH₂— | CF₃CH₂— | —CH₂OH | N |
| 1102 | o-OC₂H₅ | CF₃CH₂— | CF₃CH₂— | —CH₂OH | N |
| 1103 | m-OC₂H₅ | CF₃CH₂— | CF₃CH₂— | —CH₂OH | N |
| 1104 | p-OC₂H₅ | CF₃CH₂— | CF₃CH₂— | —CH₂OH | N |
| 1105 | p-I | CF₃CH₂— | CF₃CH₂— | —CH₂OH | N |

TABLE 1-continued

| No. | R¹ | R² | R³ | R⁴ | X |
|---|---|---|---|---|---|
| 1106 | o-O-n-Pr | CF₃CH₂— | CF₃CH₂— | —CH₂OH | N |
| 1107 | m-O-n-Pr | CF₃CH₂— | CF₃CH₂— | —CH₂OH | N |
| 1108 | p-O-n-Pr | CF₃CH₂— | CF₃CH₂— | —CH₂OH | N |
| 1109 | o-O-i-Pr | CF₃CH₂— | CF₃CH₂— | —CH₂OH | N |
| 1110 | m-O-i-Pr | CF₃CH₂— | CF₃CH₂— | —CH₂OH | N |
| 1111 | p-O-i-Pr | CF₃CH₂— | CF₃CH₂— | —CH₂OH | N |
| 1112 | o-O-n-Bu | CF₃CH₂— | CF₃CH₂— | —CH₂OH | N |
| 1113 | m-O-n-Bu | CF₃CH₂— | CF₃CH₂— | —CH₂OH | N |
| 1114 | p-O-n-Bu | CF₃CH₂— | CF₃CH₂— | —CH₂OH | N |
| 1115 | o-O-i-Bu | CF₃CH₂— | CF₃CH₂— | —CH₂OH | N |
| 1116 | m-O-i-Bu | CF₃CH₂— | CF₃CH₂— | —CH₂OH | N |
| 1117 | p-O-i-Bu | CF₃CH₂— | CF₃CH₂— | —CH₂OH | N |
| 1118 | o-OCF₃ | CF₃CH₂— | CF₃CH₂— | —CH₂OH | N |
| 1119 | m-OCF₃ | CF₃CH₂— | CF₃CH₂— | —CH₂OH | N |
| 1120 | p-OCF₃ | CF₃CH₂— | CF₃CH₂— | —CH₂OH | N |
| 1121 | H | CF₃CH₂— | Me— | —CH₂OH | C |
| 1122 | o-OCH₃ | CF₃CH₂— | Me— | —CH₂OH | C |
| 1123 | m-OCH₃ | CF₃CH₂— | Me— | —CH₂OH | C |
| 1124 | p-OCH₃ | CF₃CH₂— | Me— | —CH₂OH | C |
| 1125 | o-Cl | CF₃CH₂— | Me— | —CH₂OH | C |
| 1126 | m-Cl | CF₃CH₂— | Me— | —CH₂OH | C |
| 1127 | p-Cl | CF₃CH₂— | Me— | —CH₂OH | C |
| 1128 | o-Br | CF₃CH₂— | Me— | —CH₂OH | C |
| 1129 | m-Br | CF₃CH₂— | Me— | —CH₂OH | C |
| 1130 | p-Br | CF₃CH₂— | Me— | —CH₂OH | C |
| 1131 | o-NH₂ | CF₃CH₂— | Me— | —CH₂OH | C |
| 1132 | m-NH₂ | CF₃CH₂— | Me— | —CH₂OH | C |
| 1133 | p-NH₂ | CF₃CH₂— | Me— | —CH₂OH | C |
| 1134 | o-NO₂ | CF₃CH₂— | Me— | —CH₂OH | C |
| 1135 | m-NO₂ | CF₃CH₂— | Me— | —CH₂OH | C |
| 1136 | p-NO₂ | CF₃CH₂— | Me— | —CH₂OH | C |
| 1137 | o-OC₂H₅ | CF₃CH₂— | Me— | —CH₂OH | C |
| 1138 | m-OC₂H₅ | CF₃CH₂— | Me— | —CH₂OH | C |
| 1139 | p-OC₂H₅ | CF₃CH₂— | Me— | —CH₂OH | C |
| 1140 | p-I | CF₃CH₂— | Me— | —CH₂OH | C |
| 1141 | o-O-n-Pr | CF₃CH₂— | Me— | —CH₂OH | C |
| 1142 | m-O-n-Pr | CF₃CH₂— | Me— | —CH₂OH | C |
| 1143 | p-O-n-Pr | CF₃CH₂— | Me— | —CH₂OH | C |
| 1144 | o-O-i-Pr | CF₃CH₂— | Me— | —CH₂OH | C |
| 1145 | m-O-i-Pr | CF₃CH₂— | Me— | —CH₂OH | C |
| 1146 | p-O-i-Pr | CF₃CH₂— | Me— | —CH₂OH | C |
| 1147 | o-O-n-Bu | CF₃CH₂— | Me— | —CH₂OH | C |
| 1148 | m-O-n-Bu | CF₃CH₂— | Me— | —CH₂OH | C |
| 1149 | p-O-n-Bu | CF₃CH₂— | Me— | —CH₂OH | C |
| 1150 | o-O-i-Bu | CF₃CH₂— | Me— | —CH₂OH | C |
| 1151 | m-O-i-Bu | CF₃CH₂— | Me— | —CH₂OH | C |
| 1152 | p-O-i-Bu | CF₃CH₂— | Me— | —CH₂OH | C |
| 1153 | o-OCF₃ | CF₃CH₂— | Me— | —CH₂OH | C |
| 1154 | m-OCF₃ | CF₃CH₂— | Me— | —CH₂OH | C |
| 1155 | p-OCF₃ | CF₃CH₂— | Me— | —CH₂OH | C |
| 1156 | H | CF₃CH₂— | Me— | —CH₂OH | N |
| 1157 | o-OCH₃ | CF₃CH₂— | Me— | —CH₂OH | N |
| 1158 | m-OCH₃ | CF₃CH₂— | Me— | —CH₂OH | N |
| 1159 | p-OCH₃ | CF₃CH₂— | Me— | —CH₂OH | N |
| 1160 | o-Cl | CF₃CH₂— | Me— | —CH₂OH | N |
| 1161 | m-Cl | CF₃CH₂— | Me— | —CH₂OH | N |
| 1162 | p-Cl | CF₃CH₂— | Me— | —CH₂OH | N |
| 1163 | o-Br | CF₃CH₂— | Me— | —CH₂OH | N |
| 1164 | m-Br | CF₃CH₂— | Me— | —CH₂OH | N |
| 1165 | p-Br | CF₃CH₂— | Me— | —CH₂OH | N |
| 1166 | o-NH₂ | CF₃CH₂— | Me— | —CH₂OH | N |
| 1167 | m-NH₂ | CF₃CH₂— | Me— | —CH₂OH | N |
| 1168 | p-NH₂ | CF₃CH₂— | Me— | —CH₂OH | N |
| 1169 | o-NO₂ | CF₃CH₂— | Me— | —CH₂OH | N |
| 1170 | m-NO₂ | CF₃CH₂— | Me— | —CH₂OH | N |
| 1171 | p-NO₂ | CF₃CH₂— | Me— | —CH₂OH | N |
| 1172 | o-OC₂H₅ | CF₃CH₂— | Me— | —CH₂OH | N |
| 1173 | m-OC₂H₅ | CF₃CH₂— | Me— | —CH₂OH | N |
| 1174 | p-OC₂H₅ | CF₃CH₂— | Me— | —CH₂OH | N |
| 1175 | p-I | CF₃CH₂— | Me— | —CH₂OH | N |
| 1176 | o-O-n-Pr | CF₃CH₂— | Me— | —CH₂OH | N |
| 1177 | m-O-n-Pr | CF₃CH₂— | Me— | —CH₂OH | N |
| 1178 | p-O-n-Pr | CF₃CH₂— | Me— | —CH₂OH | N |
| 1179 | o-O-i-Pr | CF₃CH₂— | Me— | —CH₂OH | N |
| 1180 | m-O-i-Pr | CF₃CH₂— | Me— | —CH₂OH | N |
| 1181 | p-O-i-Pr | CF₃CH₂— | Me— | —CH₂OH | N |
| 1182 | o-O-n-Bu | CF₃CH₂— | Me— | —CH₂OH | N |

TABLE 1-continued

| No. | R¹ | R² | R³ | R⁴ | X |
|---|---|---|---|---|---|
| 1183 | m-O-n-Bu | CF₃CH₂— | Me— | —CH₂OH | N |
| 1184 | p-O-n-Bu | CF₃CH₂— | Me— | —CH₂OH | N |
| 1185 | o-O-i-Bu | CF₃CH₂— | Me— | —CH₂OH | N |
| 1186 | m-O-i-Bu | CF₃CH₂— | Me— | —CH₂OH | N |
| 1187 | p-O-i-Bu | CF₃CH₂— | Me— | —CH₂OH | N |
| 1188 | o-OCF₃ | CF₃CH₂— | Me— | —CH₂OH | N |
| 1189 | m-OCF₃ | CF₃CH₂— | Me— | —CH₂OH | N |
| 1190 | p-OCF₃ | CF₃CH₂— | Me— | —CH₂OH | N |
| 1191 | H | CF₃CH₂— | Et— | —CH₂OH | C |
| 1192 | o-OCH₃ | CF₃CH₂— | Et— | —CH₂OH | C |
| 1193 | m-OCH₃ | CF₃CH₂— | Et— | —CH₂OH | C |
| 1194 | p-OCH₃ | CF₃CH₂— | Et— | —CH₂OH | C |
| 1195 | o-Cl | CF₃CH₂— | Et— | —CH₂OH | C |
| 1196 | m-Cl | CF₃CH₂— | Et— | —CH₂OH | C |
| 1197 | p-Cl | CF₃CH₂— | Et— | —CH₂OH | C |
| 1198 | o-Br | CF₃CH₂— | Et— | —CH₂OH | C |
| 1199 | m-Br | CF₃CH₂— | Et— | —CH₂OH | C |
| 1200 | p-Br | CF₃CH₂— | Et— | —CH₂OH | C |
| 1201 | o-NH₂ | CF₃CH₂— | Et— | —CH₂OH | C |
| 1202 | m-NH₂ | CF₃CH₂— | Et— | —CH₂OH | C |
| 1203 | p-NH₂ | CF₃CH₂— | Et— | —CH₂OH | C |
| 1204 | o-NO₂ | CF₃CH₂— | Et— | —CH₂OH | C |
| 1205 | m-NO₂ | CF₃CH₂— | Et— | —CH₂OH | C |
| 1206 | p-NO₂ | CF₃CH₂— | Et— | —CH₂OH | C |
| 1207 | o-OC₂H₅ | CF₃CH₂— | Et— | —CH₂OH | C |
| 1208 | m-OC₂H₅ | CF₃CH₂— | Et— | —CH₂OH | C |
| 1209 | p-OC₂H₅ | CF₃CH₂— | Et— | —CH₂OH | C |
| 1210 | p-I | CF₃CH₂— | Et— | —CH₂OH | C |
| 1211 | o-O-n-Pr | CF₃CH₂— | Et— | —CH₂OH | C |
| 1212 | m-O-n-Pr | CF₃CH₂— | Et— | —CH₂OH | C |
| 1213 | p-O-n-Pr | CF₃CH₂— | Et— | —CH₂OH | C |
| 1214 | o-O-i-Pr | CF₃CH₂— | Et— | —CH₂OH | C |
| 1215 | m-O-i-Pr | CF₃CH₂— | Et— | —CH₂OH | C |
| 1216 | p-O-i-Pr | CF₃CH₂— | Et— | —CH₂OH | C |
| 1217 | o-O-n-Bu | CF₃CH₂— | Et— | —CH₂OH | C |
| 1218 | m-O-n-Bu | CF₃CH₂— | Et— | —CH₂OH | C |
| 1219 | p-O-n-Bu | CF₃CH₂— | Et— | —CH₂OH | C |
| 1220 | o-O-i-Bu | CF₃CH₂— | Et— | —CH₂OH | C |
| 1221 | m-O-i-Bu | CF₃CH₂— | Et— | —CH₂OH | C |
| 1222 | p-O-i-Bu | CF₃CH₂— | Et— | —CH₂OH | C |
| 1223 | o-OCF₃ | CF₃CH₂— | Et— | —CH₂OH | C |
| 1224 | m-OCF₃ | CF₃CH₂— | Et— | —CH₂OH | C |
| 1225 | p-OCF₃ | CF₃CH₂— | Et— | —CH₂OH | C |
| 1226 | H | CF₃CH₂— | Et— | —CH₂OH | N |
| 1227 | o-OCH₃ | CF₃CH₂— | Et— | —CH₂OH | N |
| 1228 | m-OCH₃ | CF₃CH₂— | Et— | —CH₂OH | N |
| 1229 | p-OCH₃ | CF₃CH₂— | Et— | —CH₂OH | N |
| 1230 | o-Cl | CF₃CH₂— | Et— | —CH₂OH | N |
| 1231 | m-Cl | CF₃CH₂— | Et— | —CH₂OH | N |
| 1232 | p-Cl | CF₃CH₂— | Et— | —CH₂OH | N |
| 1233 | o-Br | CF₃CH₂— | Et— | —CH₂OH | N |
| 1234 | m-Br | CF₃CH₂— | Et— | —CH₂OH | N |
| 1235 | p-Br | CF₃CH₂— | Et— | —CH₂OH | N |
| 1236 | o-NH₂ | CF₃CH₂— | Et— | —CH₂OH | N |
| 1237 | m-NH₂ | CF₃CH₂— | Et— | —CH₂OH | N |
| 1238 | p-NH₂ | CF₃CH₂— | Et— | —CH₂OH | N |
| 1239 | o-NO₂ | CF₃CH₂— | Et— | —CH₂OH | N |
| 1240 | m-NO₂ | CF₃CH₂— | Et— | —CH₂OH | N |
| 1241 | p-NO₂ | CF₃CH₂— | Et— | —CH₂OH | N |
| 1242 | o-OC₂H₅ | CF₃CH₂— | Et— | —CH₂OH | N |
| 1243 | m-OC₂H₅ | CF₃CH₂— | Et— | —CH₂OH | N |
| 1244 | p-OC₂H₅ | CF₃CH₂— | Et— | —CH₂OH | N |
| 1245 | p-I | CF₃CH₂— | Et— | —CH₂OH | N |
| 1246 | o-O-n-Pr | CF₃CH₂— | Et— | —CH₂OH | N |
| 1247 | m-O-n-Pr | CF₃CH₂— | Et— | —CH₂OH | N |
| 1248 | p-O-n-Pr | CF₃CH₂— | Et— | —CH₂OH | N |
| 1249 | o-O-i-Pr | CF₃CH₂— | Et— | —CH₂OH | N |
| 1250 | m-O-i-Pr | CF₃CH₂— | Et— | —CH₂OH | N |
| 1251 | p-O-i-Pr | CF₃CH₂— | Et— | —CH₂OH | N |
| 1252 | o-O-n-Bu | CF₃CH₂— | Et— | —CH₂OH | N |
| 1253 | m-O-n-Bu | CF₃CH₂— | Et— | —CH₂OH | N |
| 1254 | p-O-n-Bu | CF₃CH₂— | Et— | —CH₂OH | N |
| 1255 | o-O-i-Bu | CF₃CH₂— | Et— | —CH₂OH | N |
| 1256 | m-C-i-Bu | CF₃CH₂— | Et— | —CH₂OH | N |
| 1257 | p-O-i-Bu | CF₃CH₂— | Et— | —CH₂OH | N |
| 1258 | o-OCF₃ | CF₃CH₂— | Et— | —CH₂OH | N |
| 1259 | m-OCF₃ | CF₃CH₂— | Et— | —CH₂OH | N |

TABLE 1-continued

| No. | R¹ | R² | R³ | R⁴ | X |
|---|---|---|---|---|---|
| 1260 | p-OCF₃ | CF₃CH₂— | Et— | —CH₂OH | N |
| 1261 | H | CF₃CH₂— | H | —CH₂OH | C |
| 1262 | o-OCH₃ | CF₃CH₂— | H | —CH₂OH | C |
| 1263 | m-OCH₃ | CF₃CH₂— | H | —CH₂OH | C |
| 1264 | p-OCH₃ | CF₃CH₂— | H | —CH₂OH | C |
| 1265 | o-Cl | CF₃CH₂— | H | —CH₂OH | C |
| 1266 | m-Cl | CF₃CH₂— | H | —CH₂OH | C |
| 1267 | p-Cl | CF₃CH₂— | H | —CH₂OH | C |
| 1268 | o-Br | CF₃CH₂— | H | —CH₂OH | C |
| 1269 | m-Br | CF₃CH₂— | H | —CH₂OH | C |
| 1270 | p-Br | CF₃CH₂— | H | —CH₂OH | C |
| 1271 | o-NH₂ | CF₃CH₂— | H | —CH₂OH | C |
| 1272 | m-NH₂ | CF₃CH₂— | H | —CH₂OH | C |
| 1273 | p-NH₂ | CF₃CH₂— | H | —CH₂OH | C |
| 1274 | o-NO₂ | CF₃CH₂— | H | —CH₂OH | C |
| 1275 | m-NO₂ | CF₃CH₂— | H | —CH₂OH | C |
| 1276 | p-NO₂ | CF₃CH₂— | H | —CH₂OH | C |
| 1277 | o-OC₂H₅ | CF₃CH₂— | H | —CH₂OH | C |
| 1278 | m-OC₂H₅ | CF₃CH₂— | H | —CH₂OH | C |
| 1279 | p-OC₂H₅ | CF₃CH₂— | H | —CH₂OH | C |
| 1280 | p-I | CF₃CH₂— | H | —CH₂OH | C |
| 1281 | o-O-n-Pr | CF₃CH₂— | H | —CH₂OH | C |
| 1282 | m-O-n-Pr | CF₃CH₂— | H | —CH₂OH | C |
| 1283 | p-O-n-Pr | CF₃CH₂— | H | —CH₂OH | C |
| 1284 | o-O-i-Pr | CF₃CH₂— | H | —CH₂OH | C |
| 1285 | m-O-i-Pr | CF₃CH₂— | H | —CH₂OH | C |
| 1286 | p-O-i-Pr | CF₃CH₂— | H | —CH₂OH | C |
| 1287 | o-O-n-Bu | CF₃CH₂— | H | —CH₂OH | C |
| 1288 | m-O-n-Bu | CF₃CH₂— | H | —CH₂OH | C |
| 1289 | p-O-n-Bu | CF₃CH₂— | H | —CH₂OH | C |
| 1290 | o-O-i-Bu | CF₃CH₂— | H | —CH₂OH | C |
| 1291 | m-O-i-Bu | CF₃CH₂— | H | —CH₂OH | C |
| 1292 | p-O-i-Bu | CF₃CH₂— | H | —CH₂OH | C |
| 1293 | o-OCF₃ | CF₃CH₂— | H | —CH₂OH | C |
| 1294 | m-OCF₃ | CF₃CH₂— | H | —CH₂OH | C |
| 1295 | p-OCF₃ | CF₃CH₂— | H | —CH₂OH | C |
| 1296 | H | CF₃CH₂— | H | —CH₂OH | N |
| 1297 | o-OCH₃ | CF₃CH₂— | H | —CH₂OH | N |
| 1298 | m-OCH₃ | CF₃CH₂— | H | —CH₂OH | N |
| 1299 | p-OCH₃ | CF₃CH₂— | H | —CH₂OH | N |
| 1300 | o-Cl | CF₃CH₂— | H | —CH₂OH | N |
| 1301 | m-Cl | CF₃CH₂— | H | —CH₂OH | N |
| 1302 | p-Cl | CF₃CH₂— | H | —CH₂dH | N |
| 1303 | o-Br | CF₃CH₂— | H | —CH₂OH | N |
| 1304 | m-Br | CF₃CH₂— | H | —CH₂OH | N |
| 1305 | p-Br | CF₃CH₂— | H | —CH₂OH | N |
| 1306 | o-NH₂ | CF₃CH₂— | H | —CH₂OH | N |
| 1307 | m-NH₂ | CF₃CH₂— | H | —CH₂OH | N |
| 1308 | p-NH₂ | CF₃CH₂— | H | —CH₂OH | N |
| 1309 | o-NO₂ | CF₃CH₂— | H | —CH₂OH | N |
| 1310 | m-NO₂ | CF₃CH₂— | H | —CH₂OH | N |
| 1311 | p-NO₂ | CF₃CH₂— | H | —CH₂OH | N |
| 1312 | o-OC₂H₅ | CF₃CH₂— | H | —CH₂OH | N |
| 1313 | m-OC₂H₅ | CF₃CH₂— | H | —CH₂OH | N |
| 1314 | p-OC₂H₅ | CF₃CH₂— | H | —CH₂OH | N |
| 1315 | p-I | CF₃CH₂— | H | —CH₂OH | N |
| 1316 | o-O-n-Pr | CF₃CH₂— | H | —CH₂OH | N |
| 1317 | m-O-n-Pr | CF₃CH₂— | H | —CH₂OH | N |
| 1318 | p-O-n-Pr | CF₃CH₂— | H | —CH₂OH | N |
| 1319 | o-O-i-Pr | CF₃CH₂— | H | —CH₂OH | N |
| 1320 | m-O-i-Pr | CF₃CH₂— | H | —CH₂OH | N |
| 1321 | p-O-i-Pr | CF₃CH₂— | H | —CH₂OH | N |
| 1322 | o-O-n-Bu | CF₃CH₂— | H | —CH₂OH | N |
| 1323 | m-O-n-Bu | CF₃CH₂— | H | —CH₂OH | N |
| 1324 | p-O-n-Bu | CF₃CH₂— | H | —CH₂OH | N |
| 1325 | o-O-i-Bu | CF₃CH₂— | H | —CH₂OH | N |
| 1326 | m-O-i-Bu | CF₃CH₂— | H | —CH₂OH | N |
| 1327 | p-O-i-Bu | CF₃CH₂— | H | —CH₂OH | N |
| 1328 | o-OCF₃ | CF₃CH₂— | H | —CH₂OH | N |
| 1329 | m-OCF₃ | CF₃CH₂— | H | —CH₂OH | N |
| 1330 | p-OCF₃ | CF₃CH₂— | H | —CH₂OH | N |
| 1331 | H | H | H | —CH₂OH | C |
| 1332 | o-OCH₃ | H | H | —CH₂OH | C |
| 1333 | m-OCH₃ | H | H | —CH₂OH | C |
| 1334 | p-OCH₃ | H | H | —CH₂OH | C |
| 1335 | o-Cl | H | H | —CH₂OH | C |
| 1336 | m-Cl | H | H | —CH₂OH | C |

TABLE 1-continued

| No. | R¹ | R² | R³ | R⁴ | X |
|---|---|---|---|---|---|
| 1337 | p-Cl | H | H | —CH₂OH | C |
| 1338 | o-Br | H | H | —CH₂OH | C |
| 1339 | m-Br | H | H | —CH₂OH | C |
| 1340 | p-Br | H | H | —CH₂OH | C |
| 1341 | o-NH₂ | H | H | —CH₂OH | C |
| 1342 | m-NH₂ | H | H | —CH₂OH | C |
| 1343 | p-NH₂ | H | H | —CH₂OH | C |
| 1344 | o-NO₂ | H | H | —CH₂OH | C |
| 1345 | m-NO₂ | H | H | —CH₂OH | C |
| 1346 | p-NO₂ | H | H | —CH₂OH | C |
| 1347 | o-OC₂H₅ | H | H | —CH₂OH | C |
| 1348 | m-OC₂H₅ | H | H | —CH₂OH | C |
| 1349 | p-OC₂H₅ | H | H | —CH₂OH | C |
| 1350 | p-I | H | H | —CH₂OH | C |
| 1351 | o-O-n-Pr | H | H | —CH₂OH | C |
| 1352 | m-O-n-Pr | H | H | —CH₂OH | C |
| 1353 | p-O-n-Pr | H | H | —CH₂OH | C |
| 1354 | o-O-i-Pr | H | H | —CH₂OH | C |
| 1355 | m-O-i-Pr | H | H | —CH₂OH | C |
| 1356 | p-O-i-Pr | H | H | —CH₂OH | C |
| 1357 | o-O-n-Bu | H | H | —CH₂OH | C |
| 1358 | m-O-n-Bu | H | H | —CH₂OH | C |
| 1359 | p-O-n-Bu | H | H | —CH₂OH | C |
| 1360 | o-O-i-Bu | H | H | —CH₂OH | C |
| 1361 | m-O-i-Bu | H | H | —CH₂OH | C |
| 1362 | p-O-i-Bu | H | H | —CH₂OH | C |
| 1363 | o-OCF₃ | H | H | —CH₂OH | C |
| 1364 | m-OCF₃ | H | H | —CH₂OH | C |
| 1365 | p-OCF₃ | H | H | —CH₂OH | C |
| 1366 | H | H | H | —CH₂OH | N |
| 1367 | o-OCH₃ | H | H | —CH₂OH | N |
| 1368 | m-OCH₃ | H | H | —CH₂OH | N |
| 1369 | p-OCH₃ | H | H | —CH₂OH | N |
| 1370 | o-Cl | H | H | —CH₂OH | N |
| 1371 | m-Cl | H | H | —CH₂OH | N |
| 1372 | p-Cl | H | H | —CH₂OH | N |
| 1373 | o-Br | H | H | —CH₂OH | N |
| 1374 | m-Br | H | H | —CH₂OH | N |
| 1375 | p-Br | H | H | —CH₂OH | N |
| 1376 | o-NH₂ | H | H | —CH₂OH | N |
| 1377 | m-NH₂ | H | H | —CH₂OH | N |
| 1378 | p-NH₂ | H | H | —CH₂OH | N |
| 1379 | o-NO₂ | H | H | —CH₂OH | N |
| 1380 | m-NO₂ | H | H | —CH₂OH | N |
| 1381 | p-NO₂ | H | H | —CH₂OH | N |
| 1382 | o-OC₂H₅ | H | H | —CH₂OH | N |
| 1383 | m-OC₂H₅ | H | H | —CH₂OH | N |
| 1384 | p-OC₂H₅ | H | H | —CH₂OH | N |
| 1385 | p-I | H | H | —CH₂OH | N |
| 1386 | o-O-n-Pr | H | H | —CH₂OH | N |
| 1387 | m-O-n-Pr | H | H | —CH₂OH | N |
| 1388 | p-O-n-Pr | H | H | —CH₂OH | N |
| 1389 | o-O-i-Pr | H | H | —CH₂OH | N |
| 1390 | m-O-i-Pr | H | H | —CH₂OH | C |
| 1391 | p-O-i-Pr | H | H | —CH₂OH | N |
| 1392 | o-O-n-Bu | H | H | —CH₂OH | N |
| 1393 | m-O-n-Bu | H | H | —CH₂OH | N |
| 1394 | p-O-n-Bu | H | H | —CH₂OH | N |
| 1395 | o-O-i-Bu | H | H | —CH₂OH | N |
| 1396 | m-O-i-Bu | H | H | —CH₂OH | N |
| 1397 | p-O-i-Bu | H | H | —CH₂OH | N |
| 1398 | o-OCF₃ | H | H | —CH₂OH | N |
| 1399 | m-OCF₃ | H | H | —CH₂OH | N |
| 1400 | p-OCF₃ | H | H | —CH₂OH | N |
| 1401 | H | —CH₂O—CO-t-Bu | —CH₂O—CO-t-Bu | H | C |
| 1402 | o-OCH₃ | —CH₂O—CO-t-Bu | —CH₂O—CO-t-Bu | H | C |
| 1403 | m-OCH₃ | —CH₂O—CO-t-Bu | —CH₂O—CO-t-Bu | H | C |
| 1404 | p-OCH₃ | —CH₂O—CO-t-Bu | —CH₂O—CO-t-Bu | H | C |
| 1405 | o-Cl | —CH₂O—CO-t-Bu | —CH₂O—CO-t-Bu | H | C |
| 1406 | m-Cl | —CH₂O—CO-t-Bu | —CH₂O—CO-t-Bu | H | C |
| 1407 | p-Cl | —CH₂O—CO-t-Bu | —CH₂O—CO-t-Bu | H | C |
| 1408 | o-Br | —CH₂O—CO-t-Bu | —CH₂O—CO-t-Bu | H | C |
| 1409 | m-Br | —CH₂O—CO-t-Bu | —CH₂O—CO-t-Bu | H | C |
| 1410 | p-Br | —CH₂O—CO-t-Bu | —CH₂O—CO-t-Bu | H | C |
| 1411 | o-NH₂ | —CH₂O—CO-t-Bu | —CH₂O—CO-t-Bu | H | C |
| 1412 | m-NH₂ | —CH₂O—CO-t-Bu | —CH₂O—CO-t-Bu | H | C |
| 1413 | p-NH₂ | —CH₂O—CO-t-Bu | —CH₂O—CO-t-Bu | H | C |

TABLE 1-continued

| No. | R¹ | R² | R³ | R⁴ | X |
|---|---|---|---|---|---|
| 1414 | o-NO₂ | —CH₂O—CO-t-Bu | —CH₂O—CO-t-Bu | H | C |
| 1415 | m-NO₂ | —CH₂O—CO-t-Bu | —CH₂O—CO-t-Bu | H | C |
| 1416 | p-NO₂ | —CH₂O—CO-t-Bu | —CH₂O—CO-t-Bu | H | C |
| 1417 | o-OC₂H₅ | —CH₂O—CO-t-Bu | —CH₂O—CO-t-Bu | H | C |
| 1418 | m-OC₂H₅ | —CH₂O—CO-t-Bu | —CH₂O—CO-t-Bu | H | C |
| 1419 | p-OC₂H₅ | —CH₂O—CO-t-Bu | —CH₂O—CO-t-Bu | H | C |
| 1420 | p-I | —CH₂O—CO-t-Bu | —CH₂O—CO-t-Bu | H | C |
| 1421 | o-O-n-Pr | —CH₂O—CO-t-Bu | —CH₂O—CO-t-Bu | H | C |
| 1422 | m-O-n-Pr | —CH₂O—CO-t-Bu | —CH₂O—CO-t-Bu | H | C |
| 1423 | p-O-n-Pr | —CH₂O—CO-t-Bu | —CH₂O—CO-t-Bu | H | C |
| 1424 | o-O-i-Pr | —CH₂O—CO-t-Bu | —CH₂O—CO-t-Bu | H | C |
| 1425 | m-O-i-Pr | —CH₂O—CO-t-Bu | —CH₂O—CO-t-Bu | H | C |
| 1426 | p-O-i-Pr | —CH₂O—CO-t-Bu | —CH₂O—CO-t-Bu | H | C |
| 1427 | o-O-n-Bu | —CH₂O—CO-t-Bu | —CH₂O—CO-t-Bu | H | C |
| 1428 | m-O-n-Bu | —CH₂O—CO-t-Bu | —CH₂O—CO-t-Bu | H | C |
| 1429 | p-O-n-Bu | —CH₂O—CO-t-Bu | —CH₂O—CO-t-Bu | H | C |
| 1430 | o-O-i-Bu | —CH₂O—CO-t-Bu | —CH₂O—CO-t-Bu | H | C |
| 1431 | m-O-i-Bu | —CH₂O—CO-t-Bu | —CH₂O—CO-t-Bu | H | C |
| 1432 | p-O-i-Bu | —CH₂O—CO-t-Bu | —CH₂O—CO-t-Bu | H | C |
| 1433 | o-OCF₃ | —CH₂O—CO-t-Bu | —CH₂O—CO-t-Bu | H | C |
| 1434 | m-OCF₃ | —CH₂O—CO-t-Bu | —CH₂O—CO-t-Bu | H | C |
| 1435 | p-OCF₃ | —CH₂O—CO-t-Bu | —CH₂O—CO-t-Bu | H | C |
| 1436 | H | —CH₂O—CO-t-Bu | —CH₂O—CO-t-Bu | Me— | C |
| 1437 | o-OCH₃ | —CH₂O—CO-t-Bu | —CH₂O—CO-t-Bu | Me— | C |
| 1438 | m-OCH₃ | —CH₂O—CO-t-Bu | —CH₂O—CO-t-Bu | Me— | C |
| 1439 | p-OCH₃ | —CH₂O—CO-t-Bu | —CH₂O—CO-t-Bu | Me— | C |
| 1440 | o-Cl | —CH₂O—CO-t-Bu | —CH₂O—CO-t-Bu | Me— | C |
| 1441 | m-Cl | —CH₂O—CO-t-Bu | —CH₂O—CO-t-Bu | Me— | C |
| 1442 | p-Cl | —CH₂O—CO-t-Bu | —CH₂O—CO-t-Bu | Me— | C |
| 1443 | o-Br | —CH₂O—CO-t-Bu | —CH₂O—CO-t-Bu | Me— | C |
| 1444 | m-Br | —CH₂O—CO-t-Bu | —CH₂O—CO-t-Bu | Me— | C |
| 1445 | p-Br | —CH₂O—CO-t-Bu | —CH₂O—CO-t-Bu | Me— | C |
| 1446 | o-NH₂ | —CH₂O—CO-t-Bu | —CH₂O—CO-t-Bu | Me— | C |
| 1447 | m-NH₂ | —CH₂O—CO-t-Bu | —CH₂O—CO-t-Bu | Me— | C |
| 1448 | p-NH₂ | —CH₂O—CO-t-Bu | —CH₂O—CO-t-Bu | Me— | C |
| 1449 | o-NO₂ | —CH₂O—CO-t-Bu | —CH₂O—CO-t-Bu | Me— | C |
| 1450 | m-NO₂ | —CH₂O—CO-t-Bu | —CH₂O—CO-t-Bu | Me— | C |
| 1451 | p-NO₂ | —CH₂O—CO-t-Bu | —CH₂O—CO-t-Bu | Me— | C |
| 1452 | o-OC₂H₅ | —CH₂O—CO-t-Bu | —CH₂O—CO-t-Bu | Me— | C |
| 1453 | m-OC₂H₅ | —CH₂O—CO-t-Bu | —CH₂O—CO-t-Bu | Me— | C |
| 1454 | p-OC₂H₅ | —CH₂O—CO-t-Bu | —CH₂O—CO-t-Bu | Me— | C |
| 1455 | p-I | —CH₂O—CO-t-Bu | —CH₂O—CO-t-Bu | Me— | C |
| 1456 | o-O-n-Pr | —CH₂O—CO-t-Bu | —CH₂O—CO-t-Bu | Me— | C |
| 1457 | m-O-n-Pr | —CH₂O—CO-t-Bu | —CH₂O—CO-t-Bu | Me— | C |
| 1458 | p-O-n-Pr | —CH₂O—CO-t-Bu | —CH₂O—CO-t-Bu | Me— | C |
| 1459 | o-O-i-Pr | —CH₂O—CO-t-Bu | —CH₂O—CO-t-Bu | Me— | C |
| 1460 | m-O-i-Pr | —CH₂O—CO-t-Bu | —CH₂O—CO-t-Bu | Me— | C |
| 1461 | p-O-i-Pr | —CH₂O—CO-t-Bu | —CH₂O—CO-t-Bu | Me— | C |
| 1462 | o-O-n-Bu | —CH₂O—CO-t-Bu | —CH₂O—CO-t-Bu | Me— | C |
| 1463 | m-O-n-Bu | —CH₂O—CO-t-Bu | —CH₂O—CO-t-Bu | Me— | C |
| 1464 | p-O-n-Bu | —CH₂O—CO-t-Bu | —CH₂O—CO-t-Bu | Me— | C |
| 1465 | o-O-i-Bu | —CH₂O—CO-t-Bu | —CH₂O—CO-t-Bu | Me— | C |
| 1466 | m-O-i-Bu | —CH₂O—CO-t-Bu | —CH₂O—CO-t-Bu | Me— | C |
| 1467 | p-O-i-Bu | —CH₂O—CO-t-Bu | —CH₂O—CO-t-Bu | Me— | C |
| 1468 | o-OCF₃ | —CH₂O—CO-t-Bu | —CH₂O—CO-t-Bu | Me— | C |
| 1469 | m-OCF₃ | —CH₂O—CO-t-Bu | —CH₂O—CO-t-Bu | Me— | C |
| 1470 | p-OCF₃ | —CH₂O—CO-t-Bu | —CH₂O—CO-t-Bu | Me— | C |
| 1471 | H | —CH₂O—CO-t-Bu | —CH₂O—CO-t-Bu | —CH₂F | C |
| 1472 | o-OCH₃ | —CH₂O—CO-t-Bu | —CH₂O—CO-t-Bu | —CH₂F | C |
| 1473 | m-OCH₃ | —CH₂O—CO-t-Bu | —CH₂O—CO-t-Bu | —CH₂F | C |
| 1474 | p-OCH₃ | —CH₂O—CO-t-Bu | —CH₂O—CO-t-Bu | —CH₂F | C |
| 1475 | o-Cl | —CH₂O—CO-t-Bu | —CH₂O—CO-t-Bu | —CH₂F | C |
| 1476 | m-Cl | —CH₂O—CO-t-Bu | —CH₂O—CO-t-Bu | —CH₂F | C |
| 1477 | p-Cl | —CH₂O—CO-t-Bu | —CH₂O—CO-t-Bu | —CH₂F | C |
| 1478 | o-Br | —CH₂O—CO-t-Bu | —CH₂O—CO-t-Bu | —CH₂F | C |
| 1479 | m-Br | —CH₂O—CO-t-Bu | —CH₂O—CO-t-Bu | —CH₂F | C |
| 1480 | p-Br | —CH₂O—CO-t-Bu | —CH₂O—CO-t-Bu | —CH₂F | C |
| 1481 | o-NH₂ | —CH₂O—CO-t-Bu | —CH₂O—CO-t-Bu | —CH₂F | C |
| 1482 | m-NH₂ | —CH₂O—CO-t-Bu | —CH₂O—CO-t-Bu | —CH₂F | C |
| 1483 | p-NH₂ | —CH₂O—CO-t-Bu | —CH₂O—CO-t-Bu | —CH₂F | C |
| 1484 | o-NO₂ | —CH₂O—CO-t-Bu | —CH₂O—CO-t-Bu | —CH₂F | C |
| 1485 | m-NO₂ | —CH₂O—CO-t-Bu | —CH₂O—CO-t-Bu | —CH₂F | C |
| 1486 | p-NO₂ | —CH₂O—CO-t-Bu | —CH₂O—CO-t-Bu | —CH₂F | C |
| 1487 | o-OC₂H₅ | —CH₂O—CO-t-Bu | —CH₂O—CO-t-Bu | —CH₂F | C |
| 1488 | m-OC₂H₅ | —CH₂O—CO-t-Bu | —CH₂O—CO-t-Bu | —CH₂F | C |
| 1489 | p-OC₂H₅ | —CH₂O—CO-t-Bu | —CH₂O—CO-t-Bu | —CH₂F | C |
| 1490 | p-I | —CH₂O—CO-t-Bu | —CH₂O—CO-t-Bu | —CH₂F | C |

TABLE 1-continued

| No. | R¹ | R² | R³ | R⁴ | X |
|---|---|---|---|---|---|
| 1491 | o-O-n-Pr | —CH₂O—CO-t-Bu | —CH₂O—CO-t-Bu | —CH₂F | C |
| 1492 | m-O-n-Pr | —CH₂O—CO-t-Bu | —CH₂O—CO-t-Bu | —CH₂F | C |
| 1493 | p-O-n-Pr | —CH₂O—CO-t-Bu | —CH₂O—CO-t-Bu | —CH₂F | C |
| 1494 | o-O-i-Pr | —CH₂O—CO-t-Bu | —CH₂O—CO-t-Bu | —CH₂F | C |
| 1495 | m-O-i-Pr | —CH₂O—CO-t-Bu | —CH₂O—CO-t-Bu | —CH₂F | C |
| 1496 | p-O-i-Pr | —CH₂O—CO-t-Bu | —CH₂O—CO-t-Bu | —CH₂F | C |
| 1497 | o-O-n-Bu | —CH₂O—CO-t-Bu | —CH₂O—CO-t-Bu | —CH₂F | C |
| 1498 | m-O-n-Bu | —CH₂O—CO-t-Bu | —CH₂O—CO-t-Bu | —CH₂F | C |
| 1499 | p-O-n-Bu | —CH₂O—CO-t-Bu | —CH₂O—CO-t-Bu | —CH₂F | C |
| 1500 | o-O-i-Bu | —CH₂O—CO-t-Bu | —CH₂O—CO-t-Bu | —CH₂F | C |
| 1501 | m-O-i-Bu | —CH₂O—CO-t-Bu | —CH₂O—CO-t-Bu | —CH₂F | C |
| 1502 | p-O-i-Bu | —CH₂O—CO-t-Bu | —CH₂O—CO-t-Bu | —CH₂F | C |
| 1503 | o-OCF₃ | —CH₂O—CO-t-Bu | —CH₂O—CO-t-Bu | —CH₂F | C |
| 1504 | m-OCF₃ | —CH₂O—CO-t-Bu | —CH₂O—CO-t-Bu | —CH₂F | C |
| 1505 | p-OCF₃ | —CH₂O—CO-t-Bu | —CH₂O—CO-t-Bu | —CH₂F | C |
| 1506 | H | —CH₂O—CO-t-Bu | —CH₂O—CO-t-Bu | —CH₂OH | C |
| 1507 | o-OCH₃ | —CH₂O—CO-t-Bu | —CH₂O—CO-t-Bu | —CH₂OH | C |
| 1508 | m-OCH₃ | —CH₂O—CO-t-Bu | —CH₂O—CO-t-Bu | —CH₂OH | C |
| 1509 | p-OCH₃ | —CH₂O—CO-t-Bu | —CH₂O—CO-t-Bu | —CH₂OH | C |
| 1510 | o-Cl | —CH₂O—CO-t-Bu | —CH₂O—CO-t-Bu | —CH₂OH | C |
| 1511 | m-Cl | —CH₂O—CO-t-Bu | —CH₂O—CO-t-Bu | —CH₂OH | C |
| 1512 | p-Cl | —CH₂O—CO-t-Bu | —CH₂O—CO-t-Bu | —CH₂OH | C |
| 1513 | o-Br | —CH₂O—CO-t-Bu | —CH₂O—CO-t-Bu | —CH₂OH | C |
| 1514 | m-Br | —CH₂O—CO-t-Bu | —CH₂O—CO-t-Bu | —CH₂OH | C |
| 1515 | p-Br | —CH₂O—CO-t-Bu | —CH₂O—CO-t-Bu | —CH₂OH | C |
| 1516 | o-NH₂ | —CH₂O—CO-t-Bu | —CH₂O—CO-t-Bu | —CH₂OH | C |
| 1517 | m-NH₂ | —CH₂O—CO-t-Bu | —CH₂O—CO-t-Bu | —CH₂OH | C |
| 1518 | p-NH₂ | —CH₂O—CO-t-Bu | —CH₂O—CO-t-Bu | —CH₂OH | C |
| 1519 | o-NO₂ | —CH₂O—CO-t-Bu | —CH₂O—CO-t-Bu | —CH₂OH | C |
| 1520 | m-NO₂ | —CH₂O—CO-t-Bu | —CH₂O—CO-t-Bu | —CH₂OH | C |
| 1521 | p-NO₂ | —CH₂O—CO-t-Bu | —CH₂O—CO-t-Bu | —CH₂OH | C |
| 1522 | o-OC₂H₅ | —CH₂O—CO-t-Bu | —CH₂O—CO-t-Bu | —CH₂OH | C |
| 1523 | m-OC₂H₅ | —CH₂O—CO-t-Bu | —CH₂O—CO-t-Bu | —CH₂OH | C |
| 1524 | p-OC₂H₅ | —CH₂O—CO-t-Bu | —CH₂O—CO-t-Bu | —CH₂OH | C |
| 1525 | p-I | —CH₂O—CO-t-Bu | —CH₂O—CO-t-Bu | —CH₂OH | C |
| 1526 | o-O-n-Pr | —CH₂O—CO-t-Bu | —CH₂O—CO-t-Bu | —CH₂OH | C |
| 1527 | m-O-n-Pr | —CH₂O—CO-t-Bu | —CH₂O—CO-t-Bu | —CH₂OH | C |
| 1528 | p-O-n-Pr | —CH₂O—CO-t-Bu | —CH₂O—CO-t-Bu | —CH₂OH | C |
| 1529 | o-O-i-Pr | —CH₂O—CO-t-Bu | —CH₂O—CO-t-Bu | —CH₂OH | C |
| 1530 | m-O-i-Pr | —CH₂O—CO-t-Bu | —CH₂O—CO-t-Bu | —CH₂OH | C |
| 1531 | p-O-i-Pr | —CH₂O—CO-t-Bu | —CH₂O—CO-t-Bu | —CH₂OH | C |
| 1532 | o-O-n-Bu | —CH₂O—CO-t-Bu | —CH₂O—CO-t-Bu | —CH₂OH | C |
| 1533 | m-O-n-Bu | —CH₂O—CO-t-Bu | —CH₂O—CO-t-Bu | —CH₂OH | C |
| 1534 | p-O-n-Bu | —CH₂O—CO-t-Bu | —CH₂O—CO-t-Bu | —CH₂OH | C |
| 1535 | o-O-i-Bu | —CH₂O—CO-t-Bu | —CH₂O—CO-t-Bu | —CH₂OH | C |
| 1536 | m-O-i-Bu | —CH₂O—CO-t-Bu | —CH₂O—CO-t-Bu | —CH₂OH | C |
| 1537 | p-O-i-Bu | —CH₂O—CO-t-Bu | —CH₂O—CO-t-Bu | —CH₂OH | C |
| 1538 | o-OCF₃ | —CH₂O—CO-t-Bu | —CH₂O—CO-t-Bu | —CH₂OH | C |
| 1539 | m-OCF₃ | —CH₂O—CO-t-Bu | —CH₂O—CO-t-Bu | —CH₂OH | C |
| 1540 | p-OCF₃ | —CH₂O—CO-t-Bu | —CH₂O—CO-t-Bu | —CH₂OH | C |
| 1541 | H | —CH₂CH₂S—CO-i-Pr | —CH₂CH₂S—CO-i-Pr | H | C |
| 1542 | o-OCH₃ | —CH₂CH₂S—CO-i-Pr | —CH₂CH₂S—CO-i-Pr | H | C |
| 1543 | m-OCH₃ | —CH₂CH₂S—CO-i-Pr | —CH₂CH₂S—CO-i-Pr | H | C |
| 1544 | p-OCH₃ | —CH₂CH₂S—CO-i-Pr | —CH₂CH₂S—CO-i-Pr | H | C |
| 1545 | o-Cl | —CH₂CH₂S—CO-i-Pr | —CH₂CH₂S—CO-i-Pr | H | C |
| 1546 | m-Cl | —CH₂CH₂S—CO-i-Pr | —CH₂CH₂S—CO-i-Pr | H | C |
| 1547 | p-Cl | —CH₂CH₂S—CO-i-Pr | —CH₂CH₂S—CO-i-Pr | H | C |
| 1548 | o-Br | —CH₂CH₂S—CO-i-Pr | —CH₂CH₂S—CO-i-Pr | H | C |
| 1549 | m-Br | —CH₂CH₂S—CO-i-Pr | —CH₂CH₂S—CO-i-Pr | H | C |
| 1550 | p-Br | —CH₂CH₂S—CO-i-Pr | —CH₂CH₂S—CO-i-Pr | H | C |
| 1551 | o-NH₂ | —CH₂CH₂S—CO-i-Pr | —CH₂CH₂S—CO-i-Pr | H | C |
| 1552 | m-NH₂ | —CH₂CH₂S—CO-i-Pr | —CH₂CH₂S—CO-i-Pr | H | C |
| 1553 | p-NH₂ | —CH₂CH₂S—CO-i-Pr | —CH₂CH₂S—CO-i-Pr | H | C |
| 1554 | o-NO₂ | —CH₂CH₂S—CO-i-Pr | —CH₂CH₂S—CO-i-Pr | H | C |
| 1555 | m-NO₂ | —CH₂CH₂S—CO-i-Pr | —CH₂CH₂S—CO-i-Pr | H | C |
| 1556 | p-NO₂ | —CH₂CH₂S—CO-i-Pr | —CH₂CH₂S—CO-i-Pr | H | C |
| 1557 | o-OC₂H₅ | —CH₂CH₂S—CO-i-Pr | —CH₂CH₂S—CO-i-Pr | H | C |
| 1558 | m-OC₂H₅ | —CH₂CH₂S—CO-i-Pr | —CH₂CH₂S—CO-i-Pr | H | C |
| 1559 | p-OC₂H₅ | —CH₂CH₂S—CO-i-Pr | —CH₂CH₂S—CO-i-Pr | H | C |
| 1560 | p-I | —CH₂CH₂S—CO-i-Pr | —CH₂CH₂S—CO-i-Pr | H | C |
| 1561 | o-O-n-Pr | —CH₂CH₂S—CO-i-Pr | —CH₂CH₂S—CO-i-Pr | H | C |
| 1562 | m-O-n-Pr | —CH₂CH₂S—CO-i-Pr | —CH₂CH₂S—CO-i-Pr | H | C |
| 1563 | p-O-n-Pr | —CH₂CH₂S—CO-i-Pr | —CH₂CH₂S—CO-i-Pr | H | C |
| 1564 | o-O-i-Pr | —CH₂CH₂S—CO-i-Pr | —CH₂CH₂S—CO-i-Pr | H | C |
| 1565 | m-O-i-Pr | —CH₂CH₂S—CO-i-Pr | —CH₂CH₂S—CO-i-Pr | H | C |
| 1566 | p-O-i-Pr | —CH₂CH₂S—CO-i-Pr | —CH₂CH₂S—CO-i-Pr | H | C |
| 1567 | o-O-n-Bu | —CH₂CH₂S—CO-i-Pr | —CH₂CH₂S—CO-i-Pr | H | C |

TABLE 1-continued

| No. | R¹ | R² | R³ | R⁴ | X |
|---|---|---|---|---|---|
| 1568 | m-O-n-Bu | —CH₂CH₂S—CO-i-Pr | —CH₂CH₂S—CO-i-Pr | H | C |
| 1569 | p-O-n-Bu | —CH₂CH₂S—CO-i-Pr | —CH₂CH₂S—CO-i-Pr | H | C |
| 1570 | o-O-i-Bu | —CH₂CH₂S—CO-i-Pr | —CH₂CH₂S—CO-i-Pr | H | C |
| 1571 | m-O-i-Bu | —CH₂CH₂S—CO-i-Pr | —CH₂CH₂S—CO-i-Pr | H | C |
| 1572 | p-O-i-Bu | —CH₂CH₂S—CO-i-Pr | —CH₂CH₂S—CO-i-Pr | H | C |
| 1573 | o-OCF₃ | —CH₂CH₂S—CO-i-Pr | —CH₂CH₂S—CO-i-Pr | H | C |
| 1574 | m-OCF₃ | —CH₂CH₂S—CO-i-Pr | —CH₂CH₂S—CO-i-Pr | H | C |
| 1575 | p-OCF₃ | —CH₂CH₂S—CO-i-Pr | —CH₂CH₂S—CO-i-Pr | H | C |
| 1576 | H | —CH₂CH₂S—CO-i-Pr | —CH₂CH₂S—CO-i-Pr | Me— | C |
| 1577 | o-OCH₃ | —CH₂CH₂S—CO-i-Pr | —CH₂CH₂S—CO-i-Pr | Me— | C |
| 1578 | m-OCH₃ | —CH₂CH₂S—CO-i-Pr | —CH₂CH₂S—CO-i-Pr | Me— | C |
| 1579 | p-OCH₃ | —CH₂CH₂S—CO-i-Pr | —CH₂CH₂S—CO-i-Pr | Me— | C |
| 1580 | o-Cl | —CH₂CH₂S—CO-i-Pr | —CH₂CH₂S—CO-i-Pr | Me— | C |
| 1581 | m-Cl | —CH₂CH₂S—CO-i-Pr | —CH₂CH₂S—CO-i-Pr | Me— | C |
| 1582 | p-Cl | —CH₂CH₂S—CO-i-Pr | —CH₂CH₂S—CO-i-Pr | Me— | C |
| 1583 | o-Br | —CH₂CH₂S—CO-i-Pr | —CH₂CH₂S—CO-i-Pr | Me— | C |
| 1584 | m-Br | —CH₂CH₂S—CO-i-Pr | —CH₂CH₂S—CO-i-Pr | Me— | C |
| 1585 | p-Br | —CH₂CH₂S—CO-i-Pr | —CH₂CH₂S—CO-i-Pr | Me— | C |
| 1586 | o-NH₂ | —CH₂CH₂S—CO-i-Pr | —CH₂CH₂S—CO-i-Pr | Me— | C |
| 1587 | m-NH₂ | —CH₂CH₂S—CO-i-Pr | —CH₂CH₂S—CO-i-Pr | Me— | C |
| 1588 | p-NH₂ | —CH₂CH₂S—CO-i-Pr | —CH₂CH₂S—CO-i-Pr | Me— | C |
| 1589 | o-NO₂ | —CH₂CH₂S—CO-i-Pr | —CH₂CH₂S—CO-i-Pr | Me— | C |
| 1590 | m-NO₂ | —CH₂CH₂S—CO-i-Pr | —CH₂CH₂S—CO-i-Pr | Me— | C |
| 1591 | p-NO₂ | —CH₂CH₂S—CO-i-Pr | —CH₂CH₂S—CO-i-Pr | Me— | C |
| 1592 | o-OC₂H₅ | —CH₂CH₂S—CO-i-Pr | —CH₂CH₂S—CO-i-Pr | Me— | C |
| 1593 | m-OC₂H₅ | —CH₂CH₂S—CO-i-Pr | —CH₂CH₂S—CO-i-Pr | Me— | C |
| 1594 | p-OC₂H₅ | —CH₂CH₂S—CO-i-Pr | —CH₂CH₂S—CO-i-Pr | Me— | C |
| 1595 | p-I | —CH₂CH₂S—CO-i-Pr | —CH₂CH₂S—CO-i-Pr | Me— | C |
| 1596 | o-O-n-Pr | —CH₂CH₂S—CO-i-Pr | —CH₂CH₂S—CO-i-Pr | Me— | C |
| 1597 | m-O-n-Pr | —CH₂CH₂S—CO-i-Pr | —CH₂CH₂S—CO-i-Pr | Me— | C |
| 1598 | p-O-n-Pr | —CH₂CH₂S—CO-i-Pr | —CH₂CH₂S—CO-i-Pr | Me— | C |
| 1599 | o-O-i-Pr | —CH₂CH₂S—CO-i-Pr | —CH₂CH₂S—CO-i-Pr | Me— | C |
| 1600 | m-O-i-Pr | —CH₂CH₂S—CO-i-Pr | —CH₂CH₂S—CO-i-Pr | Me— | C |
| 1601 | p-O-i-Pr | —CH₂CH₂S—CO-i-Pr | —CH₂CH₂S—CO-i-Pr | Me— | C |
| 1602 | o-O-n-Bu | —CH₂CH₂S—CO-i-Pr | —CH₂CH₂S—CO-i-Pr | Me— | C |
| 1603 | m-O-n-Bu | —CH₂CH₂S—CO-i-Pr | —CH₂CH₂S—CO-i-Pr | Me— | C |
| 1604 | p-O-n-Bu | —CH₂CH₂S—CO-i-Pr | —CH₂CH₂S—CO-i-Pr | Me— | C |
| 1605 | o-O-i-Bu | —CH₂CH₂S—CO-i-Pr | —CH₂CH₂S—CO-i-Pr | Me— | C |
| 1606 | m-O-i-Bu | —CH₂CH₂S—CO-i-Pr | CH2CH₂S—CO-i-Pr | Me— | C |
| 1607 | p-O-i-Bu | —CH₂CH₂S—CO-i-Pr | —CH₂CH₂S—CO-i-Pr | Me— | C |
| 1608 | o-OCF₃ | —CH₂CH₂S—CO-i-Pr | —CH₂CH₂S—CO-i-Pr | Me— | C |
| 1609 | m-OCF₃ | —CH₂CH₂S—CO-i-Pr | —CH₂CH₂S—CO-i-Pr | Me— | C |
| 1610 | p-OCF₃ | —CH₂CH₂S—CO-i-Pr | —CH₂CH₂S—CO-i-Pr | Me— | C |
| 1611 | H | —CH₂CH₂S—CO-i-Pr | —CH₂CH₂S—CO-i-Pr | —CH₂F | C |
| 1612 | o-OCH₃ | —CH₂CH₂S—CO-i-Pr | —CH₂CH₂S—CO-i-Pr | —CH₂F | C |
| 1613 | m-OCH₃ | —CH₂CH₂S—CO-i-Pr | —CH₂CH₂S—CO-i-Pr | —CH₂F | C |
| 1614 | p-OCH₃ | —CH₂CH₂S—CO-i-Pr | —CH₂CH₂S—CO-i-Pr | —CH₂F | C |
| 1615 | o-Cl | —CH₂CH₂S—CO-i-Pr | —CH₂CH₂S—CO-i-Pr | —CH₂F | C |
| 1616 | m-Cl | —CH₂CH₂S—CO-i-Pr | —CH₂CH₂S—CO-i-Pr | —CH₂F | C |
| 1617 | p-Cl | —CH₂CH₂S—CO-i-Pr | —CH₂CH₂S—CO-i-Pr | —CH₂F | C |
| 1618 | o-Br | —CH₂CH₂S—CO-i-Pr | —CH₂CH₂S—CO-i-Pr | —CH₂F | C |
| 1619 | m-Br | —CH₂CH₂S—CO-i-Pr | —CH₂CH₂S—CO-i-Pr | —CH₂F | C |
| 1620 | p-Br | —CH₂CH₂S—CO-i-Pr | —CH₂CH₂S—CO-i-Pr | —CH₂F | C |
| 1621 | o-NH₂ | —CH₂CH₂S—CO-i-Pr | —CH₂CH₂S—CO-i-Pr | —CH₂F | C |
| 1622 | m-NH₂ | —CH₂CH₂S—CO-i-Pr | —CH₂CH₂S—CO-i-Pr | —CH₂F | C |
| 1623 | p-NH₂ | —CH₂CH₂S—CO-i-Pr | —CH₂CH₂S—CO-i-Pr | —CH₂F | C |
| 1624 | o-NO₂ | —CH₂CH₂S—CO-i-Pr | —CH₂CH₂S—CO-i-Pr | —CH₂F | C |
| 1625 | m-NO₂ | —CH₂CH₂S—CO-i-Pr | —CH₂CH₂S—CO-i-Pr | —CH₂F | C |
| 1626 | p-NO₂ | —CH₂CH₂S—CO-i-Pr | —CH₂CH₂S—CO-i-Pr | —CH₂F | C |
| 1627 | o-OC₂H₅ | —CH₂CH₂S—CO-i-Pr | —CH₂CH₂S—CO-i-Pr | —CH₂F | C |
| 1628 | m-OC₂H₅ | —CH₂CH₂S—CO-i-Pr | —CH₂CH₂S—CO-i-Pr | —CH₂F | C |
| 1629 | p-OC₂H₅ | —CH₂CH₂S—CO-i-Pr | —CH₂CH₂S—CO-i-Pr | —CH₂F | C |
| 1630 | p-I | —CH₂CH₂S—CO-i-Pr | —CH₂CH₂S—CO-i-Pr | —CH₂F | C |
| 1631 | o-O-n-Pr | —CH₂CH₂S—CO-i-Pr | —CH₂CH₂S—CO-i-Pr | —CH₂F | C |
| 1632 | m-O-n-Pr | —CH₂CH₂S—CO-i-Pr | —CH₂CH₂S—CO-i-Pr | —CH₂F | C |
| 1633 | p-O-n-Pr | —CH₂CH₂S—CO-i-Pr | —CH₂CH₂S—CO-i-Pr | —CH₂F | C |
| 1634 | o-O-i-Pr | —CH₂CH₂S—CO-i-Pr | —CH₂CH₂S—CO-i-Pr | —CH₂F | C |
| 1635 | m-O-i-Pr | —CH₂CH₂S—CO-i-Pr | —CH₂CH₂S—CO-i-Pr | —CH₂F | C |
| 1636 | p-O-i-Pr | —CH₂CH₂S—CO-i-Pr | —CH₂CH₂S—CO-i-Pr | —CH₂F | C |
| 1637 | o-O-n-Bu | —CH₂CH₂S—CO-i-Pr | —CH₂CH₂S—CO-i-Pr | —CH₂F | C |
| 1638 | m-O-n-Bu | —CH₂CH₂S—CO-i-Pr | —CH₂CH₂S—CO-i-Pr | —CH₂F | C |
| 1639 | p-O-n-Bu | —CH₂CH₂S—CO-i-Pr | —CH₂CH₂S—CO-i-Pr | —CH₂F | C |
| 1640 | o-O-i-Bu | —CH₂CH₂S—CO-i-Pr | —CH₂CH₂S—CO-i-Pr | —CH₂F | C |
| 1641 | m-O-i-Bu | —CH₂CH₂S—CO-i-Pr | —CH₂CH₂S—CO-i-Pr | —CH₂F | C |
| 1642 | p-O-i-Bu | —CH₂CH₂S—CO-i-Pr | —CH₂CH₂S—CO-i-Pr | —CH₂F | C |
| 1643 | o-OCF₃ | —CH₂CH₂S—CO-i-Pr | —CH₂CH₂S—CO-i-Pr | —CH₂F | C |
| 1644 | m-OCF₃ | —CH₂CH₂S—CO-i-Pr | —CH₂CH₂S—CO-i-Pr | —CH₂F | C |

TABLE 1-continued

| No. | R¹ | R² | R³ | R⁴ | X |
|---|---|---|---|---|---|
| 1645 | p-OCF₃ | —CH₂CH₂S—CO-i-Pr | —CH₂CH₂S—CO-i-Pr | —CH₂F | C |
| 1646 | H | —CH₂CH₂S—CO-i-Pr | —CH₂CH₂S—CO-i-Pr | —CH₂OH | C |
| 1647 | o-OCH₃ | —CH₂CH₂S—CO-i-Pr | —CH₂CH₂S—CO-i-Pr | —CH₂OH | C |
| 1648 | m-OCH₃ | —CH₂CH₂S—CO-i-Pr | —CH₂CH₂S—CO-i-Pr | —CH₂OH | C |
| 1649 | p-OCH₃ | —CH₂CH₂S—CO-i-Pr | —CH₂CH₂S—CO-i-Pr | —CH₂OH | C |
| 1650 | o-Cl | —CH₂CH₂S—CO-i-Pr | —CH₂CH₂S—CO-i-Pr | —CH₂OH | C |
| 1651 | m-Cl | —CH₂CH₂S—CO-i-Pr | —CH₂CH₂S—CO-i-Pr | —CH₂OH | C |
| 1652 | p-Cl | —CH₂CH₂S—CO-i-Pr | —CH₂CH₂S—CO-i-Pr | —CH₂OH | C |
| 1653 | o-Br | —CH₂CH₂S—CO-i-Pr | —CH₂CH₂S—CO-i-Pr | —CH₂OH | C |
| 1654 | m-Br | —CH₂CH₂S—CO-i-Pr | —CH₂CH₂S—CO-i-Pr | —CH₂OH | C |
| 1655 | p-Br | —CH₂CH₂S—CO-i-Pr | —CH₂CH₂S—CO-i-Pr | —CH₂OH | C |
| 1656 | o-NH₂ | —CH₂CH₂S—CO-i-Pr | —CH₂CH₂S—CO-i-Pr | —CH₂OH | C |
| 1657 | m-NH₂ | —CH₂CH₂S—CO-i-Pr | —CH₂CH₂S—CO-i-Pr | —CH₂OH | C |
| 1658 | p-NH₂ | —CH₂CH₂S—CO-i-Pr | —CH₂CH₂S—CO-i-Pr | —CH₂OH | C |
| 1659 | o-NO₂ | —CH₂CH₂S—CO-i-Pr | —CH₂CH₂S—CO-i-Pr | —CH₂OH | C |
| 1660 | m-NO₂ | —CH₂CH₂S—CO-i-Pr | —CH₂CH₂S—CO-i-Pr | —CH₂OH | C |
| 1661 | p-NO₂ | —CH₂CH₂S—CO-i-Pr | —CH₂CH₂S—CO-i-Pr | —CH₂OH | C |
| 1662 | o-OC₂H₅ | —CH₂CH₂S—CO-i-Pr | —CH₂CH₂S—CO-i-Pr | —CH₂OH | C |
| 1663 | m-OC₂H₅ | —CH₂CH₂S—CO-i-Pr | —CH₂CH₂S—CO-i-Pr | —CH₂OH | C |
| 1664 | p-OC₂H₅ | —CH₂CH₂S—CO-i-Pr | —CH₂CH₂S—CO-i-Pr | —CH₂OH | C |
| 1665 | p-I | —CH₂CH₂S—CO-i-Pr | —CH₂CH₂S—CO-i-Pr | —CH₂OH | C |
| 1666 | o-O-n-Pr | —CH₂CH₂S—CO-i-Pr | —CH₂CH₂S—CO-i-Pr | —CH₂OH | C |
| 1667 | m-O-n-Pr | —CH₂CH₂S—CO-i-Pr | —CH₂CH₂S—CO-i-Pr | —CH₂OH | C |
| 1668 | p-O-n-Pr | —CH₂CH₂S—CO-i-Pr | —CH₂CH₂S—CO-i-Pr | —CH₂OH | C |
| 1669 | o-O-i-Pr | —CH₂CH₂S—CO-i-Pr | —CH₂CH₂S—CO-i-Pr | —CH₂OH | C |
| 1670 | m-O-i-Pr | —CH₂CH₂S—CO-i-Pr | —CH₂CH₂S—CO-i-Pr | —CH₂OH | C |
| 1671 | p-O-i-Pr | —CH₂CH₂S—CO-i-Pr | —CH₂CH₂S—CO-i-Pr | —CH₂OH | C |
| 1672 | o-O-n-Bu | —CH₂CH₂S—CO-i-Pr | —CH₂CH₂S—CO-i-Pr | —CH₂OH | C |
| 1673 | m-O-n-Bu | —CH₂CH₂S—CO-i-Pr | —CH₂CH₂S—CO-i-Pr | —CH₂OH | C |
| 1674 | p-O-n-Bu | —CH₂CH₂S—CO-i-Pr | —CH₂CH₂S—CO-i-Pr | —CH₂OH | C |
| 1675 | o-O-i-Bu | —CH₂CH₂S—CO-i-Pr | —CH₂CH₂S—CO-i-Pr | —CH₂OH | C |
| 1676 | m-O-i-Bu | —CH₂CH₂S—CO-i-Pr | —CH₂CH₂S—CO-i-Pr | —CH₂OH | C |
| 1677 | p-O-i-Bu | —CH₂CH₂S—CO-i-Pr | —CH₂CH₂S—CO-i-Pr | —CH₂OH | C |
| 1678 | o-OCF₃ | —CH₂CH₂S—CO-i-Pr | —CH₂CH₂S—CO-i-Pr | —CH₂OH | C |
| 1679 | m-OCF₃ | —CH₂CH₂S—CO-i-Pr | —CH₂CH₂S—CO-i-Pr | —CH₂OH | C |
| 1680 | p-OCF₃ | —CH₂CH₂S—CO-i-Pr | —CH₂CH₂S—CO-i-Pr | —CH₂OH | C |

As for the methods for preparing the compounds of the present invention, the compounds of the general formula (I) wherein both of $R^2$ and $R^3$ are either $C_1$–$C_{22}$ alkyl groups or ethyl groups substituted with one or more halogen atoms can be synthesized, for example, according to the reaction scheme (I) and (2) set out below. In the schemes, $R^1$, $R^4$ and X are the same as those defined above, and $R^5$ represents $C_1$–$C_{22}$ alkyl group or an ethyl group substituted with one or more halogen atoms. The symbol "W" represents a leaving group such as a halogen atom, p-toluenesulfonyloxy group, methanesulfonyloxy group, or trifluoromethanesulfonyloxy group.

<Reaction Scheme (1)>

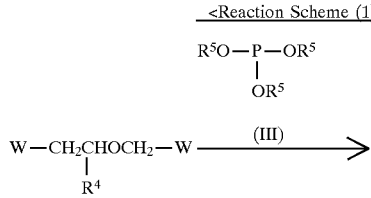

-continued

<Reaction Scheme (1)>

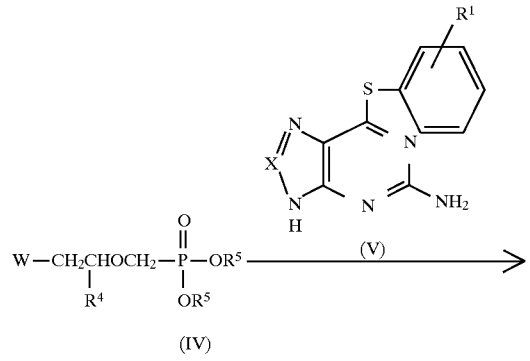

<Reaction Scheme (1)>

-continued

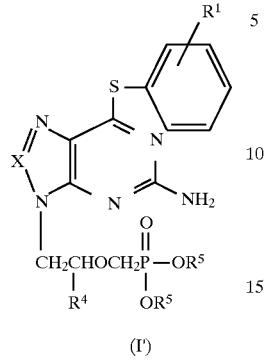

(I')

The compound of the above general formula (II) and the compound of the above general formula (III) are first allowed to react with each other at a temperature of from 10 to 250° C., preferably from 130° to 200° C. for 0.1 to 100 hours, preferably 3 to 24 hours. The compound of the above general formula (IV) obtained by the above reaction may be separated and purified by ordinary separation and purification processes such as distillation, adsorption, and partition chromatography as required. The compound of above general formula (IV) can be subjected to the reaction set out below without purification, although it may be separated and purified as described above. The compound of the above general formula (IV) and the compound of the above general formula (V) are then allowed to react with each other to afford a compound of the above general formula (I') in the presence of a base such as sodium carbonate, potassium carbonate, cesium carbonate, sodium hydride, potassium hydride, triethylamine, or diazabicycloundecene in a suitable solvent such as acetonitrile, tetrahydrofuran, dimethyl sulfoxide, dimethylformamide, or methylpyrrolidone at a temperature of from 10 to 200° C., preferably from 50 to 150° C., for 0.1 to 100 hours, preferably 1 to 10 hours.

Sources of the compound of the above general formula (II) used as the starting material in the reaction scheme (1), the compounds of the above general formula (III), and the compounds of the above general formula (V) are not particularly limited. For example, compounds as commercially available chemical reagents may be used, or alternatively, compounds appropriately prepared by methods per se known in the art can be used. For example, the compound of the formula (V) can be synthesized by heating the compound of the formula (VI) and the compound of the formula (VIII) set out below at a temperature in a range of from 50° to 100° C. in a suitable solvent such as acetonitrile or dimethyl sulfoxide.

The compounds of the above formula (I') can also be prepared according to the scheme described below, wherein $R^1$, $R^4$, $R^5$, X, and W are the same as those defined above.

<Reaction Scheme (2)>

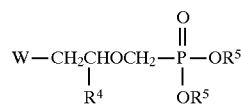

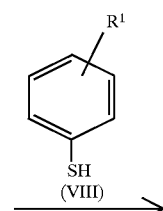
(VI)

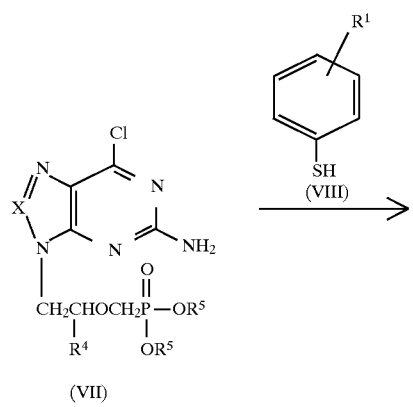

(VII)

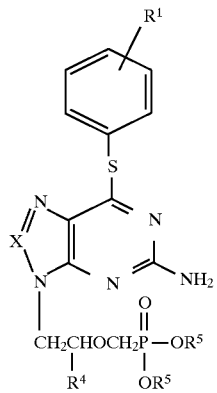

(I')

The compound represented by the above general formula (IV) obtained according to the Reaction Scheme (1) and the compound represented by the above formula (VI) are allowed to react with each other to afford the compound of the above formula (VII) in the presence of a base such as sodium carbonate, potassium carbonate, cesium carbonate, sodium hydride, potassium hydride, triethylamine, or diazabicycloundecene in a suitable solvent such as acetonitrile, tetrahydrofuran, dimethyl sulfoxide, dimethylformamide, or methylpyrrolidone at a temperature of from 10° to 200° C., preferably from 50° to 150° C., for 0.1 to 100 hours, preferably 0.5 to 10 hours. The compound represented by the above formula (VII) and the mercapto compound represented by the above general formula (VIII) or a salt thereof, e.g., sodium salt, potassium salt, lithium salt, triethylamine salt or the like, are allowed to react with each other to afford a compound of the formula (I') in a suitable solvent such as acetonitrile, tetrahydrofuran, dimethyl sulfoxide, dimethylformamide, or methylpyrrolidone, if desired, in the presence of a suitable tertiary amine, at a temperature of from 10° to 200° C., preferably from 70° to 120° C., for 0.1 to 100 hours, preferably 0.5 to 12 hours. These compounds of the formula (I') correspond to compounds of the formula (I) wherein both of $R^2$ and $R^3$ are either $C_1$–$C_{2\,2}$ alkyl groups or ethyl groups substituted with one or more halogen atoms. Sources of the compounds of the above general formula (VI) used as the starting material in the reaction scheme (2) are not particularly limited. For example, compounds as commercially available chemical reagents may be used, or alternatively, compounds appropriately prepared by methods per se known in the art can be used.

The compounds of the formula (I) in which $R^5$ of the formula (I') is converted to other substituents can be prepared by further modifying the phosphate ester part of the compounds of the formula (I'). For example, compounds of the formula (I) wherein both of $R^2$ and $R^3$ are hydrogen atoms can be obtained by hydrolyzing a compound of the above general formula (I'). Compounds of the formula (I) wherein $R^3$ is hydrogen atom, a $C_1$–$C_{2\,2}$ alkyl group, an acylthioethyl group, or an ethyl group substituted with one or more halogen atoms and $R^2$ is a $C_1$–$C_{2\,2}$ alkyl group or an ethyl group substituted with one or more halogen atoms can be prepared by reacting a compound of the formula (I') with a compound of the following formula (IX); $R^6OH$ wherein $R^6$ represents hydrogen atom, a $C_1$–$C_{2\,2}$ alkyl group, an acylthioethyl group, or an ethyl group substituted with one or more halogen atoms, in the absence or presence of a suitable solvent, e.g., a chlorinated solvent such as dichloromethane, pyridine, acetonitrile, tetrahydrofuran, dimethyl sulfoxide, dimethylformamide, methylpyrrolidone or the like, if desired, in the presence of an acid or an alkali, at a temperature of from 10° to 100° C., preferably from 20° to 30° C., for 0.1 to 100 hours, preferably 5 to 12 hours.

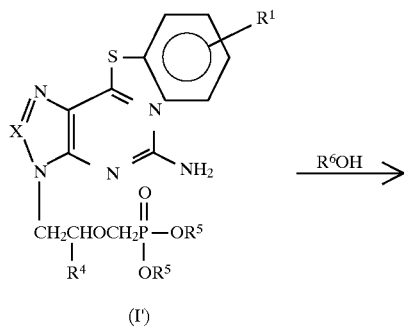

(I')

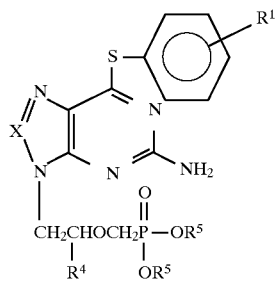

In the above scheme, $R^1$, $R^4$, $R^5$, $R^6$, and X are the same as those defined above.

The compounds represented by the above general formula (I) wherein $R^2$ and $R^3$ independently represent hydrogen atom, a $C_1$–$C_{2\,2}$ alkyl group, an acylthioethyl group, or an ethyl group substituted with one or more halogen atoms can also be obtained according to the method described below. In the following scheme, $R^1$, $R^4$, and X are the same as those defined above, and $R^7$ and $R^8$ independently represent hydrogen atom, $C_1$–$C_{2\,2}$ alkyl group, an acylthioethyl group, or an ethyl group substituted with one or more halogen atoms, with the proviso that $R^7$ and $R^8$ do not simultaneously represent hydrogen atoms.

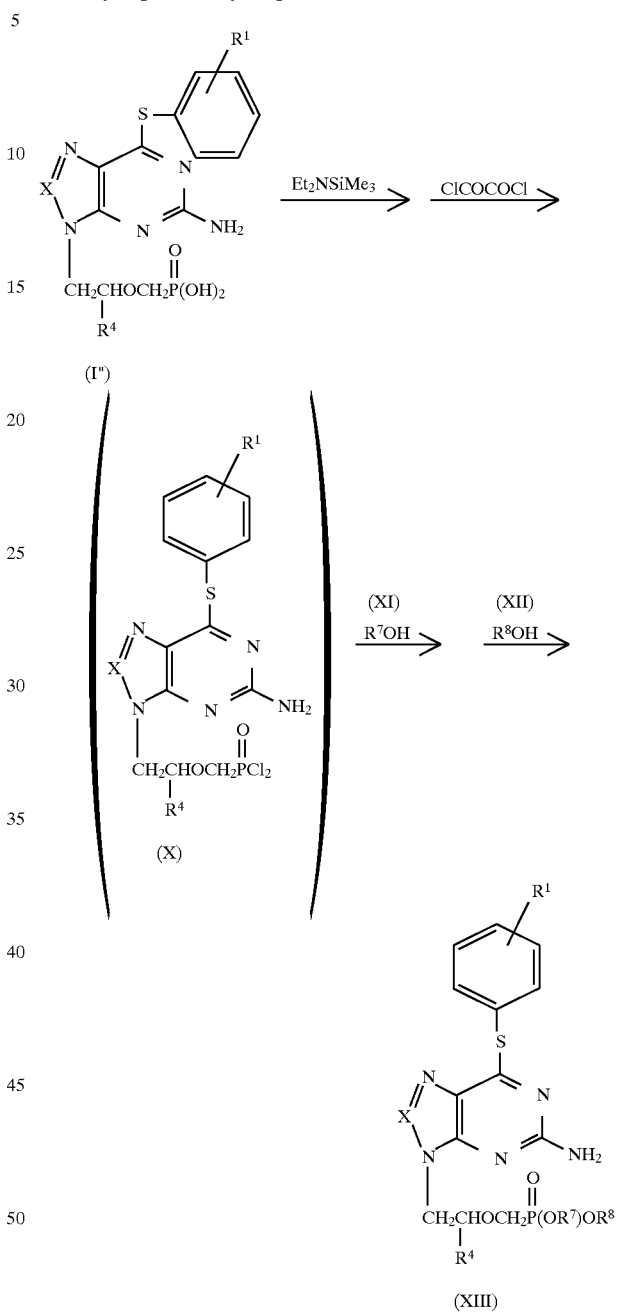

The compound of the general formula (I'') and trimethylsilyldie thylamine are first subjected to a reaction in a suitable solvent, e.g., a chlorinated solvent such as dichloromethane, dichloroethane, or chloroform at room temperature for approximately 1 hour. In the reaction, trimethylsilyldiethylamine is used in an amount of at least 2 moles based on 1 mole of the compound of the above general formula (I''). After the reaction mixture is concentrated to dryness, a resulting residue is dissolved in a chlorinated solvent such as dichloromethane, and then oxalyl chloride is added in an amount of at least 2 moles based on 1 mole of the compound of the formula (I''). The mixture is subjected to a reaction in the presence of catalytic amount of dimethylformamide for approximately 1 hour under ice cooling and then about one hour at room temperature.

The compound of the formula (X) obtained after the evaporation of the solvent is allowed to react, generally without purification, with the compound of the formula (XI) and/or the compound of the formula (XII) in a suitable solvent, e.g., a chlorinated solvent such as dichloromethane, pyridine, acetonitrile, tetrahydrofuran, dimethyl sulfoxide, dimethylformamide, methylpyrrolidone or the like, at a temperature of from 10° to 100° C., preferably from 20° to 30° C. for 0.1 to 100 hours, preferably 5 to 12 hours. The resulting compounds of the formula (XIII) correspond to the compounds of the formula (I) wherein $R^2$ and $R^3$ independently represent hydrogen atom, a $C_1$–$C_{22}$ alkyl group, acylthioethyl group, or an ethyl group substituted with one or more halogen atoms, with the proviso that $R^2$ and $R^3$ do not simultaneously represent hydrogen atoms. The compounds of the formula (I") used as the starting material in the above reaction can be obtained by hydrolyzing the compounds of the formula (I') as described previously, or alternatively, the compounds can be efficiently obtained by reacting compounds of the formula (I') wherein $R^5$ is a $C_1$–$C_{22}$ alkyl group with triethyliodosilane, trimethylbromosilane or the like.

The compounds of the formula (I) wherein both of $R^2$ and $R^3$ are acyloxymethyl groups or the compounds wherein one of $R^2$ and $R^3$ is an acyloxymethyl group and the other is hydrogen atom can be prepared by reacting a compound of the above formula (I") with an acyloxymethyl halide represented by the following formula (XIV): $R^9Y$ wherein $R^9$ represents an acyloxymethyl group and Y represents a chlorine atom, a bromine atom, or an iodine atom, in the presence of a base such as sodium carbonate, potassium carbonate, cesium carbonate, sodium hydride, potassium hydride, triethylamine, pyridine, diazabicycloundecene, or N,N'-cyclohexyl-4-morpholine-carboxamidine in a suitable solvent such as acetonitrile, tetrahydrofuran, dimethyl sulfoxide, dimethylformamide, or methylpyrrolidone at a temperature of from 0° to 200° C., preferably 10° to 100° C., for 1 to 300 hours, preferably 10 to 200 hours. Where both of $R^2$ and $R^3$ are acyloxymethyl groups, 2 moles of the compound the formula (XIV) based on the compound of the formula (I") may be subjected to the reaction, and where only one of them is an acyloxymethyl group, an equimolar amount may be subjected to the reaction.

Compounds of the formula (I) wherein one of $R^2$ and $R^3$ is an acyloxymethyl group and the other is a $C_1$–$C_{22}$ alkyl group, acylthioethyl group, or an ethyl group substituted with one or more halogen atoms can be prepared by first synthesizing compounds wherein one of $R^2$ and $R^3$ is a $C_1$–$C_{22}$ alkyl group, an acylthioethyl group, or an ethyl group substituted with one or more halogen atoms and the other is hydrogen atom, and then these compounds are subjected to reactions with the compounds of the formula (XIV) according to the method described above.

Salts of the compounds of the formula (I) can be prepared, for example, by the following processes: reacting the compound of the formula (I') with a corresponding acid with stirring at a temperature of from −10° to 100° C., preferably from 10° to 50° C., for 0.1 to 20 hours, preferably 0.3 to 1 hour in a suitable solvent such as ethyl acetate, isopropanol, acetonitrile, tetrahydrofuran, dimethyl sulfoxide, dimethylformamide, or methylpyrrolidone.

The aforementioned processes are described solely by way of examples for the preparations of the compounds of the present invention represented by the formula (I), and the processes for preparing the compounds of the present invention are not limited to these processes. More specific explanations will be given in Examples of the specification as for the processes for preparing the compounds of the present invention. Therefore, one of ordinarily skilled artisan can prepare compounds that fall within the scope of the above formula (I) according to the foregoing general explanations and specific descriptions in Examples, and applying appropriate alterations and modifications thereto, if necessary. The compounds of the above general formula (I) obtained according to the aforementioned processes and salts thereof can be separated and purified by applying ordinary separation and purification procedures for nucleotides, e.g., recrystallization, adsorption, ion exchange, partition chromatography or the like.

The compounds of the present invention are useful as active ingredients of medicaments, and more specifically, useful as an active ingredient of antiviral agents as demonstrated by the test examples set out below. In addition, their anti-tumor activities are expected as verified with regard to other ionic phosphonate nucleotide analogues. Although viruses applicable by the medicament of the present invention are not particularly limited, specific examples include RNA viruses such as human immunodeficiency virus, influenza virus, or hepatitis C virus, and DNA viruses such as herpes simplex virus I, herpes simplex virus II, Cytomegalovirus, vericello-herpes zoster virus, or hepatitis B virus, and a more preferred example includes hepatitis B virus.

When the compounds of the present invention are used as medicaments, the compounds, per se, may be administered. However, it is preferred that pharmaceutical compositions comprising the aforementioned compounds as active ingredients may be manufactured by using pharmaceutically acceptable additives and subjected to administration. Components of the pharmaceutical composition may be determined depending on solubility and chemical properties of the compound, an administration route, an administration protocol and the like. For example, formulations in a form of granules, subtilized granules, powder, tablets, hard syrup, soft capsules, troches, syrup, emulsion, soft gelatin capsules, gel, paste, suspension, liposome suspension or the like may be orally administered, or alternatively, injectable formulations may be administered intravenously, intramuscularly, or subcutaneously. A powder for injection may be used after preparing an injectable formulation just before use.

As the pharmaceutically acceptable additives, organic or inorganic solid or liquid carriers may be used which are suitable for oral, enteral, parenteral or topical administrations. Examples of the solid carriers used for the preparation of solid formulations include lactose, sucrose, starch, talc, cellulose, dextrin, china clay, calcium carbonate, agar, pectin, stearic acid, magnesium stearate, lecithin, sodium chloride and the like. Examples of the liquid carriers for the preparation of liquid formulations for oral administration include glycerin, peanut oil, polyvinylpyrrolidone, olive oil, ethanol, benzyl alcohol, propylene glycol, physiological saline, and water. In addition to the carriers mentioned above, the pharmaceutical composition may contain, for example, additives such as moistening agents, suspension aids, sweetening agents, flavoring agents, colorants, and preservatives. Liquid formulations may be filled in capsules made of absorbable material such as gelatin. Examples of solvents or suspending mediums for the preparation of formulations for parenteral administration, i.e., injections, include water, propylene glycol, polyethylene glycol, benzyl alcohol, ethyl oleate, and lecithin.

The compounds of the present invention, in particular, the ester derivatives represented by the above formula (I'), have excellent oral absorbabilities as demonstrated in the test examples set out below. Therefore, oral administration is a preferred administration route for the medicament of the present invention. Manufacture of the aforementioned formulations can be carried out according to ordinary methods. Clinical dose of the medicament of the present invention may generally be, for the use of an oral administration, 0.1 to 500 mg/kg, preferably 1 to 50 mg/kg per day for an adult as the weight of the compound of the present invention. However, the aforementioned dose may be appropriately increased or decreased depending on age, conditions or symptoms, or the presence or absence of a co-administered drug. The above daily dose may be administered once a day, or dividedly administered twice or several times a day with appropriate intervals. A continual administration may be carried out at intervals of several days. For an administration by an injection, dose may be 0.01 to 50 mg/kg, preferably 0.1 to 5 mg/kg per day for an adult as the weight of the compound of the present invention.

EXAMPLES

The present invention will be more specifically explained by referring to the following examples. However, the scope of the present invention is not limited to the examples set out below. Compound numbers in the examples correspond to those listed in Table 1.

Example 1

Preparation of 2-amino-9-[2-[bis(2,2,2-trifluoroethyl)-phosphonylmethoxy]ethyl]-6-phenylthiopurine (Compound No. 1)

2-Chloroethyl chloromethyl ether (87 g, 670 mmol) and Tris(2,2,2-trifluoroethyl)phosphite (200 g, 610 mmol) were heated at 160° C. for 7 hours to obtain 2-[bis(2,2,2-trifluoroethyl) phosphonylmethoxy]ethyl chloride quantitatively.

2-[Bis(2,2,2-trifluoroethyl)phosphonylmethoxy]ethyl chloride (206 g) was dissolved in methyl ethyl ketone (2,000 ml) and the solution was heated under reflux with sodium iodide (270 g) for 8 hours. After completion of the reaction, the mixture was cooled to room temperature and concentrated to dryness. The residue was dissolved in chloroform/hexane and adsorbed on a silica gel column, and then eluted with chloroform/hexane to give 2-[bis(2,2,2-trifluoroethyl)-phosphonylmethoxy]ethyl iodide quantitatively.

2-Amino-6-chloropurine (15.0 g, 88 mmol) was suspended in dimethylformamide (360 ml) and treated with 1,8-diazabicyclo[5.4.0]-undec-7-ene (13.9 ml, 93 mmol) at 80° C. for 1 hour. Then, 2-[bis(2,2,2-trifluoroethyl) phosphonylmethoxy]ethyl iodide (23.8 ml) was added to the reaction mixture and subjected to a reaction at 100° C. for 5 hours. After completion of the reaction, the mixture was cooled to room temperature and concentrated to dryness. The residue was dissolved in chloroform and adsorbed on a silica gel column, and then eluted with 5%-methanol in chloroform to give 2-amino-9-[2-[bis(2,2,2-trifluoroethyl) phosphonylmethoxy]ethyl-6-chloropurine (23.3 g, yield 56%).

Triethylamine (2.1 ml) and thiophenol (3.1 ml) were added to a solution of 2-amino-9-[2-[bis(2,2,2-trifluoroethyl)phosphonyl-methoxy]ethyl]-6-chloropurine (7.1 g) in dimethylformamide (68 ml) and the mixture was stirred at 100° C. for 2 hours. The reaction mixture was cooled to room temperature and concentrated to dryness. The residue was dissolved in chloroform and adsorbed on a silica gel column, and then eluted with 5%-methanol in chloroform to give 2-amino-9-[2-[bis(2,2,2-trifluoroethyl) phosphonylmethoxy]ethyl]-6-phenylthiopurine (5.0 g, yield 61%).

m.p.:105°–106° C. (ethanol)
$^1$H-NMR(CDCl$_3$, δ): 3.86–4.03(m,4H), 4.20–4.50(m,6H), 4.77(s,2H), 7.42–7.58(m,3H), 7.58–7.68(m,2H), 7.72(s,1H)

Example 2

Preparation of 2-amino-9-[2-[bis(2,2,2-trifluoroethyl)-phosphonylmethoxy]ethyl]-6-p-nitrophenylthiopurine (Compound No. 16)

The title compound was obtained in a similar manner to Example 1 except that p-nitrothiophenol was used instead of thiophenol used in Example 1.
m. p.:114°–116° C. (diisopropyl ether)
$^1$H-NMR(CDCl$_3$, δ): 3.87–4.02(m,4H), 4.22–4.46(m,6H), 4.83(s,2H), 7.75–7.85(m,2H), 8.20–8.28(m,2H)

Example 3

Preparation of 2-amino-9-[2-[bis(2,2,2-trifluoroethyl)-phosphonylmethoxy]ethyl]-6-p-methoxyphenylthiopurine (Compound No. 4)

The title compound was obtained in a similar manner to Example 1 except that p-methoxythiophenol was used instead of thiophenol used in Example 1.
m.p.:93°–95° C. (diisopropyl ether)
$^1$H-NMR(CDCl$_3$, δ): 3.85(s,3H), 3.92–4.00(m,4H), 4.24–4.45(m,6H), 4.75(s,2H), 6.95(d,J=9.0 Hz,2H), 7.53(d, J=9.0 Hz,2H), 7.71(s,1H)

Example 4

Preparation of 2-amino-9-[2-[bis(2,2,2-trifluoroethyl)-phosphonylmethoxy]ethyl]-6-m-methoxyphenylthiopurine (Compound No. 3)

The title compound was obtained in a similar manner to Example 1 except that m-methoxythiophenol was used instead of thiophenol used in Example 1.
UV: $\lambda_{max}$=291, 328 (0.01N—HCl/CH$_3$OH)
$\lambda_{max}$=242, 315 (0.01N—NaOH/CH$_3$OH)
$^1$H-NMR(CDCl$_3$, δ): 3.82(s,3H), 3.88–8.97(m,4H), 4.24–4.45(m,6H), 4.81(s,2H), 6.92–7.00(m,1H), 7.18–7.40 (m,4H), 7.72(s,1H)

Example 5

Preparation of 2-amino-9-[2-[bis(2,2,2-trifluoroethyl)-phosphonylmethoxy]ethyl]-6-o-methoxyphenylthiopurine (Compound No. 2)

The title compound was obtained in a similar manner to Example 1 except that o-methoxythiophenol was used instead of thiophenol used in Example 1.
UV: $\lambda_{max}$=332 (0.01N—HCl/CH$_3$OH)
$\lambda_{max}$=314 (0.01N—NaOH/CH$_3$OH)
$^1$H-NMR(CDCl$_3$, δ): 3.80(s,3H), 3.85–3.98(m,4H), 4.20–4.46(m,6H), 4.78(s,2H), 6.96–7.04(m,2H), 7.43(ddd, J=7.7, 7.7, and 1.5 Hz,1H), 7.59(dd,J=7.6 and 1.5 Hz,1H), 7.69(s,1H)

Example 6

Preparation of 2-amino-9-[2-[bis(2,2,2-trifluoroethyl)-phosphonylmethoxy]ethyl]-6-p-aminophenylthiopurine (Compound No. 13)

The title compound was obtained in a similar manner to Example 1 except that p-aminothiophenol was used instead of thiophenol used in Example 1.

m.p.:130–132° C. (diisopropyl ether)
$^1$H-NMR(CDCl$_3$, δ): 3.86–4.00(m,4H), 4.21–4.48(m,6H), 4.80(s,2H), 6.71(d,J=8.5 Hz,2H), 7.38(d,J=8.5 Hz,2H), 7.70 (s,1H)

Example 7

Preparation of 2-amino-9-[2-[bis(2,2,2-trifluoroethyl)-phosphonylmethoxy]ethyl]-6-p-chlorophenylthiopurine (Compound No. 7)

The title compound was obtained in a similar manner to Example 1 except that p-chlorothiophenol was used instead of thiophenol used in Example 1.
m. p.: 108–110° C. (diisopropyl ether/hexane)
$^1$H-NMR(CDCl$_3$, δ): 3.87–4.00(m,4H), 4.22–4.47(m,6H), 4.77(s,2H), 7.39(d,J=8.5 Hz,2H), 7.56(d,J=8.5 Hz,2H), 7.76 (s,1H)

Example 8

Preparation of 2-amino-9-[2-[bis(2,2,2-trifluoroethyl)-phosphonylmethoxy]ethyl]-6-p-ethoxyphenylthiopurine (Compound No. 19)

p-Hydroxybenzenethiol (25 g) was dissolved in DMSO (155 ml) and the solution was stirred for 4 hours and poured into ice water (1 L). The precipitated crystals were dried under reduced pressure to give bis(p-hydroxyphenyl) disulfide quantitatively.

Potassium carbonate (2.2 g) and ethyl iodide (4.3 g) were added to a solution of bis(p-hydroxyphenyl)disulfide (2.0 g) in DMF (20 ml), and the mixture was stirred at 70° C. for 16 hours and poured into ice water (100 ml). The mixture was extracted with hexane (500 ml) and concentrated to give bis(p-ethoxyphenyl)disulfide (1.8 g, 82%).

Triphenylphosphine (1.9 g) and concentrated hydrochloric acid (3 drops) were added to a solution of bis(p-ethoxyphenyl)disulfide (1.8 g) in 1,4-dioxane (20 ml) and water (5 ml). After stirring at 40° C. for 10 hours, the mixture was poured into chloroform (250 ml). After washing twice with water, the organic layer was concentrated to give p-ethoxybenzenethiol quantitatively. The title compound was obtained in a similar manner to Example 1 except that p-ethoxybenzenethiol was used instead of thiophenol.
m.p.: 61–64° C. (chloroform)
$^1$H-NMR(CDCl$_3$, δ): 1.45(t,J=7.0 Hz,3H), 3.84–3.98(m, 4H), 4.08(q,J=7.0 Hz,2H), 4.18–4.48(m,6H), 4.76(s,2H), 6.94(d,J=8.4 Hz,2H), 7.52(d,J=8.4 Hz,2H), 7.71(s,1H)

Example 9

Preparation of 2-amino-9-[2-[bis(2,2,2-trifluoroethyl)-phosphonylmethoxy]ethyl]-6-p-butoxyphenylthiopurine (Compound No. 29)

The title compound was obtained in a similar manner to Example 2 except that butyl iodide was used instead of ethyl iodide.
m.p.: 89–92° C. (chloroform)
$^1$H-NMR(CDCl$_3$, δ): 0.99(t,J=7.5 Hz,3H), 1.51(tq,J=8.1 Hz and 7.5 Hz,2H), 1.79(tt,J=6.4 Hz and 8.1 Hz,2H), 3.84–3.98 (m,4H), 4.00(t,J=6.4 Hz,2H), 4.20–4.48(m,6H), 4.76(s,2H), 6.94(d,J=8.8 Hz,2H), 7.52(d,J=8.8 Hz,2H), 7.71(s,1H)

Example 10

Preparation of 2-amino-9-[2-[bis(2,2,2-trifluoroethyl)-phosphonylmethoxy]ethyl]-6-p-propoxyphenylthiopurine (Compound No. 23)

The title compound was obtained in a similar manner to Example 8 except that propyl iodide was used instead of ethyl iodide.
UV: λ$_{max}$=229, 331 (0.01N—HCl/CH$_3$OH)
λ$_{max}$=223, 314 (0.01N—NaOH/CH$_3$OH)
$^1$H-NMR(CDCl$_3$, δ): 1.05(t,J=7.4 Hz,3H), 1.84(tq,J=6.8 Hz and 7.4 Hz,2H), 3.82–4.00(m,6H), 4.20–4.48(m,6H), 4.78 (s,2H), 6.95(d,J=8.7 Hz,2H), 7.51(d,J=8.7 Hz,2H), 7.71(s, 1H)

Example 11

Preparation of 2-amino-9-[2-[bis(2,2,2-trifluoroethyl)-phosphonylmethoxy]ethyl]-6-p-isopropoxyphenylthiopurine (Compound No. 26)

The title compound was obtained in a similar manner to Example 8 except that p-isopropyl iodide was used instead of ethyl iodide.
UV: λ$_{max}$=230, 330 (0.01N—HCl/CH$_3$OH)
λ$_{max}$=223, 314 (0.01N—NaOH/CH$_3$OH)
$^1$H-NMR(CDCl$_3$, δ): 1.37(d,J=6.0 Hz,6H), 3.85–3.98(m, 4H), 4.18–4.48(m,6H), 4.60(septet,J=6.0 Hz,1H), 4.77(s, 2H), 6.93(d,J=8.7 Hz,2H), 7.51(d,J=8.7 Hz,2H), 7.71(s,1H)

Example 12

Preparation of 2-amino-9-[2-[bis(2,2,2-trifluoroethyl)-phosphonylmethoxy]ethyl]-6-p-isobutoxyphenylthiopurine (Compound No. 32)

The title compound was obtained in a similar manner to Example 8 except that p-isobutyl iodide was used instead of ethyl iodide.
UV: λ$_{max}$=230, 331 (0.01N—HCl/CH$_3$OH)
λ$_{max}$=223, 314 (0.01N—NaOH/CH$_3$OH)
$^1$H-NMR(CDCl$_3$, δ): 1.05(d,J=6.8 Hz,6H), 2.13(apparent quintet,J=6.5 Hz,1H), 3.76(d,J=6.5 Hz,2H), 3.83–3.97(m, 4H), 4.20–4.45(m,6H), 4.77(s,2H), 6.94(d,J=8.9 Hz,2H), 7.52(d,J=8.9 Hz,2H), 7.71(s,1H)

Example 13

Preparation of 2-amino-9-[2-[bis(2,2,2-trifluoroethyl)-phosphonylmethoxy]ethyl]-6-p-trifluoromethoxyphenylthiopurine (Compound No. 35)

Zinc powder (3.1 g) was added to a suspension of p-trifluoromethoxybenzenesulfonyl chloride (1.36 ml) in concentrated sulfuric acid (3.4 ml) and water (20 ml), and the suspension was stirred at 0° C. for 18 hours and heated under reflux for 6 hours. The mixture was added with ethyl acetate, washed with water, saturated aqueous solution of sodium hydrogen carbonate, and saturated brine, and then concentrated under reduced pressure to give p-trifluoromethoxybenzenethiol (0.73 g, 47%).

The title compound was obtained in a similar manner to Example 1 except that p-trifluoromethoxybenzenethiol was used instead of thiophenol.
m.p.: 128–130° C. (chloroform)
$^1$H-NMR(CDCl$_3$, δ): 3.86–3.98(m,4H), 4.22–4.48(m,6H), 4.78(s,2H), 7.27(d,J=8.7 Hz,2H), 7.66(d,J=8.7 Hz,2H), 7.73 (s,1H)

Example 14

Preparation of 2-amino-9-[2-[(2,2,2-trifluoroethyl)-phosphonylmethoxy]ethyl]-6-phenylthiopurine (Compound No. 211)

1N aqueous solution of sodium hydroxide (82 μl) was added to a solution of 2-amino-9-[2-[bis(2,2,2-trifluoroethyl)

phosphonylmethoxy]ethyl]-6-phenylthiopurine (45 mg) in tetrahydrofuran (0.3 ml), and the mixture was stirred for 30 minutes and then lyophilized to give 2-amino-9-[2-[phosphonylmethoxy]ethyl]-6-phenylthiopurine (37 mg, 93%).

UV: $\lambda_{max}$=325 (0.1N—HCl/CH$_3$OH)
$\lambda_{max}$=244, 316 (0.1N—NaOH/CH$_3$OH)
$^1$H-NMR(D$_2$O, δ): 3.63(d,J=8.8 Hz,2H), 3.81–4.04(m,4H), 4.23–4.34(m,2H), 7.40–7.66(m,5H), 8.01(s,1H)

Example 15

Preparation of 2-amino-9-[2-[(2,2,2-trifluoroethyl)-phosphonylmethoxy]ethyl]-6-p-methoxyphenylthiopurine (Compound No. 214)

The title compound was obtained in a similar manner to Example 14 except that 2-amino-9-[2-[bis(2,2,2-trifluoroethyl) phosphonylmethoxy]ethyl]-6-p-methoxyphenylthiopurine was used instead of 2-amino-9-[2-[bis(2,2,2-trifluoroethyl) phosphonylmethoxy]-ethyl]-6-phenylthiopurine.

UV: $\lambda_{max}$=230, 328 (0.1N—HCl/CH$_3$OH)
$\lambda_{max}$=223, 314 (0.01N—NaOH/CH$_3$OH) $^1$H-NMR(D$_2$O, δ): 3.69(d,J=8.8 Hz,2H), 3.82–4.06(m involving s at 3.87, 7H), 4.28–4.38(m,2H), 7.05(d,J=8.7 Hz,2H), 7.51(d,J=8.7 Hz,2H), 8.04(s,1H)

Example 16

Preparation of 2-amino-9-[2-[phosphonylmethoxy] ethyl]-6-phenylthiopurine (Compound No. 281)

2-Amino-9-[2-[diethylphosphonylmethoxy]ethyl]-6-phenylthiopurine was obtained in a similar manner to Example 1 except that triethylphosphite was used instead of tris(2,2,2-trifluoroethyl)phosphite.

Bromotrimethylsilane (2.6 ml) was added to a solution of 2-amino-9-[2-[diethylphosphonylmethoxy]ethyl]-6-phenylthiopurine (1.75 g) in acetonitrile (20 ml) and the mixture was stirred at 25° C. for 22 hours. The mixture was added with water and concentrated to dryness, and the product was crystallized from acetone/methanol to give 2-amino-9-[2-[phosphonylmethoxy]ethyl]-6-phenylthiopurine (406 mg, 27%).

m.p.: 163–168° C. (dec. acetone/methanol)
$^1$H-NMR(DMSO-d$_6$, δ): 3.58(d,J=8.7 Hz,2H), 3.81(t,J=5.1 Hz,2H), 4.19(t,J=5.1 Hz,2H), 7.40–7.50(m,3H), 7.55–7.66 (m,2H), 8.02(s,1H)

Example 17

Preparation of 2-amino-9-[2-phosphonylmethoxyethyl]-6-p-methoxyphenylthiopurine (Compound No. 284)

The title compound was obtained in a similar manner to Example 16 except that p-methoxythiophenol was used instead of thiophenol.

UV: $\lambda_{max}$=230, 328 (0.1N—HCl/CH$_3$OH)
$\lambda_{max}$=223, 314 (0.01N—NaOH/CH$_3$OH)
$^1$H-NMR(DMSO-d$_6$, δ): 3.58(d,J=8.6 Hz,2H), 3.78–3.92 (m involving s at 3.79,5H), 4.18–4.30(m,2H), 7.02(d,J=8.7 Hz,2H), 7.51(d,J=8.7 Hz,2H), 8.14(s,1H)

Example 18

Preparation of 2-amino-9-[2-[bis(2,2,2-trifluoroethyl)-phosphonylmethoxy]ethyl]-6-p-methoxyphenylthiopurine hydrochloride A solution of 2-amino-9-[2-[bis(2,2,2-trifluoroethyl) phosphonylmethoxy]ethyl]-6-p-methoxyphenylthiopurine in ethyl acetate was added dropwise to a solution of hydrogen chloride in ethyl acetate and the mixture was stirred for 30 minutes. The precipitated crystals were dried under reduced pressure to give 2-amino-9-[2-[bis(2,2,2-trifluoroethyl)phosphonylmethoxy]ethyl]-6-p-methoxyphenylthiopurine hydrochloride.

m.p.: 110–115° C. (dec. ethyl acetate)
$^1$H-NMR(DMSO-d$_6$, δ): 3.79(s,3H), 3.87(t,J=4.8 Hz,2H), 4.13(d,J=7.9 Hz,2H), 4.23(t,J=4.8 Hz,2H), 4.55–4.75(m, 4H), 7.02(d,J=8.7 Hz,2H), 7.49(d,J=8.7 Hz,2H), 8.13(s,1H)

Example 19

Preparation of 2-amino-9-[2-[bis(2,2,2-trifluoroethyl)-phosphonylmethoxy]ethyl]-6-m-methoxyphenylthiopurine hydrochloride A solution of 2-amino-9-[2-[bis(2,2,2-trifluoroethyl) phosphonylmethoxy]ethyl]-6-m-methoxyphenylthiopurine in ethyl acetate was added dropwise to a solution of hydrogen chloride in ethyl acetate and the mixture was stirred for 30 minutes. The precipitated crystals were dried under reduced pressure to give 2-amino-9-[2-[bis(2,2,2-trifluoroethyl)phosphonylmethoxy]ethyl]-6-m-methoxyphenylthiopurine hydrochloride.

m.p.: 130–135° C. (dec. ethyl acetate)
$^1$H-NMR(DMSO-d$_6$, δ): 3.77(s,3H), 3.84–3.96(m,2H), 4.14 (d,J=8.0 Hz,2H), 4.20–4.36(m,2H), 4.56–4.76(m,4H), 6.99–7.08(m,1H), 7.12–7.24(m,2H), 7.36(dd,J=7.8 Hz and 8.3 Hz,1H), 8.28(s,1H)

Example 20

Preparation of 2-amino-9-[2-[bis(2,2,2-trifluoroethyl)-phosphonylmethoxy]ethyl]-6-o-methoxyphenylthiopurine hydrochloride A solution of 2-amino-9-[2-[bis(2,2,2-trifluoroethyl) phosphonylmethoxy]ethyl]-6-o-methoxyphenylthiopurine in ethyl acetate was added dropwise to a solution of hydrogen chloride in ethyl acetate and the mixture was stirred for 30 minutes. The precipitated crystals were dried under reduced pressure to give 2-amino-9-[2-[bis(2,2,2-trifluoroethyl)phosphonylmethoxy]ethyl]-6-o-methoxyphenylthiopurine hydrochloride.

m.p.: 101–106° C. (dec. ethyl acetate)
$^1$H-NMR(DMSO-d$_6$, δ): 3.74(s,3H), 3.84–3.98(m,2H), 4.14 (d,J=7.9 Hz,2H), 4.20–4.34(m,2H), 4.56–4.76(m,4H), 7.01 (dd,J=7.5 Hz,1H), 7.14(d,J=8.4 Hz,1H), 7.42–7.60(m,2H), 8.27(s,1H)

Example 21

Preparation of 2-amino-9-[2-[bis(2,2,2-trifluoroethyl)-phosphonylmethoxy]propyl]-6-phenylthiopurine (Compound No. 351)

1-Chloro-2-propanol (25 ml) and paraformaldehyde (11 g) were suspended in dichloromethane (50 ml), and the suspension was cooled to 0° C. and stirred for 10 hours with hydrogen chloride gas bubbling. After evaporation of dichloromethane, the residue was added with tris(2,2,2-trifluoroethyl)phosphite (86.5 g) and heated at 160° C. for 5 hours. The reaction mixture was evaporated under reduced pressure to give 2-[bis(2,2,2-trifluoroethyl)-phosphonylmethoxy]propyl chloride.

2-Amino-6-chloropurine (15.0 g, 88 mmol) was suspended in dimethylformamide (360 ml) and reacted with 1,8-diazabicyclo[5.4.0]-undec-7-ene (13.9 ml, 93 mmol) at 80° C. for 1 hour. Then, 2-[bis(2,2,2-trifluoroethyl) phosphonylmethoxy]propyl chloride (36.1 g) was added to the above reaction mixture and subjected to a reaction at 100° C. for 2 hours. After completion of the reaction, the mixture was cooled to room temperature and concentrated. The residue was added with water and extracted with ethyl acetate. After the organic layer was dried over magnesium sulfate, the layer was concentrated to give syrup. The resulting syrup was dissolved in ether and insoluble materials were removed to give 2-amino-9-[2-[bis(2,2,2-trifluoroethyl)phosphonylmethoxy]propyl]-6-chloropurine (6 g).

Triethylamine (1.1 ml) and thiophenol (1.53 ml) were added to a solution of 2-amino-9-[2-[bis(2,2,2-trifluoroethyl)-phosphonylmethoxy]propyl]-6-chloropurine (3.0 g) in dimethylformamide (25 ml) and the mixture was stirred at 100° C. for 2 hours. The reaction mixture was cooled to room temperature and concentrated. The residue was added with an aqueous sodium hydrogen carbonate and extracted with ethyl acetate, and the organic layer was concentrated. The residue was dissolved in chloroform and adsorbed on a silica gel column, and then eluted with 2%-methanol in chloroform to give 2-amino-9-[2-[bis(2,2,2-trifluoroethyl)phosphonylmethoxy]propyl]-6-phenylthiopurine (0.77 g, yield 22%).
m.p.: 119–120° C. (isopropyl ether)
$^1$H-NMR(CDCl$_3$, δ): 1.25(d,J=5.9 Hz,3H), 3.76–4.23(m, 5H), 4.28–4.42(m,4H), 4.77(s,2H), 7.40–7.43 (m,3H), 7.62–7.65(m,2H), 7.72(s,1H)

Example 22

Preparation of 2-amino-9-[2-[bis(2,2,2-trifluoroethyl)-phosphonylmethoxy]propyl]-6-p-methoxyphenylthiopurine (Compound No. 354)

The title compound was obtained in a similar manner to Example 21 except that p-methoxythiophenol was used instead of thiophenol.
m.p.: 118–119° C. (diisopropyl ether)
$^1$H-NMR(CDCl$_3$, δ): 1.24(d,J=5.9 Hz,3H), 3.81–4.02(m, 5H), 3.85(s,3H), 4.31–4.40(m,4H), 4.75(s,2H), 6.95(d,J=8.7 Hz,2H), 7.53(d,J=8.7 Hz,2H), 7.71(s,1H)

Test Example 1

Inhibitory activity against the growth of Hepatitis B virus (HBV)

HBV growth inhibitory activities of the compounds of the present invention were measured by a conventional method (K. Ueda, et al., Virology, 169, pp.213–216, 1989). HB611 cells (2×10$^4$, recombinant human hepatocellular carcinoma cells producing HBV) were cultured in Dulbecco ME medium containing 10% fetal bovine serum, streptomycin (100 μg/ml), penicillin (100 IU/ml), and Geneteicin (trade name, the antibiotic manufactured by Life Technologies, Co., Ltd., 0.2 mg/ml) at 37° C. The medium was changed with fresh medium on the second day and fifth day of the culture, and then the medium was changed with a medium containing a test compound at a final concentration of 0.005–100 mM after 8, 11, and 14 days of the culture. Total cellular DNAs were collected on the 17th day of the culture. Amounts of the HBV-DNAs in the cells were measured by the Southern blotting method, and concentrations achieving 50% inhibition of cytoplasmic HBV-DNA synthesis were determined. concentrations of compounds required for 50% extinction of HB611 cells were also determined. Results are shown in Table 2.

In the table, the compound numbers correspond to those listed in Table 1. Table 2 also shows as reference the results obtained by similar tests using the known compounds, i.e., dipivaloyloxymethyl ester of PMEA (Reference Example 1) and 9-[2-[bis(2,2,2-trifluoroethyl)phosphonylmethoxy] ethyl]-2-amino-6-p-toluylthiopurine disclosed in EP 632048 (Reference Example 2).

TABLE 2

| Compound No. | 50% inhibitory concentration against HBV-DNA synthesis (μM) | 50% cytotoxic concentration against HB611 cells (μM) |
|---|---|---|
| No.1 | 0.01 | >1,000 |
| No.2 | 0.08 | >1,000 |
| No.3 | 0.04 | >1,000 |
| No.4 | 0.05 | >1,000 |
| Reference 1 [a] | 18.8 | 11 |
| Reference 2 [b] | 0.06 | 108 |

[a] dipivaloyloxymethyl ester of PMEA
[b] 9-[2-[bis(2,2,2-trifluoroethyl)phosphonylmethoxy]ethyl]-2-amino-6-p-toluylthiopurine

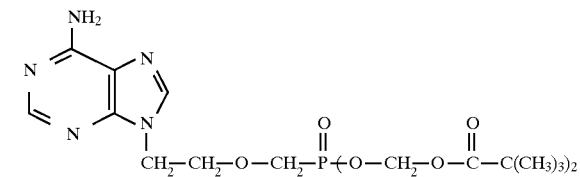

Test Example 2

HBV growth inhibitory activity of mouse serum after oral administration

Groups of mice each consisting of three mice were administered orally with a test compound at a single dose of 1 g/kg or 0.3 g/kg. Blood was collected 30 minutes after the administration, and serum was prepared. HB611 cells (2×10$^4$, recombinant human hepatocellular carcinoma cells producing HBV) were cultured in Dulbecco ME medium containing 10% fetal bovine serum, streptomycin (100 μg/ml), penicillin (100 IU/ml), and Geneteicin (trade name, the antibiotic manufactured by Life Technologies, Co., Ltd., 0.2 mg/ml) at 37° C. The medium was changed with fresh medium on the second day and fifth day of the culture, and then the medium was changed with a medium containing a test serum at a final concentration of 5% (V/V) after 8, 11, and 14 days of the culture. Total cellular DNAs were collected on the 17th day of the culture. Amounts of the HBV-DNAs in the cells were measured by the Southern blotting method, and rates of inhibition of cytoplasmic HBV-DNA synthesis were determined. As a reference, a similar test was carried out using PMEA. Results are shown in Table 3.

TABLE 3

| Compound No. | Dose of oral administration (g/kg) | Inhibitory rate against HBV-DNA synthesis (%) |
|---|---|---|
| No. 1 | 0.3 | 60.7 |
| No. 4 | 0.3 | 95.2 |
| PMEA | 1.0 | 35.5 |

From the foregoing explanations, it is apparent that the phosphonate nucleotide compounds of the present invention have excellent antiviral activity, and moreover, high oral absorbability and high safety to living bodies. Therefore, they are expected to be useful as ingredients of medicaments.

What is claimed is:

1. A phosphonate nucleotide compound represented by the following formula (I) or its salt, or a hydrate or a solvate thereof:

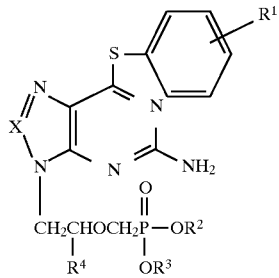

wherein $R^1$ represents hydrogen atom or a $C_1$–$C_6$ alkoxy group, $R^2$ and $R^3$ independently represent hydrogen atom, a $C_1$–$C_{22}$ alkyl group, an acyloxymethyl group, an acylthioethyl group, or an ethyl group substituted with one or more halogen atoms; $R^4$ represents hydrogen atom, a $C_1$–$C_4$ alkyl group, a $C_1$–$C_4$ hydroxyalkyl group, or a $C_1$–$C_4$ alkyl group substituted with one or more halogen atoms; and X represents a carbon atom or a nitrogen atom.

2. The phosphonate nucleotide compound or its salt, or a hydrate or a solvate thereof according to claim 1, wherein $R^1$ represents hydrogen atom or a $C_1$–$C_4$ alkoxy group; and $R^2$ and $R^3$ independently represent hydrogen atom, a $C_1$–$C_{22}$ alkyl group, or an ethyl group substituted with one or more halogen atoms.

3. The phosphonate nucleotide compound or its salt, or a hydrate or a solvate thereof according to claim 1, wherein $R^1$ represents hydrogen atom or a $C_1$–$C_4$ alkoxy group; $R^2$ and $R^3$ independently represent hydrogen atom, a $C_1$–$C_{22}$ alkyl group, or 2,2,2-trifluoroethyl group; and $R^4$ represents hydrogen atom or methyl group.

4. The phosphonate nucleotide compound or its salt, or a hydrate or a solvate thereof according to claim 1, wherein $R^1$ represents hydrogen atom or a $C_1$–$C_4$ alkoxy group; $R^2$ and $R^3$ independently represent hydrogen atom or 2,2,2-trifluoroethyl group; and $R^4$ represents hydrogen atom or methyl group.

5. The phosphonate nucleotide compound or its salt, or a hydrate or a solvate thereof according to claim 4, which is selected from the group consisting of:
2-amino-9-[2-[bis(2,2,2-trifluoroethyl)phosphonylmethoxy]ethyl]-6-phenylthiopurine;
2-amino-9-[2-[bis(2,2,2-trifluoroethyl)phosphonylmethoxy]ethyl]-6-p-methoxyphenylthiopurine;
2-amino-9-[2-[bis(2,2,2-trifluoroethyl)phosphonylmethoxy]ethyl]-6-m-methoxyphenylthiopurine;
2-amino-9-[2-[bis(2,2,2-trifluoroethyl)phosphonylmethoxy]ethyl]-6-o-methoxyphenylthiopurine;
2-amino-9-[2-[bis(2,2,2-trifluoroethyl)phosphonylmethoxy]ethyl]-6-p-ethoxyphenylthiopurine;
2-amino-9-[2-[bis(2,2,2-trifluoroethyl)phosphonylmethoxy]propyl]-6-phenylthiopurine;
2-amino-9-[2-[bis(2,2,2-trifluoroethyl)phosphonylmethoxy]propyl]-6-p-methoxyphenylthiopurine;
2-amino-9-[2-[(2,2,2-trifluoroethyl)phosphonylmethoxy]ethyl]-6-phenylthiopurine;
2-amino-9-[2-[(2,2,2-trifluoroethyl)phosphonylmethoxy]ethyl]-6-p-methoxyphenylthiopurine;
2-amino-9-[2-[phosphonylmethoxy]ethyl]-6-phenylthiopurine;
2-amino-9-[2-[phosphonylmethoxy]ethyl]-6-p-methoxyphenylthiopurine;
2-amino-9-[2-[bis(2,2,2-trifluoroethyl)phosphonylmethoxy]ethyl]-6-p-butoxyphenylthiopurine;
2-amino-9-[2-[bis(2,2,2-trifluoroethyl)phosphonylmethoxy]ethyl]-6-p-propoxyphenylthiopurine;
2-amino-9-[2-(bis(2,2,2-trifluoroethyl)phosphonylmethoxy]ethyl]-6-p-isopropoxyphenylthiopurine; and
2-amino-9-[2-[bis(2,2,2-trifluoroethyl)phosphonylmethoxy]ethyl]-6-p-isobutoxyphenylthiopurine.

6. The phosphonate nucleotide compound or its salt, or a hydrate or a solvate thereof according to claim 1, wherein $R^1$ is hydrogen atom or a $C_1$–$C_4$ alkoxy group; $R^2$ and $R^3$ represent 2,2,2-trifluoroethyl group; and $R^4$ represents hydrogen atom or methyl group.

7. The phosphonate nucleotide compound or its salt, or a hydrate or a solvate thereof according to claim 6, which is selected from the group consisting of:
2-amino-9-[2-[bis(2,2,2-trifluoroethyl)phosphonylmethoxy]ethyl]-6-phenylthiopurine;
2-amino-9-[2-[bis(2,2,2-trifluoroethyl)phosphonylmethoxy]ethyl]-6-p-methoxyphenylthiopurine;
2-amino-9-[2-[bis(2,2,2-trifluoroethyl)phosphonylmethoxy]ethyl]-6-m-methoxyphenylthiopurine;
2-amino-9-[2-[bis(2,2,2-trifluoroethyl)phosphonylmethoxy]ethyl]-6-o-methoxyphenylthiopurine;
2-amino-9-[2-[bis(2,2,2-trifluoroethyl)phosphonylmethoxy]ethyl]-6-p-ethoxyphenylthiopurine;
2-amino-9-[2-[bis(2,2,2-trifluoroethyl)phosphonylmethoxy]propyl]-6-phenylthiopurine;
2-amino-9-[2-[bis(2,2,2-trifluoroethyl)phosphonylmethoxy]propyl]-6-p-methoxyphenylthiopurine;
2-amino-9-[2-[bis(2,2,2-trifluoroethyl)phosphonylmethoxy]ethyl]-6-p-butoxyphenylthiopurine;
2-amino-9-[2-[bis(2,2,2-trifluoroethyl)phosphonylmethoxy]ethyl]-6-p-propoxyphenylthiopurine;
2-amino-9-[2-[bis(2,2,2-trifluoroethyl)phosphonylmethoxy]ethyl]-6-p-isopropoxyphenylthiopurine; and
2-amino-9-[2-[bis(2,2,2-trifluoroethyl)phosphonylmethoxy]ethyl]-6-p-isobutoxyphenylthiopurine.

8. The phosphonate nucleotide compound or its salt, or a hydrate or a solvate thereof according to claim 1, wherein $R^1$ is hydrogen atom or a $C_1$–$C_4$ alkoxy group; $R^2$ and $R^3$ represent 2,2,2-trifluoroethyl group; and $R^4$ represents hydrogen atom.

9. The phosphonate nucleotide compound or its salt, or a hydrate or a solvate thereof according to claim 8, which is selected from the group consisting of:
2-amino-9-[2-[bis(2,2,2-trifluoroethyl)phosphonylmethoxy]ethyl]-6-phenylthiopurine;
2-amino-9-[2-[bis(2,2,2-trifluoroethyl)phosphonylmethoxy]ethyl]-6-p-methoxyphenylthiopurine;
2-amino-9-[2-[bis(2,2,2-trifluoroethyl)phosphonylmethoxy]ethyl]-6-m-methoxyphenylthiopurine;
2-amino-9-[2-[bis(2,2,2-trifluoroethyl)phosphonylmethoxy]ethyl]-6-o-methoxyphenylthiopurine;
2-amino-9-[2-[bis(2,2,2-trifluoroethyl)phosphonylmethoxy]ethyl]-6-p-ethoxyphenylthiopurine;
2-amino-9-[2-[bis(2,2,2-trifluoroethyl)phosphonylmethoxy]ethyl]-6-p-butoxyphenylthiopurine;
2-amino-9-[2-[bis(2,2,2-trifluoroethyl)phosphonylmethoxy]ethyl]-6-p-propoxyphenylthiopurine;
2-amino-9-[2-[bis(2,2,2-trifluoroethyl)phosphonylmethoxy]ethyl]-6-p-isopropoxyphenylthiopurine; and
2-amino-9-[2-[bis(2,2,2-trifluoroethyl)phosphonylmethoxy]ethyl]-6-p-isobutoxyphenylthiopurine.

10. The phosphonate nucleotide compound or its salt, or a hydrate or a solvate thereof according to claim 1, wherein $R^1$ represents hydrogen atom or a $C_1$–$C_2$ alkoxy group; $R^2$ and $R^3$ represent 2,2,2-trifluoroethyl group; and $R^4$ represents hydrogen atom.

11. The phosphonate nucleotide compound or its salt, or a hydrate or a solvate thereof according to claim 1, wherein the compound is 2-amino-9-[2-[bis(2,2,2-trifluoroethyl) phosphonylmethoxy]ethyl]-6-phenylthiopurine.

12. The phosphonate nucleotide compound or its salt, or a hydrate or a solvate thereof according to claim 1, wherein the compound is 2-amino-9-[2-[bis(2,2,2-trifluoroethyl) phosphonylmethoxy]ethyl]-6-p-methoxyphenylthiopurine.

13. The phosphonate nucleotide compound or its salt, or a hydrate or a solvate thereof according to claim 1, wherein the compound is 2-amino-9-[2-[bis(2,2,2-trifluoroethyl) phosphonylmethoxy]ethyl]-6-m-methoxyphenylthiopurine.

14. The phosphonate nucleotide compound or its salt, or a hydrate or a solvate thereof according to claim 1, wherein the compound is 2-amino-9-[2-[-(bis(2,2,2-trifluoroethyl) phosphonylmethoxy]ethyl]-6-o-methoxyphenylthiopurine.

15. The phosphonate nucleotide compound or its salt, or a hydrate or a solvate thereof according to claim 1, wherein the compound is 2-amino-9-[2-[bis(2,2,2-trifluoroethyl) phosphonylmethoxy]ethyl]-6-p-ethoxyphenylthiopurine.

16. A pharmaceutical composition comprising a substance selected from the group of the phosphonate nucleotide compound and its salt, and a hydrate and a solvate thereof according to claim 1 together with a pharmaceutically acceptable additive.

17. A method for the treatment of a viral infection which comprises administering to a patient in need of such treatment an effective amount of a substance selected from the group of the phosphonate nucleotide compound and its salt, and a hydrate and a solvate thereof as defined in claim I.

18. A method according to claim 17 wherein the virus is hepatitis B virus.

* * * * *